(12) United States Patent
Sekiguchi et al.

(10) Patent No.: US 8,263,599 B2
(45) Date of Patent: Sep. 11, 2012

(54) STAT3/5 ACTIVATION INHIBITOR

(75) Inventors: Kazuo Sekiguchi, Otsu (JP); Takashi Suzuki, Otsu (JP); Yutaka Ohbuchi, Otsu (JP); Mitsuhiro Okuno, Otsu (JP); Naoto Ohi, Otsu (JP); Kenji Ohnishi, Otsu (JP); Masaaki Motoyama, Otsu (JP); Kenji Yoshida, Otsu (JP); Takeshi Kodama, Otsu (JP); Kazuhisa Sugiyama, Otsu (JP); Seiji Akamatsu, Otsu (JP); Kunihiko Kiyono, Otsu (JP); Yasuo Yanagihara, Otsu (JP); Takashi Watanabe, Otsu (JP); Kazuhiko Hayashi, Otsu (JP); Hideo Tanaka, Otsu (JP); Takumi Sumida, Otsu (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 114 days.

(21) Appl. No.: 12/311,500

(22) PCT Filed: Oct. 2, 2007

(86) PCT No.: PCT/JP2007/069645
§ 371 (c)(1),
(2), (4) Date: Apr. 1, 2009

(87) PCT Pub. No.: WO2008/044667
PCT Pub. Date: Apr. 17, 2008

(65) Prior Publication Data
US 2010/0210661 A1    Aug. 19, 2010

(30) Foreign Application Priority Data

Oct. 2, 2006    (JP) .................. 2006-271172

(51) Int. Cl.
*A61K 31/497*    (2006.01)
(52) U.S. Cl. .......... 514/252.11; 514/254.44; 514/253.11
(58) Field of Classification Search .............. 514/252.11
See application file for complete search history.

(56) References Cited

U.S. PATENT DOCUMENTS

| | | | |
|---|---|---|---|
| 3,182,085 A | 5/1965 | Pitchforth et al. | |
| 3,715,375 A | 2/1973 | Shen et al. | |
| 4,153,775 A | 5/1979 | Winkelmann et al. | |
| 4,211,699 A | 7/1980 | Winkelmann et al. | |
| 4,482,721 A | 11/1984 | Wegner et al. | |
| 4,978,672 A | 12/1990 | Bowman et al. | |
| 5,210,169 A | 5/1993 | Mühlebach et al. | |
| 5,401,772 A | 3/1995 | Yokoyama et al. | |
| 6,511,995 B1 | 1/2003 | Edamatsu et al. | |
| 2001/0029250 A1 | 10/2001 | Karras | |
| 2002/0065296 A1 | 5/2002 | Dumas et al. | |
| 2007/0270422 A1* | 11/2007 | Fukushima et al. | 514/235.5 |
| 2010/0004438 A1 | 1/2010 | Matsuyama et al. | |
| 2010/0261720 A1 | 10/2010 | Sumida et al. | |

FOREIGN PATENT DOCUMENTS

| | | |
|---|---|---|
| DE | 2146450 | 9/1971 |
| EP | 0 580 550 A1 | 1/1994 |
| EP | 1 101 755 A1 | 5/2001 |
| EP | 1 211 235 A2 | 6/2002 |
| EP | 1 256 341 A1 | 11/2002 |
| EP | 1 604 981 A1 | 12/2005 |
| GB | 1 353 520 | 5/1974 |
| GB | 1 494 117 | 12/1977 |
| GB | 2 374 009 A | 10/2002 |
| JP | 2001-89412 | 4/2001 |
| JP | 2001-89450 | 4/2001 |
| JP | 2002-507601 | 3/2002 |
| JP | 2004-35475 | 2/2004 |
| RU | 2003101342 | 7/2004 |
| WO | WO-95/01326 | 1/1995 |
| WO | WO-96/40620 | 12/1996 |
| WO | WO-99/24404 | 5/1999 |
| WO | WO-99/40073 | 8/1999 |
| WO | WO-99/40083 | 8/1999 |
| WO | WO-99/48871 | 9/1999 |

(Continued)

OTHER PUBLICATIONS

Montori et al (BMJ 334:882-884, 2007).*

(Continued)

*Primary Examiner* — Craig Ricci
(74) *Attorney, Agent, or Firm* — Finnegan, Henderson, Farabow, Garrett & Dunner, LLP

(57) ABSTRACT

An object of the present invention is to provide a STAT3/5 activation inhibitor. The present invention provides a STAT3/5 activation inhibitor containing an aromatic compound represented by the general formula or a salt thereof as an active ingredient:

$$R^1 \diagup \diagdown \diagup R^2 \diagdown Y - A \diagdown X_1 \diagup \qquad (1)$$

wherein $X_1$ represents a nitrogen atom or a group —CH=, $R_1$ represents a group —Z—$R^6$, in which Z represents a group —CO—, a group —CH(OH)— or the like, $R^6$ represents a 5- to 15-membered monocyclic, dicyclic or tricyclic saturated or unsaturated heterocyclic group having 1 to 4 nitrogen atoms, oxygen atoms or sulfur atoms, $R^2$ represents a hydrogen atom or a halogen atom, Y represents a group —O—, a group —CO—, a group —CH(OH)— or a lower alkylene group, and A represents a group $$—NHCO—\triangledown$$

wherein $R^3$ represents a hydrogen atom, a lower alkoxy group or the like, p represents 1 or 2, $R^4$ represents an imidazolyl lower alkyl group or the like.

6 Claims, No Drawings

FOREIGN PATENT DOCUMENTS

| WO | WO-00/00470 | | 1/2000 |
|---|---|---|---|
| WO | WO-02/32408 | A2 | 4/2000 |
| WO | WO-00/42012 | | 7/2000 |
| WO | WO-00/46203 | | 8/2000 |
| WO | WO-00/58279 | | 10/2000 |
| WO | WO-01/02359 | A1 | 11/2001 |
| WO | WO-01/98256 | A1 | 12/2001 |
| WO | WO-02/16358 | A2 | 2/2002 |
| WO | WO-02/26191 | A2 | 4/2002 |
| WO | WO-02/053150 | A1 | 7/2002 |
| WO | WO-02/102787 | A2 | 12/2002 |
| WO | WO-03/018586 | A1 | 3/2003 |
| WO | WO-03/035602 | A1 | 5/2003 |
| WO | WO-03/035627 | A1 | 5/2003 |
| WO | WO-03/070728 | A2 | 8/2003 |
| WO | WO-03/076406 | A1 | 9/2003 |
| WO | WO-2004/080966 | A1 | 9/2004 |
| WO | WO-2005/007621 | A2 | 1/2005 |
| WO | WO-2005/009940 | A1 | 2/2005 |
| WO | WO 2006/014012 | * | 2/2006 |
| WO | WO-2006/014012 | A2 | 2/2006 |
| WO | WO 01/90101 | A1 | 11/2011 |

OTHER PUBLICATIONS

Gao et al (Expert Opin Ther Targets 11:869-880, 2007).*
Levinthal et al (Clinical Diabetes 17(2), 1999).*
Balcells et al.; "Synthesis of Phenoxyphenyl Pyride and Pyrazine Carboxamides. Activity Against *Cydia Pomonella* (L.) Eggs"; J. Agric Food Chem., vol. 48, No. 1, pp. 83-87, (2000).
Mühlebach; "Pyrazoles—A Novel Class of Blocking Agents for Isocyanates"; Journal of Polymer Science, vol. 32, No. 4, pp. 735-765, (1994).
Bethegnies et al.; "Substituted Phenylthiophenylamines With Antiinflammatory Activity"; IL Farmaco, vol. 44, Nos. 7-8, pp. 683-694, (1989).
Anagnostou et al.; "Synthesis of Blocked MDI Adducts, Their DSC Evaluation and Effect of Pigmentation"; Journal of Coating Technology, vol. 53, No. 673, pp. 35-45, (1981).
George et al., "Metabolic Activation Stimulates Acid Secretion and Expression of Matrix Degrading Proteases in Human Osteoblasts", Annals of the Rheumatic Diseases, vol. 63, No. 1, pp. 67-70, (2004).
Barnstein et al., "STAT5 Expression is Required for IgE-Mediated Mast Cell Function", The Journal of Immunology, vol. 177, pp. 3421-3426, (2006).
Gao et al., "Disruption of Neural Signal Transducer and Activator of Transcription 3 causes Obesity, Diabetes, Infertility, and Thermal Dysregulation", PNAS, vol. 101, No. 13, pp. 4661-4666, (2004).
Sano et al., "STAT3 Links Activated Keratinocytes and Immunocytes Required for Development of Psoriasis in a Novel Transgenic Mouse Model"; Nature Medicine, vol. 11, No. 1, pp. 43-49, (2005).
Yoshida et al., "Activation of STAT3 by the Hepatitis C Virus Core Protein Leads to Cellular Transformation", The Journal of Experimental Medicine, vol. 196, No. 5, pp. 641-653, (2002).
Maggio et al., "Interleukin-6 in Aging and Chronic Disease: A Magnificent Pathway", The Journal of Gerontology, vol. 61A, No. 6, pp. 575-584, (2006).
Decision of Grant for Russian Application No. 2007-108298 dated Oct. 13, 2010.
Molina, Vered et al., "Intravenous Immunoglobulin and Fibrosis," Clinical Reviews in Allergy & Immunology, vol. 29, No. 3, pp. 321-326 (2005).
English Translation of Korean Office Action for Korean Patent Application No. 10-2009-7006358 dated Apr. 1, 2011.
European Office Action in Counterpart EP Application No. 05 780 290.2-1521 dated Sep. 15, 2011.
Abad-Zapatero, C. et al., "Ligand Efficiency Indices for an Effective Mapping of Chemico-Biological Space: The Concept of an Atlas-Like Representation," Drug Discovery Today, 1-8 (2010).
Bastian, B.C., "Genetic Progression From Melanocyte to Malignant Melanoma," The Progression to Malignancy 197, 201 (V.J. Hearing et al., eds. (2006).
Belikov, V.G., "Pharmaceutical Chemistry," Highest School, Moscow, pp. 43-47 (1993).

Cannistra, S. et al., "Ovarian Cancer, Fallopian Tube Carcinoma, and Peritoneal Carcinoma," 2 Cancer Principles & Practice of Oncology 1568 (V.T. DeVita, Jr. et al. eds., 8th ed.) (2008).
Collins, I. et al., "Design and Development of Signal Transduction Inhibitors for Cancer Treatment: Experience and Challenges With Kinase Targets," Current Signal Transduction Therapy, 1, 13-14 (2006).
De Arruda, MD, F.F. et al.,"Intensity-Modulated Radiation Therapy for the Treatment of Oropharyngeal Carcinoma: The Memorial Sloan-Kettering Cancer Center Experience," Int. J. Radiation Oncology Biol. Phys., 64(2), 363-373 (2006).
Druker, B.J., "Chronic Myelogenous Leukemia," 2 Cancer Principles & Practice of Oncology 2121 (V.T. DeVita, Jr. et al. eds., 7th ed. ( 2005).
Faderi, S. et al., "Myelodysplastic Syndromes," 2 Cancer Principles & Practice of Oncology 2133 (V.T. DeVita, Jr. et al. eds., 7th ed. (2005).
Final Office Action for copending U.S. Appl. No. 11/659,689 dated Dec. 22, 2010.
Hann, B. et al., "Building 'Validated' Mouse Models of Human Cancer," Current Opinion in Cell Biology, 13, 778-784 (2001).
Hawley, A.T. et al., "Etiology of Cancer: Cancer Susceptibility Syndromes," 2 Cancer Principles & Practice of Oncology 157-168, 157 (V.T. DeVita et al. eds., 8th ed., 2008).
Kamb, A., "What's Wrong With Our Cancer Models?," Nature Reviews Drug Discovery 2, 161-165 (2005).
Kholodov, L.E. et al., "Clinic Pharmacokinetics," Manual, Medicine, Moscow, pp. 83-98, 134-138, 160, 378-380, (1985).
Kumar, P. et al., "Pulmonary Fibrosis and Lung Cancer: Risk and Benefit Analysis of Pulmonary Resection," The Journal of Thoracic and Cardiovascular Surgery, 125(6) 1321-1327, 1322 (2003).
Libutti, S.K. et al., "Colon Cancer," 1 Cancer Principles & Practice of Oncology 1232, 1243 (V.T. DeVita, Jr. et al eds., 8th ed.) (2008).
Mosby Medical Encyclopedia, Revised Edition, p. 320 (1996).
Nishiwara, R. et al., Machine Translation of WO2004/080966 (Sep. 23, 2004).
Notice of Allowance in U.S. Appl. No. 11/659,689 mailed Sep. 26, 2011.
O'Brien, S. et al., "Chronic Lymphoid Leukemias," 2 Cancer Principles & Practice of Oncology 2133 (V.T. DeVita, Jr. et al. eds, 7th ed. (2005).
Odunsi, K. et al., "Molecular Biology of Gynecologic Cancers," 2 Cancer Principles & Practice of Oncology 1487, 1492 (V.T. DeVita, Jr. et al. eds., 8th ed) (2008).
Office Action for copending U.S. Appl. No. 11/659,689 dated May 25, 2011.
Office Action for copending U.S. Appl. No. 12/095,930 dated Aug. 17, 2011.
Olive, K.P. et al., "The Use of Targeted Mouse Models for Preclinical Testing of Novel Cancer Therapeutics," Clinical Cancer Research 12, 5277-5287 (2006).
Pusztai, L. et al., "Histopathologic and Molecular Markers of Prognosis and Response to Therapy," Breast Cancer 324, 326-328 (Kelly K. Hunt et al., ed., 2nd ed.) (2008).
Restriction Requirement in U.S. Appl. No. 11/659,689 mailed Dec. 30, 2009.
Restriction Requirement in U.S. Appl. No. 11/659,689 mailed Sep. 18, 2009.
Restriction Requirement in U.S. Appl. No. 12/095,930 mailed May 26, 2011.
Russian Office Action for Russian Application No. 2009116653 dated Oct. 21, 2011.
Rustgi, A.K., "Molecular Biology of the Esophagus and Stomach," 1 Cancer Principles & Practice of Oncology, 989-993, 991 (V.T DeVita, Jr. et al. eds, 8th ed.) (2008).
Scheinberg, D.A. et al., "Management of Acute Leukemias," 2 Cancer Principles & Practice of Oncology 2088, 2092 (V.T. DeVita, Jr. et al. eds., 7th ed.) (2005).
Sergeev, Professor, "Short Course of Molecular Pharmacology," Moscow Medical Institute, Moscow, p. 10 (1975).

Sharpless, N.E. et al., "The Mighty Mouse: Genetically Engineered Mouse Models in Cancer Drug Development," Nature Reviews Drug Discovery 5, 741-754 (2006).

Smith, N.F. et al., "The Application of Cassette Dosing for Pharmacokinetic Screening in Small-Molecule Cancer Drug Discovery," Molecular Cancer Therapeutics, 6, 428-440, 428 (2007).

Song, Y. et al., "Cancer: A Conceptual Framework," 1 Cancer Principles & Practice of Oncology 1, 5-6 (V.T. Devita, Jr. et al. eds., 8th ed., 2008).

Traynor, A.M., "Systemic Treatment of Advanced Non-Small Cell Lung Cancer," Drugs of Today, 40(8), 697-710, 698 (2004).

* cited by examiner

STAT3/5 ACTIVATION INHIBITOR

TECHNICAL FIELD

The present invention relates to a STAT3/5 activation inhibitor.

BACKGROUND ART

A protein family of STAT (signal transducers and activators of transcription) is one of a DNA binding protein and plays a role in information transmission and transcription activation. At present, the STAT family is known to have 6 different members (STAT 1, STAT 2, STAT 3, STAT 4, STAT 5 and STAT 6) and several iso-forms (STAT 1α, STAT 1β, STAT 3α, STAT3β, STAT 5a and STAT 5b). The activity of STAT is regulated by stimulation of various cytokines and mitogen. When a cytokine binds to its receptors, Janus protein tyrosine kinase (JAK) associated with the receptors is activated.

STAT 3 has a SH2 (src homology 2) domain capable of recognizing the structure of a specifically phosphorylated tyrosine. It is considered that STAT 3 specifically recognizes the phosphorylated tyrosine within a gp130 cell region and is conveyed onto gp 130 and tyrosine is phosphorylated by JAK. STAT 3 having phosphorylated tyrosine forms a STAT 3 dimer (homodimer) via its SH2 domain or a dimer (heterodimer) of STAT 3 and STAT1, which moves into a nucleus, and recognizes a specific DNA sequence and binds it. In this way, STAT3 is known to regulate transcription of many genes.

Such in-vivo roles of STAT3/5 are reported in several documents.

For example, Non-Patent Document 1 describes the relationships between activation of STAT 3 and IL-6-signaling pathways and between IL-6 and chronic diseases such as Alzheimer's disease, rheumatism, Crohn disease and anemia and cancer associated disease such as cachexia.

Furthermore, Non-Patent Document 2 describes the relationship between STAT 3 activation and Hepatitis C Virus, Non-Patent Document 3 describes the relationship between STAT 3 activation and psoriasis, individually. Moreover, Non-Patent Document 2 sets forth the relationships between STAT 3 and an inflammatory disease and an autoimmune disease, and Non-Patent Document 4 sets forth the relationships between STAT 3 activation and obesity, diabetes, infertility, and thermal dysregulaton, etc., individually. Non-Patent Documents 5 and 6, etc. describe that STAT5 is a critical factor in IgE-induced MC (mast cell) activation, and inflammatory and autoimmune diseases, and describe STAT5's roles in allergies, inflammations, hyperprolactinemia, and malignant tumors.

On the other hand, it is known that an aromatic compound having a collagen production inhibitory action is present (Patent Document 1). However, it has been not yet known that the aromatic compound described in Patent Document 1 has a STAT5/5 activation inhibitory action.

[Patent Document 1] WO2006/014012
[Patent Document 2] US2001/0029250
[Non-Patent Document 1] J. Gerontology; MEDICAL SCIENCES 2006, Vol. 61A, No. 6, 575-584
[Non-Patent Document 2] J. Exp. Med. Vol. 196, No. 5, 2002, 641-653
[Non-Patent Document 3] Nature Medicine Vol. 11, No. 1, 2005, 43-49
[Non-Patent Document 4] PNAS Mar. 30, 2004, vol. 101, no. 13, 4661-4666
[Non-Patent Document 5] J. Immunology, 2006, 177: 3421-3426,
[Non-Patent Document 6] Ann. Rheum. Dis. 2004; 63: 67-71

DISCLOSURE OF THE INVENTION

An object of the present invention is to provide a STAT3/5 activation inhibitor.

The present inventors repeatedly studied on an aromatic compound described in Patent Document 1. As a result, they found that the compound has a STAT3/5 activation inhibitory action. The present invention has been attained based on such a finding.

Therefore, the present invention provides STAT3/5 activation inhibitors represented by the following items A to C.

Item A: A STAT3/5 activation inhibitor containing an aromatic compound (hereinafter sometimes simply referred to as an aromatic compound (1)) represented by the general formula or a salt thereof as an active ingredient:

[Formula 1]

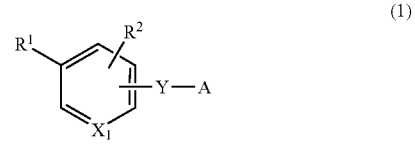

wherein $X_1$ represents a nitrogen atom or a group —CH=,
$R^1$ represents a group —Z—$R^6$,
Z represents a group —N($R^8$)—B—, a group —B—N($R^8$)—, a group —$B_0$—O—, a group

[Formula 2]

—NHCO—▽— a group —CO—, a group-CH(OH)—, a group —N($R^{9a}$)—CO—N—($R^{9b}$)—, a group —N=CH—, a group —N($R^{10a}$)—$SO_2$—($B_{22a}$)e-, a lower alkenylene group, a group —NHCO—$B_1$—, a group —NHCO—$B_2$—(W)u-, a group —$B_0$—O—$B_{19a}$—, a group

[Formula 3]

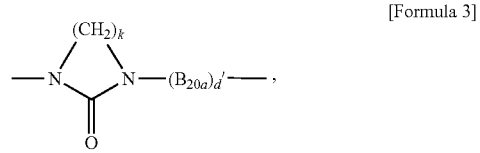

a group

[Formula 4]

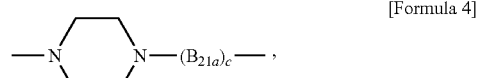

a group —$SO_2$—N($R^{10b}$)—, a group —S—, a lower alkynylene group, a lower alkylene group, a group —N($R^{8d}$)— or a group —CO—NH—$B_{18a}$—,
$R^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group,
$B_0$ represents a lower alkylene group,
$B_1$ represents a lower alkenylene group that may have a phenyl group as a substituent,
$B_2$ represents a lower alkylene group that may be substituted by a group selected from the group consisting of a lower alkoxy group and a phenyl group,
$R^{9a}$ represents a hydrogen atom or a lower alkyl group,
$R^{9b}$ represents a hydrogen atom or a lower alkyl group,
$R^{10a}$ represents a hydrogen atom or a lower alkyl group,
$B_{22a}$ represents a lower alkylene group or a lower alkenylene group,
e represents 0 or 1,
$B_{18a}$ represents a lower alkylene group,
$B_{19a}$ represents a lower alkylene group,
$B_{20a}$ represents a lower alkylene group,
$B_{21a}$ represents a lower alkylene group,
k represents 2 or 3,
c represents 0 or 1,
d' represents 0 or 1,
$R^{10b}$ represents a hydrogen atom or a lower alkyl group,
$R^{8d}$ represents a hydrogen atom or a lower alkyl group,
W represents an oxygen atom, a group —NH—, or a sulfur atom,
u represents 0 or 1,
$R^6$ represents 5- to 15-membered monocyclic, dicyclic or tricyclic saturated or unsaturated heterocyclic group having 1 to 4 nitrogen atoms, oxygen atoms or sulfur atoms (that may have 1 to 3 substituents, which are selected from the group consisting of an oxo group; a lower alkoxy group that may have a halogen atom as a substituent; a lower alkyl group that may have a halogen atom as a substituent; a halogen atom; a lower alkylsulfonyl group; a phenyl group that may be substituted by a lower alkyl group that may have a halogen atom on the phenyl ring; a lower alkylthio group, a pyrrolyl group, a benzoyl group; a lower alkanoyl group; lower alkoxycarbonyl group; and an amino group that may have a group selected from the group consisting of a lower alkyl group and a lower alkanoyl group as a substituent, on the heterocyclic ring), an adamantyl group, a naphthyl group (that may have 1 to 3 groups selected from the group consisting of a lower alkyl group, a halogen atom, and an amino group that may have a group selected from the group consisting of a lower alkyl group and a lower alkanoyl group as a substituent, on the naphthalene ring), an alkyl group that may have a lower alkoxy group as a substituent, a cycloalkyl group that may be substituted by a group selected from the group consisting of an amino substituted lower alkyl group that may have a lower alkyl group and a lower alkyl group that may have a halogen atom as a substituent, on the cycloalkyl ring, a lower alkenyl group that may have a halogen atom as a substituent, a lower alkanoyl group, a benzoyl group (that may have 1 to 3 groups selected from the group consisting of a lower alkyl group that may have a halogen atom and halogen atom, as a substituents, on the phenyl ring), a halogen atom substituted lower alkyl group, cycloalkyl lower alkyl group or a group

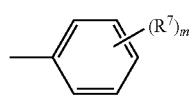

[Formula 5]

$R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group or a 5- or 6-membered saturated or unsaturated heterocyclic group having 1 to 4 nitrogen atoms, oxygen atoms, or sulfur atoms (that may have an oxo group on the heterocyclic ring),
m represents an integer from 1 to 5(when m represents 2 to 5, two to five $R^7$s may be identical or different) and $R^2$ represents a hydrogen atom, a halogen atom, or a lower alkyl group,
Y represents a group —O—, a group —N($R^5$)—, a group —CO—, a group —CH(OH)—, a lower alkylene group, a group —S(O)n-, or a group —C(=N—OH)—,
$R^5$ represents a hydrogen atom, a lower alkyl group, a lower alkanoyl group, a benzoyl group, a phenyl lower alkyl group, or a cycloalkyl group,
n represents 0, 1, or 2,
A represents a group

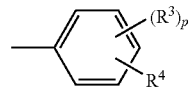

[Formula 6]

or a group

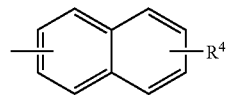

[Formula 7]

p represents 1 or 2,
$R^3$ represents a hydrogen atom, a lower alkoxy group, a halogen atom, a lower alkyl group that may have a halogen atom as a substituent, a lower alkoxycarbonyl group, a carboxy group, a group —CONR$^{11}$R$^{12}$, or a cyano group, wherein $R^{11}$ and $R^{12}$ may be identical or different and each represent a hydrogen atom, a lower alkyl group, a cycloalkyl group, or a phenyl group, and $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring,
$R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group a group

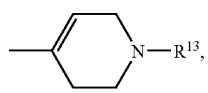
[Formula 8]

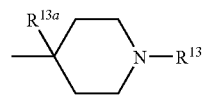
[Formula 9]

or a group -(T)$_l$-N(R$^{14}$)R$^{15}$,

R$^{13}$ represents a hydrogen atom, a lower alkyl group that may have a halogen atom as a substituent, a lower alkanoyl group that may have a halogen atom as a substituent, a lower alkoxycarbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group, R$^{13a}$ represents a hydrogen atom or a hydroxyl group, T represents a lower alkylene group, a group —N(R$^{17}$)—B$_3$—CO—, a group —B$_{19}$—N(R$^{18}$)—CO—, a group —B$_4$—CO—, a group -Q-B$_5$—CO—, a group —B$_6$—N(R$^{19}$)—B$_7$—CO—, a group —CO—B$_8$—, a group —CH(OH)—B$_9$—, a group —CO—B$_{10}$—CO—, a group —CH(OH)—B$_{11}$—CO—, a group —CO—, a group —SO$_2$—, or a group —B$_{23a}$—CO—CO—, wherein R$^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, B$_3$ represents a lower alkylene group, B$_{19}$ represents a lower alkylene group, R$^{18}$ represents a hydrogen atom or a lower alkyl group, B$_4$ represents a lower alkenylene group or a lower alkylene group that may have a hydroxyl group as a substituent, Q represents an oxygen atom or a group —S(O)n- (wherein n is the same as described above), B$_5$ represents a lower alkylene group, B$_6$ represents a lower alkylene group, R$^{19}$ representsa hydrogen atom or a lower alkanoyl group, B$_7$ represents a lower alkylene group, B$_8$ represents a lower alkylene group, B$_9$ represents a lower alkylene group, B$_{10}$ represents a lower alkylene group, B$_{11}$ represents a lower alkylene group, B$_{23a}$ represents a lower alkylene group, l represents 0 or 1, R$^{14}$ represents a hydrogen atom or an alkyl group that may have a hydroxyl group as a substituent, R$^{15}$ represents (2) a hydroxyl group-substituted alkyl group, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydroquinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolylcarbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

[Formula 10]

(26) a carbonyl lower alkyl group substituted by a group

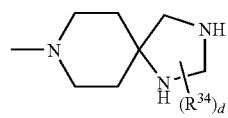
[Formula 11]

(27) a group —CO—$B_{20}$—N($R^{36}$)$R^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an oxo group or a phenyl group,
d represents an integer from 0 to 3,
$B_{20}$ represents a lower alkylene group,
$R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 phenyl lower alkyl groups that may have a lower alkylenedioxy group on the phenyl ring, may be present as a substituent(s),
$R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

[Formula 12]

wherein, on the heterocyclic ring, 1 to 3 substituents may be present which are selected from the group consisting of (28) a phenyl-substituted lower alkyl group, which has 1 to 2 phenyl groups that may be substituted by 1 to 3 groups on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, and that may have a pyridyl group on the lower alkyl group,

(29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazolidinyl lower alkanoyl group that may be substituted, on the thiazolidine ring, by a group selected from the group consisting of an oxo group and a group

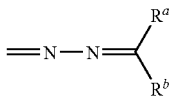
[Formula 13]

(wherein $R^a$ and $R^b$ each represent a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group —($B_{12}$CO)t-N($R^{20}$)$R^{21}$, (50) a group —(CO)o-$B_{13}$—N($R^{22}$)$R^{23}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadizole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group —(O—$B_{15}$)s-CO—N($R^{26}$)$R^{27}$, (85) a group —N($R^{28}$)—CO—$B_{16}$—N($R^{29}$)$R^{30}$, (86) a group —N($R^{31}$)—$B_{17}$—CO—N($R^{32}$)$R^{33}$, (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, $R^{20}$ and $R^{21}$ may be identical or different and each represent a hydrogen atom; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or a cycloalkyl group; and $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring), o represents 0 or 1, $B_{13}$ represents a lower alkylene group, $R^{22}$ and $R^{23}$ may be identical or different and each represent a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group and a phenyl lower alkyl group that may have a lower alkylenedioxy group as a substituent on the phenyl ring), $B_{15}$ represents a lower alkylene group, s represents 0 or 1, $R^{26}$ and $R^{27}$ may be identical or different and each represent a hydrogen atom, a lower alkyl group, a phenyl lower alkyl group, or an imidazolyl lower alkyl group, and $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 phenyl lower alkyl groups that may have a lower alkylenedioxy group as a substituent on the phenyl ring may be present as a substituent(s)), $R^{28}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group (wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring).

However, that the aforementioned compound or a salt thereof satisfies the following requirements (i) to (v):

(i) when $X_1$ represents a group —CH═, then $R^3$ represents a hydrogen atom;

(ii) when $X_1$ represents a group —CH═, 1 represents 1, T represents —CO—, and $R^{14}$ represents a hydrogen atom or an alkyl group that may have a hydroxyl group as a substituent, $R^{15}$ represents the group (24);

(iii) when $X_1$ represents a group —CH═, 1 represents 1, and T represents —N($R^{17}$)—$B_3$—CO—, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring, wherein, on the heterocyclic ring, 1 to 3 groups of (28) are present as a substituent(s);

(iv) when $X_1$ represents a nitrogen atom, and l represents 0, or when $X_1$ represents a nitrogen atom, l represents 1, and T represents —CO— or —$SO_2$, $R^{15}$ is not a group (5), (7), (19), or (20); and (v) when $R^6$ represents a cycloalkyl group that may have on the cycloalkyl ring, a substituent selected from the group consisting of an amino-substituted lower alkyl group that may have a lower alkyl group and a lower alkyl group that may have a halogen atom as a substituent, $R^4$ represents a group -(T)$_l$-N($R^{14}$)$R^{15}$ (wherein T and l are the same as described above, and $R^{14}$ and $R^{15}$, together with the nitrogen atom to which they bind, may bind to each other, directly or via a nitrogen atom, oxygen atom, or sulfur atom to form a 5- to 10-membered saturated heterocyclic ring; or $R^{14}$ and $R^{15}$ form a group

[Formula 14]

Item B: The STAT3 activation inhibitor according to item A for preventing or treating a symptom or disease associated with activation of STAT3.

Item C: The STAT3 activation inhibitor according to item B, in which the symptom or disease associated with activation of STAT3 is autoimmune disease, diabetes, infection, central disease, cancer-associated disease or psoriasis.

The present invention further provides a method for preventing or treating a symptom or disease associated with activation of STAT3 by administering, to a patient, an effective dose of an aromatic compound (1) or a salt thereof according to item A.

The present invention further provides use of a compound (1) or a salt thereof according to item A for producing the STAT3/5 activation inhibitor.

The aromatic compound (1) or a salt thereof serving as an active ingredient of the STAT3/5 activation inhibitor of the present invention is an aromatic compound (1) or a salt thereof represented by item 1 below and preferably aromatic compounds or salts thereof represented by items 2 to 48.

Item 1: An aromatic compound or a salt thereof represented by the general formula:

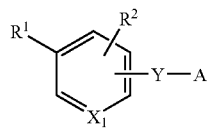

[Formula 15]

wherein $X_1$ represents a nitrogen atom or a group —CH═, $R^1$ represents a group —Z—$R^6$, Z represents a group —N($R^8$)—B—, a group —B—N($R^8$)—, a group —$B_0$—O—, a group

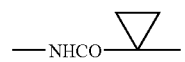

[Formula 16]

a group —CO—, a group-CH(OH)—, a group —N($R^{9a}$)—CO—N—($R^{9b}$)—, a group —N═CH—, a group —N($R^{10a}$)—$SO_2$—($B_{22a}$)e-, a lower alkenylene group, a group —NHCO—$B_1$—, a group —NHCO—$B_2$—(W)u-, a group —$B_0$—O—$B_{19a}$—, a group

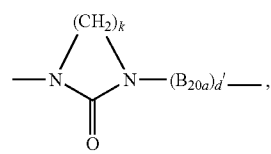

[Formula 17]

a group

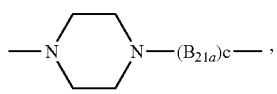

[Formula 18]

a group —$SO_2$—N($R^{10b}$)—, a group —S—, a lower alkynylene group, a lower alkylene group, a group —N($R^{8d}$)— or a group —CO—NH—$B_{18a}$—, $R^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group, $B_0$ represents a lower alkylene group, $B_1$ represents a lower alkenylene group that may have a phenyl group as a substituent, $B_2$ represents a lower alkylene group that may be substituted by a group selected from the group consisting of a lower alkoxy group and a phenyl group, $R^{9a}$ represents a hydrogen atom or a lower alkyl group, $R^{9b}$ represents a hydrogen atom or a lower alkyl group, $R^{10a}$ represents a hydrogen atom or a lower alkyl group, $B_{22a}$ represents a lower alkylene group or a lower alkenylene group, e represents 0 or 1, $B_{18a}$ represents a lower alkylene group, $B_{19a}$ represents a lower alkylene group,
$B_{20a}$ represents a lower alkylene group,
$B_{21a}$ represents a lower alkylene group,
k represents 2 or 3,
c represents 0 or 1,
d' represents 0 or 1,
$R^{10b}$ represents a hydrogen atom or a lower alkyl group,
$R^{8d}$ represents a hydrogen atom or a lower alkyl group,
W represents an oxygen atom, a group —NH—, or a sulfur atom,
u represents 0 or 1,
$R^6$ represents 5- to 15-membered monocyclic, dicyclic or tricyclic saturated or unsaturated heterocyclic group having 1 to 4 nitrogen atoms, oxygen atoms or sulfur atoms (that may have 1 to 3 substituents, which are selected from the group consisting of an oxo group; a lower alkoxy group that may have a halogen atom as a substituent; a lower alkyl group that may have a halogen atom as a substituent; a halogen atom; a lower alkylsulfonyl group; a phenyl group that may be substituted by a lower alkyl group that may have a halogen atom on the phenyl ring; a lower alkylthio group, a pyrrolyl group, a benzoyl group; a lower alkanoyl group; lower alkoxycarbonyl group; and an amino group that may have a group selected from the group consisting of a lower alkyl group and a lower alkanoyl group as a substituent, on the heterocyclic ring), an adamantly group, a naphthyl group (that may have 1 to 3 groups selected from the group consisting of a lower alkyl group, a halogen atom, and an amino group that may have a group selected from the group consisting of a lower alkyl group and a lower alkanoyl group as a substituent, on the naphthalene ring), an alkyl group that may have a lower alkoxy group as a substituent, a cycloalkyl group that may be substituted by a group selected from the group consisting of an amino substituted lower alkyl group that may have a lower alkyl group and a lower alkyl group that may have a halogen atom as a substituent, on the cycloalkyl ring, a lower alkenyl group that may have a halogen atom as a substituent, a lower alkanoyl group, a benzoyl group (that may have 1 to 3 groups selected from the group consisting of a lower alkyl group that may have a halogen atom and halogen atom, as a substituents, on the phenyl ring), a halogen atom substituted lower alkyl group, cycloalkyl lower alkyl group or a group

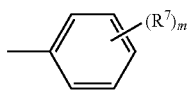
[Formula 19]

$R^7$ represents a hydrogen atom, a phenyl group, a carboxy group, a hydroxyl group, a halogen atom, a lower alkyl group that may have a halogen atom as a substituent, a phenoxy group, a lower alkoxy group that may have a halogen atom as a substituent, a lower alkylenedioxy group, an amino group that may have, as a substituent, a group selected from the group consisting of a lower alkyl group, a lower alkanoyl group, a benzoyl group, and a cycloalkyl group, a cyano group, a lower alkanoyl group that may have a halogen atom as a substituent, a lower alkylsulfonyl group, an aminosulfonyl group, a lower alkoxycarbonyl group, a lower alkanoyloxy group, a lower alkoxycarbonyl lower alkyl group or a 5- or 6-membered saturated or unsaturated heterocyclic group having 1 to 4 nitrogen atoms, oxygen atoms, or sulfur atoms (that may have an oxo group on the heterocyclic ring), m represents an integer from 1 to 5 (when m represents 2 to 5, two to five $R^7$s may be identical or different) and $R^2$ represents a hydrogen atom, a halogen atom, or a lower alkyl group, Y represents a group —O—, a group —N($R^5$)—, a group —CO—, a group —CH(OH)—, a lower alkylene group, a group —S(O)n-, or a group —C(=N—OH)—, $R^5$ represents a hydrogen atom, a lower alkyl group, a lower alkanoyl group, a benzoyl group, a phenyl lower alkyl group, or a cycloalkyl group, n represents 0, 1, or 2, A represents a group

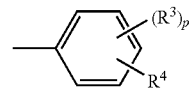
[Formula 20]

or a group

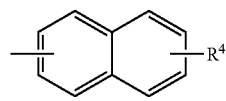
[Formula 21]

p represents 1 or 2, $R^3$ represents a hydrogen atom, a lower alkoxy group, a halogen atom, a lower alkyl group that may have a halogen atom as a substituent, a lower alkoxycarbonyl group, a carboxy group, a group —CONR$^{11}$R$^{12}$, or a cyano group, wherein $R^{11}$ and $R^{12}$ may be identical or different and each represent a hydrogen atom, a lower alkyl group, a cycloalkyl group, or a phenyl group, and $R^{11}$ and $R^{12}$, together with the nitrogen atom to which they bind, may bind to each other, directly or via a nitrogen atom, oxygen atom, or sulfur atom to form a 5- to 7-membered saturated heterocyclic ring, $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

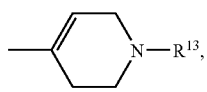
[Formula 22]

a group

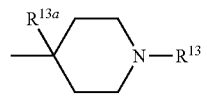
[Formula 23]

or a group -(T)$_1$-N(R$^{14}$)R$^{15}$,

R$^{13}$ represents a hydrogen atom, a lower alkyl group that may have a halogen atom as a substituent, a lower alkanoyl group that may have a halogen atom as a substituent, a lower alkoxycarbonyl group, a phenyl lower alkyl group that may have a lower alkylenedioxy group as a substituent on the phenyl ring, an imidazolyl lower alkyl group, a lower alkoxycarbonyl lower alkyl group, a carboxy lower alkyl group, a benzoyl group, a morpholino-substituted lower alkanoyl group, a piperazinyl carbonyl lower alkyl group that may be substituted, on the piperazine ring, by a phenyl lower alkyl group that may have a lower alkylenedioxy group as a substituent on the phenyl ring, a piperazinyl lower alkanoyl group that may be substituted, on the piperazine ring, by a phenyl lower alkyl group that may have a lower alkylenedioxy group as a substituent on the phenyl ring, a morpholinocarbonyl-substituted lower alkyl group, or an imidazolyl lower alkanoyl group, R$^{13a}$ represents a hydrogen atom or a hydroxyl group, T represents a lower alkylene group, a group —N(R)—B$_3$—CO—, a group —B$_{19}$—N(R$^{18}$)—CO—, a group —B$_4$—CO—, a group -Q-B$_5$—CO—, a group —B$_6$—N(R$^{19}$)—B$_7$—CO—, a group —CO—B$_8$—, a group —CH(OH)—B$_9$—, a group —CO—B$_{10}$—CO—, a group —CH(OH)—B$_{11}$—CO—, a group —CO—, a group —SO$_2$—, or a group —B$_{23a}$—CO—CO—, wherein R$^{17}$ represents a hydrogen atom, a lower alkyl group, a cycloalkyl group, a cycloalkylcarbonyl group, a lower alkanoyl group that may have a halogen atom as a substituent, a lower alkenyl group, an amino-substituted lower alkanoyl group that may have a lower alkyl group as a substituent, or a lower alkylsulfonyl group, B$_3$ represents a lower alkylene group, B$_{19}$ represents a lower alkylene group, R$^{18}$ represents a hydrogen atom or a lower alkyl group, B$_4$ represents a lower alkenylene group or a lower alkylene group that may have a hydroxyl group as a substituent, Q represents an oxygen atom or a group —S(O)n- (wherein n is the same as described above), B$_5$ represents a lower alkylene group, B$_6$ represents a lower alkylene group, R$^{19}$ represents a hydrogen atom or a lower alkanoyl group, B$_7$ represents a lower alkylene group, B$_8$ represents a lower alkylene group, B$_9$ represents a lower alkylene group, B$_{10}$ represents a lower alkylene group, B$_{11}$ represents a lower alkylene group, B$_{23a}$ represents a lower alkylene group, l represents 0 or 1, R$^{14}$ represents a hydrogen atom or an alkyl group that may have a hydroxyl group as a substituent, R$^{15}$ represents (2) a hydroxyl group-substituted alkyl group, (3) a cycloalkyl group that may have a group selected from the group consisting of a hydroxyl group and a lower alkyl group as a substituent, (4) a phenoxy lower alkyl group, (5) a phenyl group that may be substituted, on the phenyl ring, by 1 to 3 groups selected from the group consisting of a lower alkyl group; a lower alkoxy group that may have a halogen atom as a substituent; a halogen atom; an amino lower alkoxy group that may have a lower alkyl group as a substituent; a hydroxyl group-substituted lower alkyl group; a phenyl lower alkyl group; a lower alkynyl group; an amino group that may have a lower alkylsulfonyl group as a substituent; a lower alkylthio group; a cycloalkyl group; a phenylthio group; an adamantyl group; an anilino group that may have a halogen atom as a substituent on the phenyl ring; a lower alkoxycarbonyl group; a piperazinyl group that may have a lower alkyl group as a substituent on the piperazine ring; a pyrrolidinyl group that may have an oxo group as a substituent on the pyrrolidine ring; a lower alkanoylamino group; a cyano group; and a phenoxy group, (6) a phenoxy group, (7) a phenyl lower alkyl group that may be substituted, on the phenyl ring, by 1 to 3 groups selected from the group consisting of a halogen atom, a lower alkoxy group that may have a halogen atom as a substituent, and a lower alkyl group, (8) a phenyl lower alkyl group that has a lower alkylenedioxy group as a substituent on the phenyl ring, (10) a lower alkoxycarbonyl-substituted lower alkyl group, (11) a carboxy-substituted lower alkyl group, (12) an amino group that may have a lower alkanoyl group as a substituent, (13) a 1,2,3,4-tetrahydroquinolyl group that may have 1 to 3 groups selected from the group consisting of an oxo group, a lower alkoxy group, and a lower alkylenedioxy group as a substituent(s) on the tetrahydroquinoline ring, (14) a cycloalkyl lower alkyl group, (15) a piperazinyl lower alkanoyl group that may be substituted, on the piperazine ring, by a phenyl lower alkyl group that may have a lower alkylenedioxy group as a substituent on the phenyl ring, (16) a pyridyl lower alkyl group, (17) an amino group-substituted lower alkyl group that may have a group selected from the group consisting of a lower alkyl group and a lower alkanoyl group as a substituent, (18) a lower alkoxy lower alkyl group, (19) an imidazolyl group, (20) an imidazolyl lower alkyl group, (21) a 1,2,3,4-tetrahydroisoquinolylcarbonyl-substituted lower alkyl group, (22) a piperidinylcarbonyl group that may have a group selected from the group consisting of a lower alkoxycarbonyl group, a phenyl lower alkyl group, and a furyl lower alkyl group as a substituent on the piperidine ring, (23) a thiazolidinyl lower alkanoyl group that may have an oxo group as a substituent on the thiazolidine ring, (24) a piperidinyl group that may be substituted, on the piperidine ring, by a group selected from the group consisting of a lower alkoxycarbonyl group, a phenyl lower alkyl group, a lower alkyl group, a benzoyl group, and a furyl lower alkyl group, (25) a carbonyl lower alkyl group substituted by a group

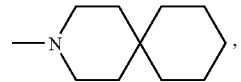

[Formula 24]

(26) a carbonyl lower alkyl group substituted by a group

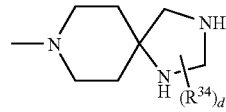

[Formula 25]

(27) a group —CO—B$_{20}$—N(R$^{36}$)R$^{37}$, (26a) a pyrrolidinyl lower alkyl group, (27a) a morpholino lower alkyl group, (28a) a phenyl lower alkenyl group, (29a) an anilinocarbonyl lower alkyl group that may have a lower alkyl group as a substituent on the phenyl ring, (30a) an indolyl group, (31a) a piperazinyl lower alkyl group that may have, as a substituent on the piperazine ring, a group selected from the group consisting of a lower alkyl group and a phenyl lower alkyl group that may have a lower alkylenedioxy group as a substituent on the phenyl ring, (32a) an amidino lower alkyl group that may have a lower alkyl group as a substituent, (33a) a fluorenyl group, (34a) a carbazolyl group that may have a lower alkyl group as a substituent on the carbazole ring, (35a) an amidino group that may have a lower alkyl group as a substituent, (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, or (37a) a cyano-substituted lower alkyl group, $R^{34}$ represents an oxo group or a phenyl group, d represents an integer from 0 to 3, $B_{20}$ represents a lower alkylene group, $R^{36}$ and $R^{37}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 phenyl lower alkyl groups that may have a lower alkylenedioxy group on the phenyl ring, may be present as a substituent(s), $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring; or a group

[Formula 26]

wherein, on the heterocyclic ring, 1 to 3 substituents may be present which are selected from the group consisting of (28) a phenyl-substituted lower alkyl group, which has 1 to 2 phenyl groups that may be substituted by 1 to 3 groups on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group, and that may have a pyridyl group on the lower alkyl group, (29) a carbamoyl group, (30) a pyridyl lower alkyl group that may have, as a substituent(s) on the pyridine ring, 1 to 3 groups selected from the group consisting of a hydroxyl group and a lower alkyl group that may have a hydroxyl group as a substituent, (31) a pyrrolyl lower alkyl group that may have 1 to 3 lower alkyl groups as a substituent(s) on the pyrrole ring, (32) a benzoxazolyl lower alkyl group, (33) a benzothiazolyl lower alkyl group, (34) a furyl lower alkyl group, (35) a benzoyl group that may be substituted, on the phenyl ring, by 1 to 3 groups selected from the group consisting of a cyano group, an amino group that may have a lower alkylsulfonyl group as a substituent, a halogen atom, a lower alkoxy group, a lower alkyl group that may have a halogen atom as a substituent, a thiazolidinyl lower alkyl group that may have an oxo group as a substituent on the thiazolidine ring, a thiazolidinylidene lower alkyl group that may have an oxo group as a substituent on the thiazolidine ring, and a lower alkylenedioxy group, (36) a pyrimidinyl group, (37) a pyrazinyl group, (38) a pyridyl group, (39) a lower alkoxycarbonyl group, (40) a thiazo-lidinyl lower alkanoyl group that may be substituted, on the thiazolidine ring, by a group selected from the group consisting of an oxo group and a group

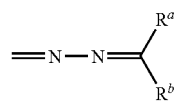

[Formula 27]

(wherein $R^a$ and $R^b$ each represent a lower alkyl group), (41) a lower alkyl group that may have a group selected from the group consisting of a hydroxyl group and a halogen atom as a substituent, (42) a lower alkanoyl group that may have a halogen atom as a substituent, (43) a phenyl group that may be substituted, on the phenyl ring, by 1 to 3 groups selected from the group consisting of a carbamoyl group that may have a group selected from the group consisting of a lower alkoxy lower alkyl group and a lower alkyl group, a lower alkoxycarbonyl group, a carboxy group, a cyano group, a phenyl group, a halogen atom, a lower alkyl group that may have a halogen atom as a substituent, a lower alkoxy group that may have a halogen atom as a substituent, a benzoyl group that may have a halogen atom as a substituent on the phenyl ring, a phenyl lower alkyl group that may have a halogen atom as a substituent on the phenyl ring, and a hydroxyl group, (44) a phenyl group that may have a lower alkylenedioxy group as a substituent on the phenyl ring, (45) a naphthyl lower alkyl group, (46) a phenoxy group that may be substituted, on the phenyl ring, by 1 to 3 groups selected from the group consisting of a cyano group, a lower alkyl group that may have a halogen atom as a substituent, and a lower alkoxy group that may have a halogen atom as a substituent, (47) a phenoxy lower alkyl group, (48) a phenyl lower alkoxy group that may be substituted, on the phenyl ring, by 1 to 3 groups selected from the group consisting of a halogen atom, a lower alkyl group that may have a halogen atom as a substituent, and a lower alkoxy group that may have a halogen atom as a substituent, (49) a group —($B_{12}$CO)t-N($R^{20}$)$R^{21}$, (50) a group —(CO)o-$B_{13}$—N($R^{22}$)$R^{23}$, (51) a 1,2,3,4-tetrahydronaphthyl-substituted lower alkyl group that may be substituted, on the 1,2,3,4-tetrahydronaphthalene ring, by 1 to 5 lower alkyl groups as a substituent(s), (52) a cycloalkyl group that may have a hydroxyl group as a substituent, (53) a piperidinyl group that may be substituted, on the piperidine ring, by 1 to 3 lower alkyl groups as a substituent(s), (54) a quinolyl lower alkyl group, (55) a 1,2,3,4-tetrazolyl lower alkyl group that may have a group selected from the group consisting of a lower alkyl group and a phenyl lower alkyl group as a substituent on the tetrazole ring, (56) a thiazolyl lower alkyl group that may have a phenyl group as a substituent on the thiazole ring, (57) a benzoyl lower alkyl group that may have 1 to 3 groups selected from the group consisting of a lower alkoxy group and a halogen atom as a substituent(s) on the phenyl ring, (58) a piperidinyl lower alkyl group that may have a lower alkyl group as a substituent on the piperidine ring, (59) an imidazolyl group that may have 1 to 3 phenyl groups as a substituent(s) on the imidazole ring, (60) a benzimidazolyl group that may have 1 to 3 lower alkyl groups as a substituent(s) on the benzimidazole ring, (61) a pyridyl lower alkoxy group, (62) a 1,2,3,4-tetrahydroquinolyl lower alkyl group that may have an oxo group as a substituent on the tetrahydroquinoline ring, (63) a 1,3,4-oxadiazolyl lower alkyl group that may have an oxo group as a substituent on the 1,3,4-oxadizole ring, (64) a cycloalkyl lower alkyl group, (65) a tetrahydropyranyl group, (66) a thienyl lower alkyl group, (67) a pyrimidinylcarbonyl group that may have an oxo group as a substituent on the pyrimidine ring, (68) a hydroxyl group, (69) a carboxy group, (70) a lower alkoxy lower alkyl group, (71) a lower alkoxy lower alkoxy group, (72) a benzoyloxy group, (73) a lower alkoxycarbonyl lower alkoxy group, (74) a carboxy lower alkoxy group, (75) a phenoxy lower alkanoyl group, (76) a 1,2,3,4-tetrahydroquinolylcarbonyl group that may have an oxo group as a substituent on the tetrahydroquinoline ring, (77) a phenylsulfonyl group, (78) an imidazolyl lower alkanoyl group, (79) an imidazolyl lower alkyl group, (80) a pyridylcarbonyl group, (81) an imidazolylcarbonyl group, (82) a lower alkoxycarbonyl lower alkyl group, (83) a carboxy lower alkyl group, (84) a group —(O—$B_{15}$)s-CO—N($R^{26}$)$R^{27}$, (85) a group —N($R^{28}$)—CO—$B_{16}$—N($R^{29}$)$R^{30}$, (86) a group —N(R″)—$B_{17}$—CO—N($R^{32}$)$R^{33}$, (87) a benzoxazolyl group, (88a) a benzothienyl group, (89a) an oxo group, and (90a) a 1,2,3,4-tetrahydroquinolyl group that may have an oxo group as a substituent on the tetrahydroquinoline ring, $B_{12}$ represents a lower alkylene group, t represents 0 or 1, $R^{20}$ and $R^{21}$ may be identical or different and each represent a hydrogen atom; an amino group that may have a lower alkoxycarbonyl group as a substituent; a benzoyl group that may have 1 to 3 lower alkoxy groups as a substituent(s) on the phenyl ring; a lower alkyl group; a lower alkyl group having 1 to 2 phenyl groups that may be substituted, on the phenyl ring, by 1 to 3 groups selected from the group consisting of a lower alkoxycarbonyl group, a cyano group, a nitro group, a phenyl group, a halogen atom, a lower alkyl group that may have a halogen atom as a substituent, a lower alkoxy group that may have a halogen atom as a substituent, and a lower alkylthio group; a phenyl group that may be substituted, on the phenyl ring, by 1 to 3 groups selected from the group consisting of a lower alkoxy group that may have a halogen atom as a substituent and a lower alkyl group that may have a halogen atom as a substituent; a lower alkoxycarbonyl group; a cycloalkyl lower alkyl group; a pyrrolidinyl lower alkyl group that may have 1 to 3 lower alkyl groups that may have a hydroxyl group as a substituent on the pyrrolidine ring; an amino-substituted lower alkyl group that may have a group selected from the group consisting of a phenyl group and a lower alkyl group as a substituent; a 1,2,3,4-tetrahydronaphthyl-substituted lower alkyl group that may have 1 to 5 lower alkyl groups as a substituent(s) on the 1,2,3,4-tetrahydronaphthalene ring; a naphthyl lower alkyl group; a pyridyl lower alkyl group; a quinolyl lower alkyl group; a 1,2,3,4-tetrazolyl lower alkyl group that may have 1 to 3 groups selected from the group consisting of a lower alkyl group and a phenyl lower alkyl group as a substituent(s) on the tetrazole ring; a 1,2,4-triazolyl lower alkyl group; a tetrahydrofuryl lower alkyl group that may have a hydroxyl group as a substituent on the lower alkyl group; a phenoxy lower alkyl group that may have 1 to 3 groups selected from the group consisting of a lower alkyl group and a nitro group as a substituent(s) on the phenyl ring; a phenyl lower alkanoyl group; a lower alkanoyl group that may have a halogen atom as a substituent; an imidazolyl lower alkanoyl group; a lower alkoxycarbonyl lower alkyl group; a pyridyl group; or a carboxy lower alkyl group, or a cycloalkyl group; and $R^{20}$ and $R^{21}$, together with the nitrogen atom to which they bind, may bind to each other, directly or via a nitrogen atom, oxygen atom, or sulfur atom to form a 5- to 7-membered saturated heterocyclic ring(wherein, on the heterocyclic ring, 1 to 3 substituents may be present, which are selected from the group consisting of a lower alkyl group, a phenyl group that may have 1 to 3 groups selected from the group consisting of a halogen atom and a lower alkyl group that may have a halogen atom as a substituent(s) on the phenyl ring, and a phenyl lower alkyl group that may have a lower alkylenedioxy group as a substituent on the phenyl ring), o represents 0 or 1, $B_{13}$ represents a lower alkylene group, $R^{22}$ and $R^{23}$ may be identical or different and each represent a hydrogen atom, a lower alkyl group, a benzoyl group that may have 1 to 3 lower alkoxy groups as a substituent(s) on the phenyl ring, a phenoxy lower alkyl group that may have a lower alkyl group as a substituent on the phenyl ring, a phenyl lower alkyl group, or a phenyl group, or $R^{22}$ and $R^{23}$, together with the nitrogen atom to which they bind, may bind to each other, directly or via a nitrogen atom, oxygen atom, or sulfur atom to form a 5- to 7-membered saturated heterocyclic ring (wherein, on the heterocyclic ring, 1 to 3 substituents may be present, which are selected from the group consisting of a lower alkyl group and a phenyl lower alkyl group that may have a lower alkylenedioxy group as a substituent on the phenyl ring), $B_{15}$ represents a lower alkylene group, s represents 0 or 1, $R^{26}$ and $R^{27}$ may be identical or different and each represent a hydrogen atom, a lower alkyl group, a phenyl lower alkyl group, or an imidazolyl lower alkyl group, and $R^{26}$ and $R^{27}$, together with the nitrogen atom to which they bind, may bind to each other, directly or via a nitrogen atom, oxygen atom, or sulfur atom to form a 5- to 7-membered saturated heterocyclic ring, (wherein, on the heterocyclic ring, 1 to 3 phenyl lower alkyl groups that may have a lower alkylenedioxy group as a substituent, may be present on the phenyl ring, as a substituent(s)), $R^{28}$ represents a hydrogen atom or a lower alkyl group, $B_{16}$ represents a lower alkylene group, $R^{29}$ and $R^{30}$, together with the nitrogen atom to which they bind, may bind to each other, directly or via a nitrogen atom, oxygen atom, or sulfur atom to form a 5- to 7-membered saturated heterocyclic group, wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring, $R^{31}$ represents a hydrogen atom or a lower alkyl group, $B_{17}$ represents a lower alkylene group, $R^{32}$ and $R^{33}$, together with the nitrogen atom to which they bind, may bind to each other, directly or via a nitrogen atom, oxygen atom, or sulfur atom to form a 5- to 7-membered saturated heterocyclic group, (wherein, on the heterocyclic ring, 1 to 3 substituents may be present, which are selected from the group consisting of a lower alkyl group, a phenyl group, and a phenyl lower alkyl group that may have a lower alkylenedioxy group as a substituent on the phenyl ring).

However, that the aforementioned compound or a salt thereof satisfies the following requirements (i) to (v):

(i) when $X_1$ represents a group —CH═, then $R^3$ represents a hydrogen atom;

(ii) when $X_1$ represents a group —CH═, 1 represents 1, T represents —CO—, and $R^{14}$ represents a hydrogen atom or an alkyl group that may have a hydroxyl group as a substituent, $R^{15}$ represents the group (24);

(iii) when $X_1$ represents a group —CH=, l represents 1, and T represents —N($R^{17}$)—$B_3$—CO—, $R^{14}$ and $R^{15}$, together with the nitrogen atom to which they bind, may bind to each other, directly or via a nitrogen atom, oxygen atom, or sulfur atom to form a 5- to 10-membered saturated or unsaturated heterocyclic ring, wherein, on the heterocyclic ring, 1 to 3 groups of (28) are present as a substituent(s);

(iv) when $X_1$ represents a nitrogen atom, and l represents 0, or when $X_1$ represents a nitrogen atom, l represents 1, and T represents —CO— or —SO$_2$, $R^{15}$ is not a group (5), (7), (19), or (20); and (v) when $R^6$ represents a cycloalkyl group that may have on the cycloalkyl ring, a substituent selected from the group consisting of an amino-substituted lower alkyl group that may have a lower alkyl group and a lower alkyl group that may have a halogen atom as a substituent, $R^4$ represents a group -(T)$_l$-N($R^{14}$)$R^{15}$ (wherein T and l are the same as described above, and $R^{14}$ and $R^{15}$, together with the nitrogen atom to which they bind, may bind to each other, directly or via a nitrogen atom, oxygen atom, or sulfur atom to form a 5- to 10-membered saturated heterocyclic ring; or $R^{14}$ and $R^{15}$ form a group

[Formula 28]

Item 2: The aromatic compound or a salt thereof according to item 1, comprising a compound selected from the group consisting of the compounds represented by the general formulas (1-1) to (1-7) below or a salt thereof as an active ingredient:

[Formula 29]

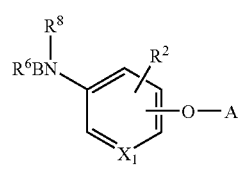 (1-1)

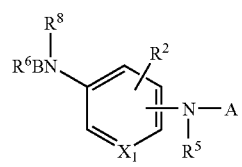 (1-2)

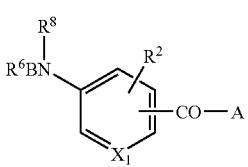 (1-3)

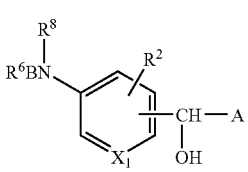 (1-4)

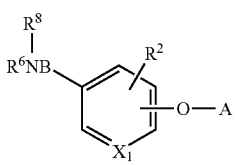 (1-5)

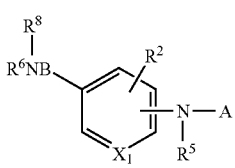 (1-6)

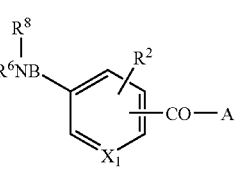 (1-7)

wherein $Y_3$ represents a lower alkylene group.

Item 3: The aromatic compound or a salt thereof according to item 1, comprising a compound selected from the group consisting of the compounds represented by the general formulas (1-8) to (1-14) below or a salt thereof as an active ingredient:

[Formula 30]

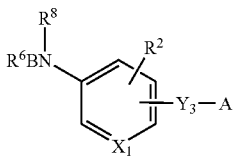 (1-8)

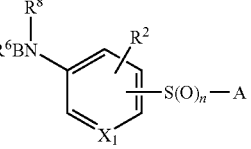 (1-9)

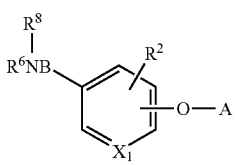 (1-10)

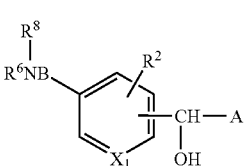 (1-11)

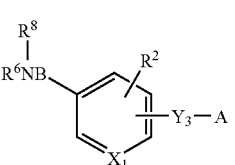 (1-12)

-continued

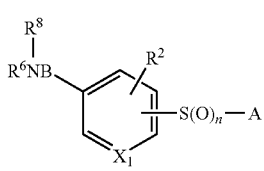
(1-13)

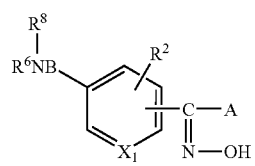
(1-14)

wherein Y₃ represents a lower alkylene group.

Item 4: The aromatic compound or a salt thereof according to item 1, comprising a compound selected from the group consisting of the compounds represented by the general formulas (1-15) to (1-21) below or a salt thereof as an active ingredient:

[Formula 31]

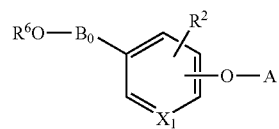
(1-15)

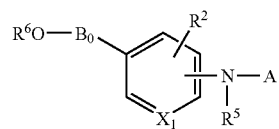
(1-16)

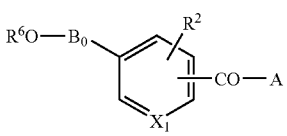
(1-17)

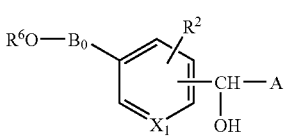
(1-18)

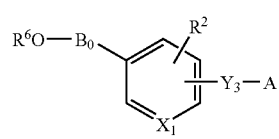
(1-19)

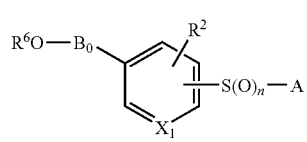
(1-20)

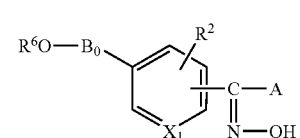
(1-21)

wherein Y₃ represents a lower alkylene group.

Item 5: The aromatic compound or a salt thereof according to item 1, comprising a compound selected from the group consisting of the compounds represented by the general formulas (1-22) to (1-28) below or a salt thereof as an active ingredient:

[Formula 32]

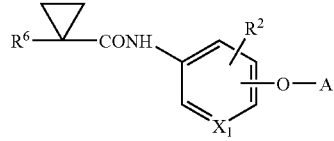
(1-22)

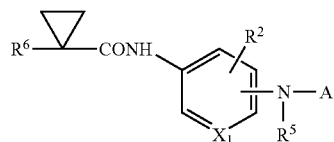
(1-23)

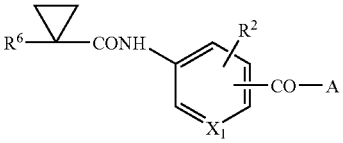
(1-24)

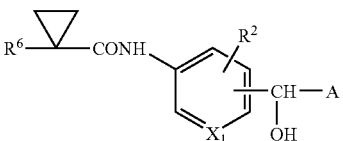
(1-25)

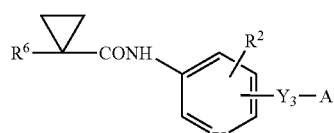
(1-26)

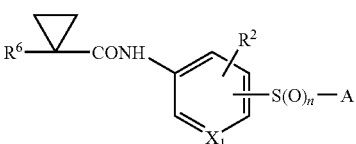
(1-27)

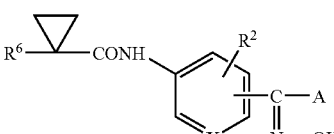
(1-28)

wherein Y₃ represents a lower alkylene group.

Item 6: The aromatic compound or a salt thereof according to item 1, comprising a compound selected from the group consisting of the compounds represented by the general formulas (1-29) to (1-35) below or a salt thereof as an active ingredient:

[Formula 33]

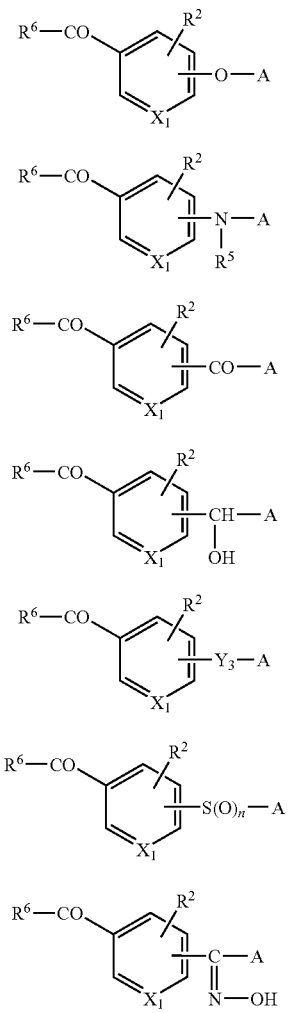

wherein $Y_3$ represents a lower alkylene group.

Item 7: The aromatic compound or a salt thereof according to item 1, comprising a compound selected from the group consisting of the compounds represented by the general formulas (1-36) to (1-42) below or a salt thereof as an active ingredient:

[Formula 34]

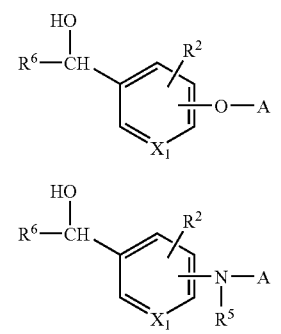

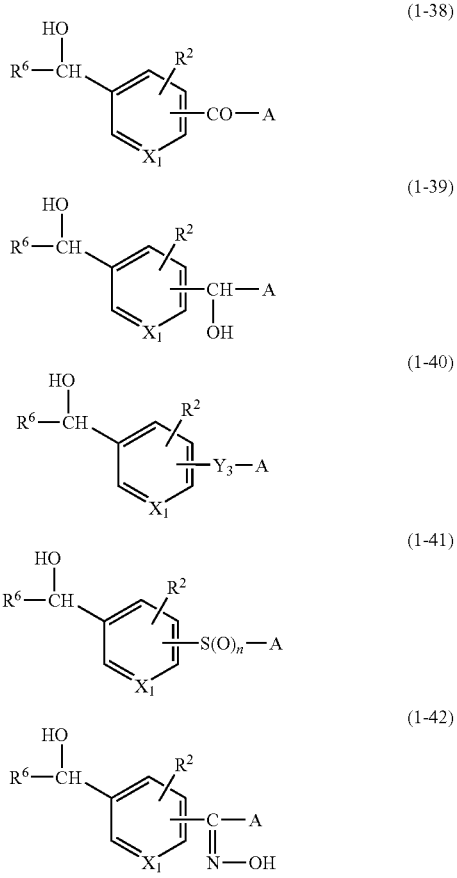

wherein $Y_3$ represents a lower alkylene group.

Item 8: The aromatic compound or a salt thereof according to item 1, comprising a compound selected from the group consisting of the compounds represented by the general formulas (1-43) to (1-49) below or a salt thereof as an active ingredient:

[Formula 35]

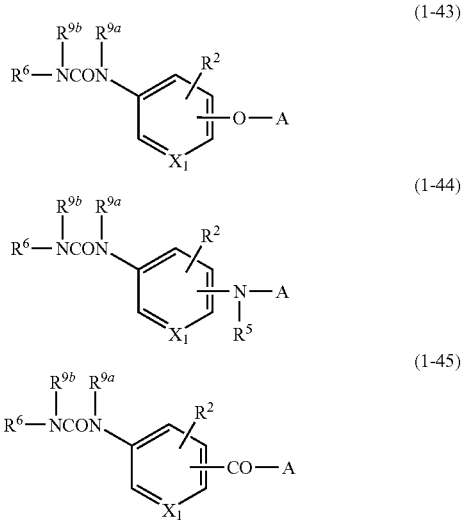

(1-46)
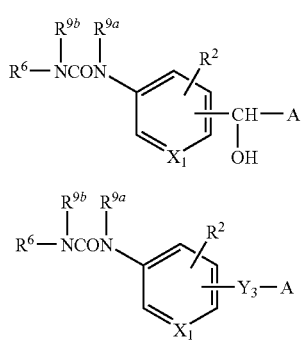

(1-47)
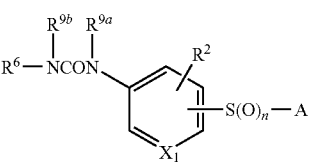

(1-48)
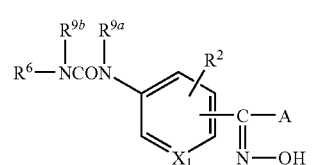

(1-49)
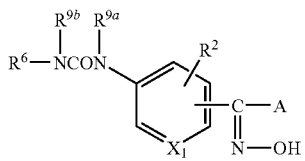

wherein Y₃ represents a lower alkylene group.

Item 9: The aromatic compound or a salt thereof according to item 1, comprising a compound selected from the group consisting of the compounds represented by the general formulas (1-50) to (1-56) below or a salt thereof as an active ingredient:

[Formula 36]

(1-50)
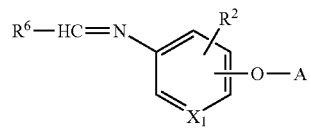

(1-51)
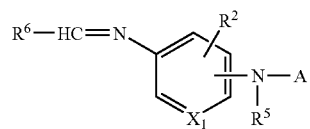

(1-52)
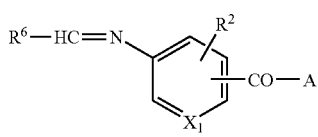

(1-53)
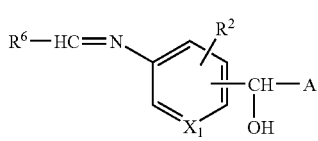

(1-54)
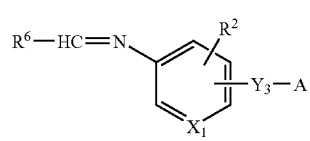

(1-55)
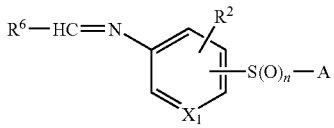

(1-56)
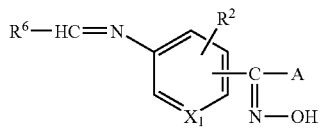

wherein Y₃ represents a lower alkylene group.

Item 10: The aromatic compound or a salt thereof according to item 1, comprising a compound selected from the group consisting of the compounds represented by the general formulas (1-57) to (1-63) below or a salt thereof as an active ingredient:

[Formula 37]

(1-57)
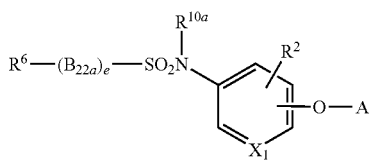

(1-58)
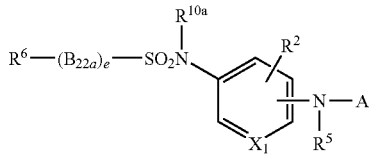

(1-59)
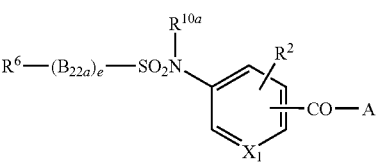

(1-60)
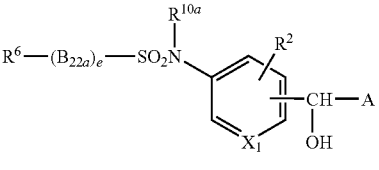

(1-61)
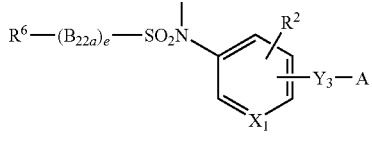

(1-62)
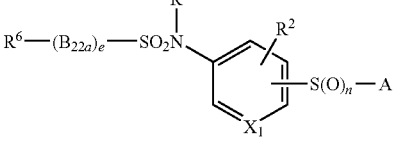

-continued

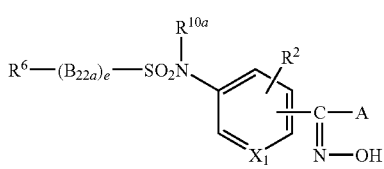 (1-63)

wherein Y₃ represents a lower alkylene group.

Item 11: The aromatic compound or a salt thereof according to item 1, comprising a compound selected from the group consisting of the compounds represented by the general formulas (1-64) to (1-70) below or a salt thereof as an active ingredient:

[Formula 38]

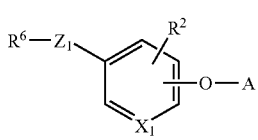 (1-64)

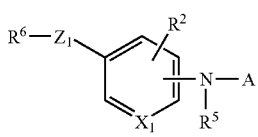 (1-65)

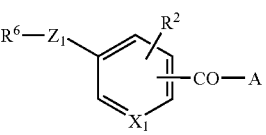 (1-66)

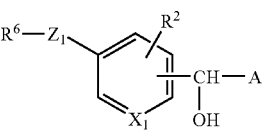 (1-67)

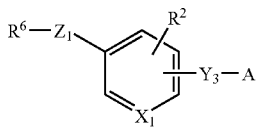 (1-68)

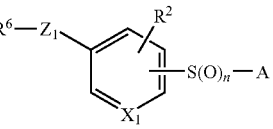 (1-69)

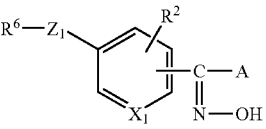 (1-70)

wherein Y₃ represents a lower alkylene group, and $Z_1$ represents a lower alkenylene group.

Item 12: The aromatic compound or a salt thereof according to item 1, comprising a compound selected from the group consisting of the compounds represented by the general formulas (1-71) to (1-77) below or a salt thereof as an active ingredient:

[Formula 39]

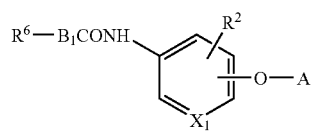 (1-71)

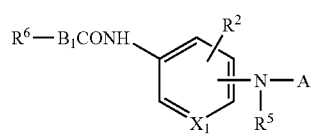 (1-72)

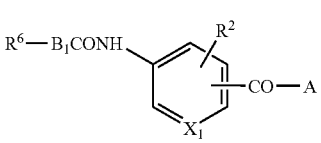 (1-73)

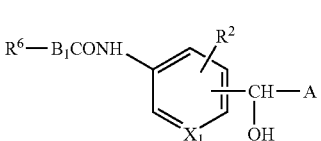 (1-74)

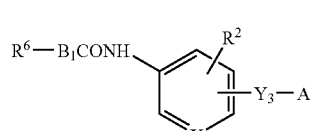 (1-75)

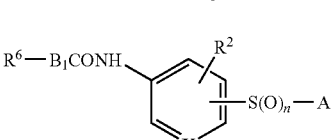 (1-76)

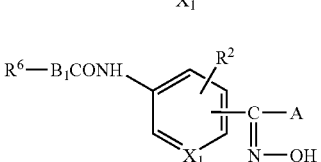 (1-77)

wherein Y₃ represents a lower alkylene group.

Item 13: The aromatic compound or a salt thereof according to item 1, comprising a compound selected from the group consisting of the compounds represented by the general formulas (1-78) to (1-84) below or a salt thereof as an active ingredient:

[Formula 40]

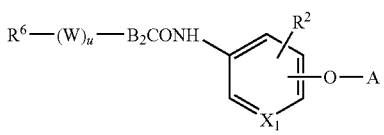 (1-78)

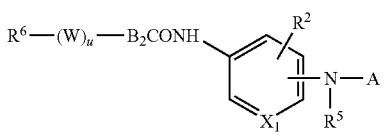 (1-79)

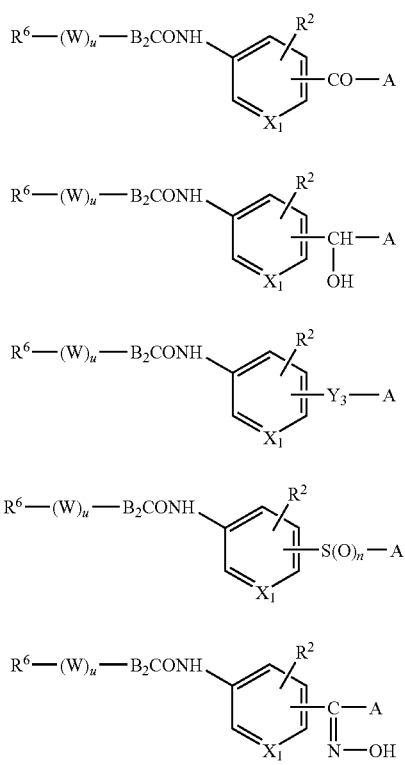

wherein $Y_3$ represents a lower alkylene group.

Item 14: The aromatic compound or a salt thereof according to item 1, comprising a compound selected from the group consisting of the compounds represented by the general formulas (1-85) to (1-91) below or a salt thereof as an active ingredient:

[Formula 41]

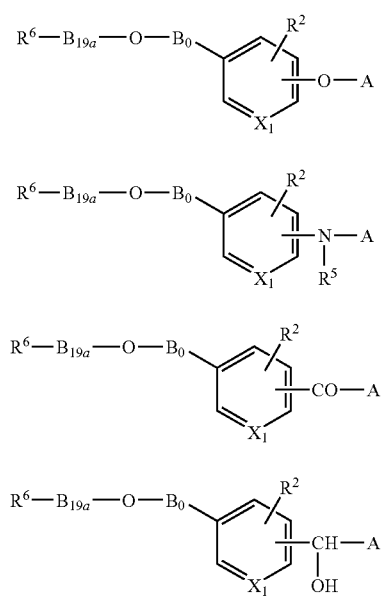

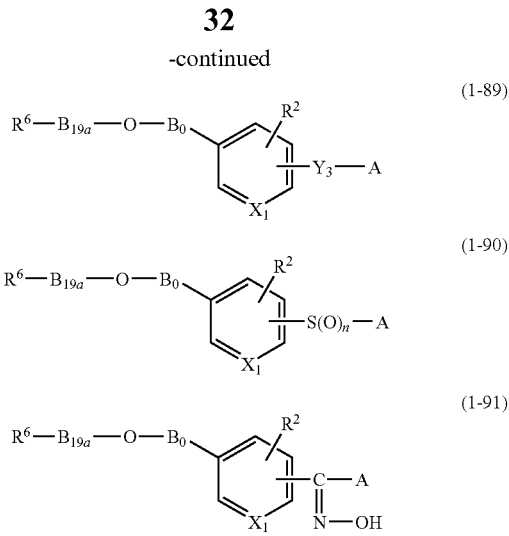

wherein $Y_3$ represents a lower alkylene group.

Item 15: The aromatic compound or a salt thereof according to item 1, comprising a compound selected from the group consisting of the compounds represented by the general formulas (1-92) to (1-98) below or a salt thereof as an active ingredient:

[Formula 42]

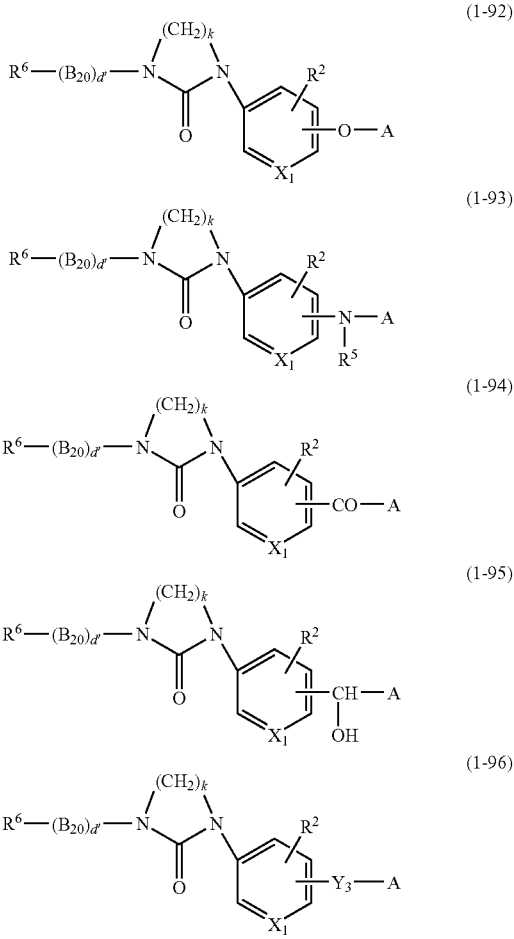

-continued

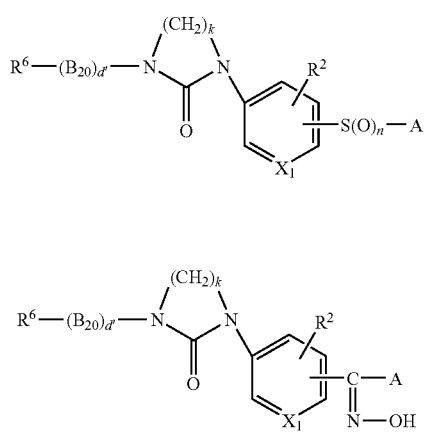

wherein Y₃ represents a lower alkylene group.

Item 16: The aromatic compound or a salt thereof according to item 1, comprising a compound selected from the group consisting of the compounds represented by the general formulas (1-99) to (1-105) below or a salt thereof as an active ingredient:

[Formula 43]

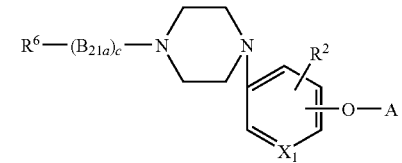

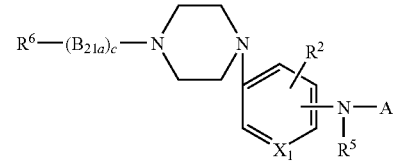

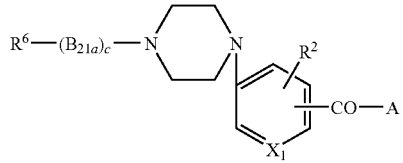

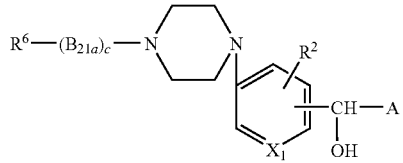

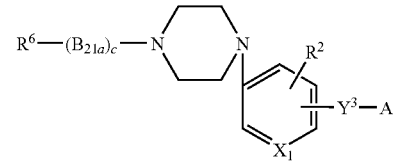

-continued

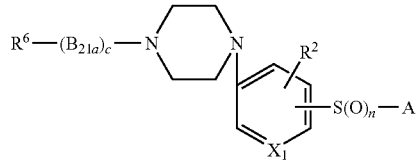

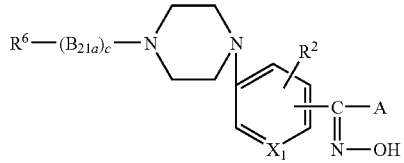

wherein Y₃ represents a lower alkylene group.

Item 17: The aromatic compound or a salt thereof according to item 1, comprising a compound selected from the group consisting of the compounds represented by the general formulas (1-106) to (1-112) below or a salt thereof as an active ingredient:

[Formula 44]

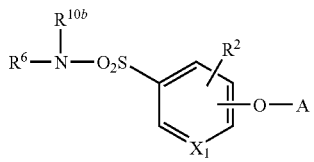

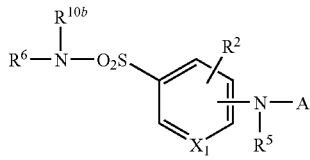

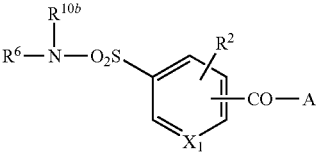

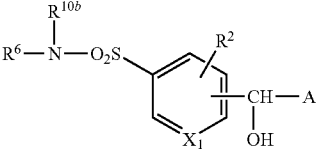

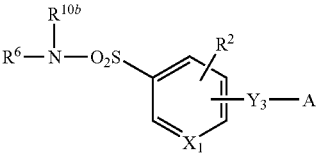

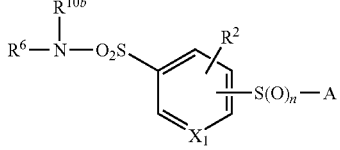

-continued

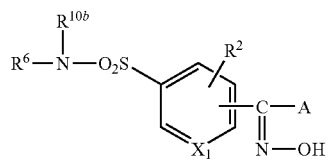
(1-112)

wherein Y₃ represents a lower alkylene group.

Item 18: The aromatic compound or a salt thereof according to item 1, comprising a compound selected from the group consisting of the compounds represented by the general formulas (1-113) to (1-119) below or a salt thereof as an active ingredient:

[Formula 45]

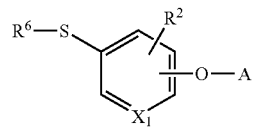
(1-113)

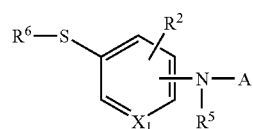
(1-114)

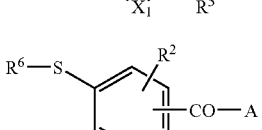
(1-115)

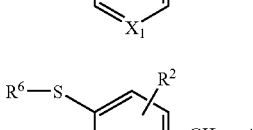
(1-116)

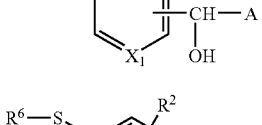
(1-117)

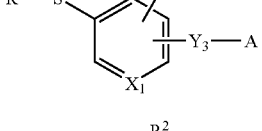
(1-118)

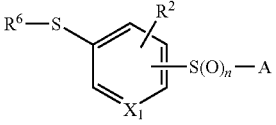
(1-119)

wherein Y₃ represents a lower alkylene group.

Item 19: The aromatic compound or a salt thereof according to item 1, comprising a compound selected from the group consisting of the compounds represented by the general formulas (1-120) to (1-126) below or a salt thereof as an active ingredient:

[Formula 46]

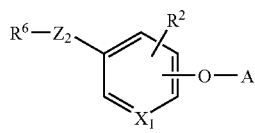
(1-120)

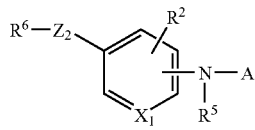
(1-121)

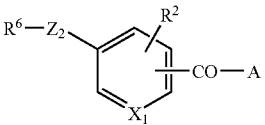
(1-122)

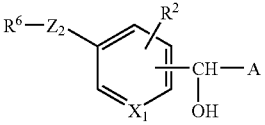
(1-123)

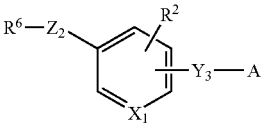
(1-124)

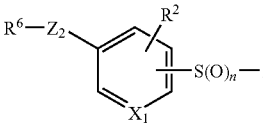
(1-125)

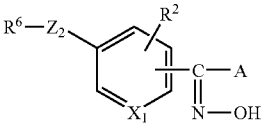
(1-126)

wherein Y₃ represents a lower alkylene group, and Z₂ represents a lower alkynylene group.

Item 20: The aromatic compound or a salt thereof according to item 1, comprising a compound selected from the group consisting of the compounds represented by the general formulas (1-127) to (1-133) below or a salt thereof as an active ingredient:

[Formula 47]

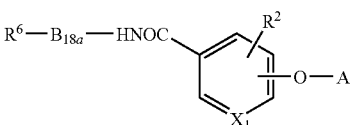
(1-127)

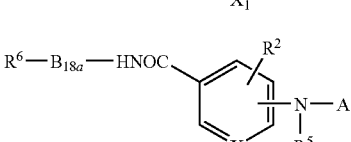
(1-128)

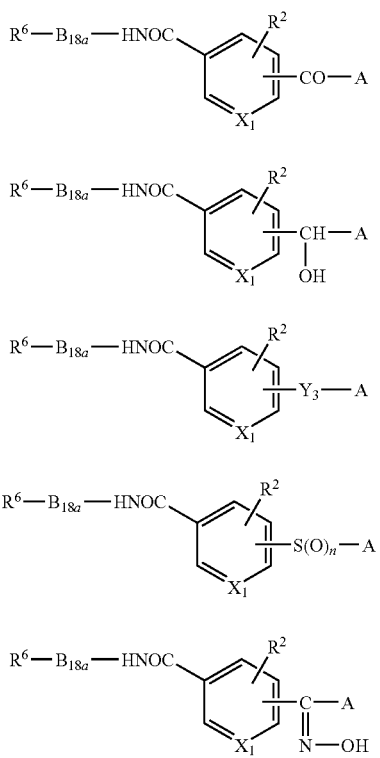

(1-129)
(1-130)
(1-131)
(1-132)
(1-133)

wherein $Y_3$ represents a lower alkylene group.

Item 21: The aromatic compound or a salt thereof according to item 1, comprising a compound selected from the group consisting of the compounds represented by the general formulas (1-134) to (1-140) below or a salt thereof as an active ingredient:

[Formula 48]

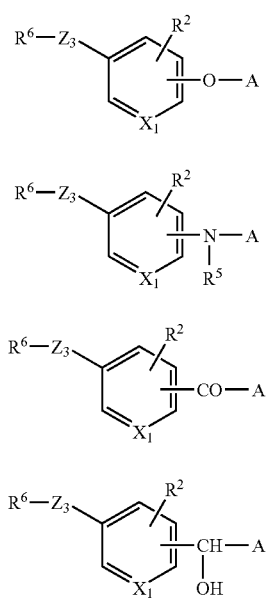

(1-134)
(1-135)
(1-136)
(1-137)

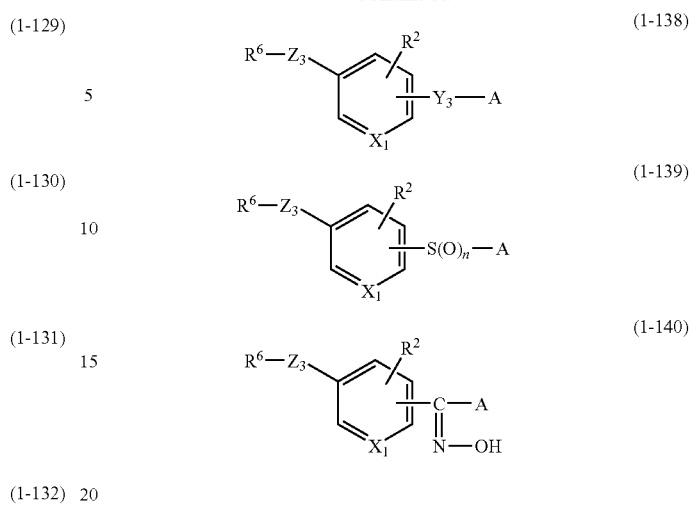

(1-138)
(1-139)
(1-140)

wherein $Y_3$ represents a lower alkylene group, and $Z_3$ represents a lower alkylene group or a group $—N(R^{8d})—$.

Item 22: The aromatic compound or a salt thereof according to any one of items 1 to 21, wherein Y is a group —O—.

Item 23: The aromatic compound or a salt thereof according to any one of items 1 to 21, wherein Y is a group $—N(R^5)—$.

Item 24: The aromatic compound or a salt thereof according to any one of items 1 to 21, wherein Y is a group —CO—, a group —CH(OH)—, a lower alkylene group, a group —S(O)n-, or a group —C(=N—OH)—.

Item 25: The aromatic compound or a salt thereof according to any one of items 1 to 21, wherein A is a group

[Formula 49]

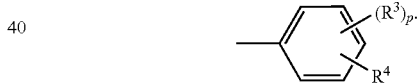

Item 26: The aromatic compound or a salt thereof according to any one of items 1 to 21, wherein A is a group

[Formula 50]

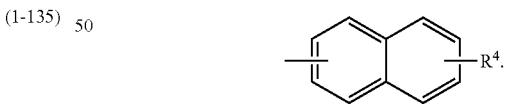

Item 27: The aromatic compound or a salt thereof according to any one of items 1 to 21, wherein $R^4$ represents an imidazolyl lower alkyl group, a 1,2,4-triazolyl lower alkyl group, a 1,2,3-triazolyl lower alkyl group, a 1,2,5-triazolyl lower alkyl group, a pyrazolyl lower alkyl group, a pyrimidinyl lower alkyl group that may have an oxo group as a substituent on the pyrimidine ring, a 3,5-dioxoisoxazolidin-4-ylidene lower alkyl group, a 1,2,4-oxadiazolyl lower alkyl group that may have a lower alkyl group as a substituent on the 1,2,4-oxadiazole ring, a thiazolidinyl lower alkyl group that may have an oxo group as a substituent on the thiazolidine ring, a group

[Formula 51]

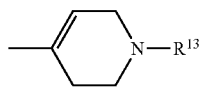

or a group

[Formula 52]

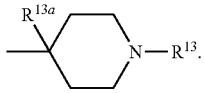

Item 28: The aromatic compound or a salt thereof according to any one of items 1 to 21, represented by the general formula (1) wherein $R^4$ represents a group $-(T)_1-N(R^{14})R^{15}$ (T, $R^{14}$, and $R^{15}$ are the same as defined above) and l represents 0.

Item 29: The aromatic compound or a salt thereof according to any one of items 1 to 21, wherein $R^4$ is a group $-(T)_1-N(R^{14})R^{15}$, and l is 1.

Item 30: The aromatic compound or a salt thereof according to any one of items 1 to 21, wherein $R^4$ is a group $-(T)_1-N(R^{14})R^{15}$, l is 1, and T is a group $—N(R^{17})—B_3—CO—$.

Item 31: The aromatic compound or a salt thereof according to any one of items 1 to 21, wherein $R^4$ is a group $-(T)_1-N(R^{14})R^{15}$, l is 1, and T is a group $—B_{19}—N(R^{18})—CO—$.

Item 32: The aromatic compound or a salt thereof according to any one of items 1 to 21, wherein $R^4$ is a group $-(T)_1-N(R^{14})R^{15}$, l is 1, and T is a group $—B_4—CO—$.

Item 33: The aromatic compound or a salt thereof according to any one of items 1 to 21, wherein $R^4$ is a group $-(T)_1-N(R^{14})R^{15}$, l is 1, and T is a group $-Q-B_5—CO—$.

Item 34: The aromatic compound or a salt thereof according to any one of items 1 to 21, wherein $R^4$ is a group $-(T)_1-N(R^{14})R^{15}$, l is 1, and T is a group $—B_6—N(R^{19})—B_7—$.

Item 35: The aromatic compound or a salt thereof according to any one of items 1 to 21, wherein $R^4$ is a group $-(T)_1-N(R^{14})R^{15}$, l is 1, and T is a group $—CO—B_8—$.

Item 36: The aromatic compound or a salt thereof according to any one of Items 1 to 21, wherein $R^4$ is a group $-(T)_1-N(R^{14})R^{15}$, l is 1, and T is a group $—CH(OH)—B_9—$.

Item 37: The aromatic compound or a salt thereof according to any one of items 1 to 21, wherein $R^4$ is a group $-(T)_1-N(R^{14})R^{15}$, l is 1, and T is a group $—CO—B_{10}—CO—$.

Item 38: The aromatic compound or a salt thereof according to any one of items 1 to 21, wherein $R^4$ is a group $-(T)_1-N(R^{14})R^{15}$, l is 1, and T is a group $—CH(OH)—B_{11}—CO—$.

Item 39: The aromatic compound or a salt thereof according to any one of items 1 to 21, wherein $R^4$ is a group $-(T)_1-N(R^{14})R^{15}$, l is 1, and T is a group $—CO—$.

Item 40: The aromatic compound or a salt thereof according to any one of items 1 to 21, wherein $R^4$ is a group $-(T)_1-N(R^{14})R^{15}$, l is 1, and T is a group $—SO_2—$.

Item 41: The aromatic compound or a salt thereof according to any one of items 1 to 21, wherein $R^4$ is a group $-(T)_1-N(R^{14})R^{15}$, l is 1, and T is a group $—B_{23a}—CO—CO—$.

Item 42: The aromatic compound or a salt thereof according to any one of items 1 to 21, wherein $R^4$ is a group $-(T)_1-N(R^{14})R^{15}$, l is 1, and T is a lower alkylene group.

Item 43: The aromatic compound or a salt thereof according to item 1, comprising a compound selected from the group consisting of the compounds represented by the general formulas (1-1), (1-2), (1-8), (1-9), (1-15), (1-16), (1-29), (1-30), (1-43), (1-44), (1-57), (1-58), (1-64) and (1-65) or a salt thereof as an active ingredient, wherein Y is a group —O- or a group $—N(R^5)—$, A is a group

[Formula 53]

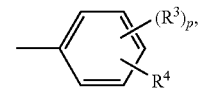

and
$R^4$ is a group $-(T)_1-N(R^{14})R^{15}$.

Item 44: The aromatic compound or a salt thereof according to item 43, wherein l is 1, and T is a group $—N(R^{17})—B_3—CO—$.

Item 45: The aromatic compound or a salt thereof according to item 43, wherein l is 1, and T is a group $—B_4—CO—$.

Item 46: The aromatic compound or a salt thereof according to item 43, wherein l is 1, and T is a group $—CO—$.

Item 47: The aromatic compound or a salt thereof according to item 43, wherein l is 0.

Item 48: The aromatic compound or a salt thereof according to item 1, comprising a compound selected from the group consisting of N-[6-(4-{[2-(4-piperonylpiperazin-1-yl)-2-oxoethyl]ethylamino}-2-methoxyphenoxy)pyridin-3-yl]-3,4-dichlorobenzamide, N-[6-(4-{[2-(4-piperonylpiperazin-1-yl)-2-oxoethyl]ethylamino}phenoxy)pyridin-3-yl]-4-trifluoromethylbenzamide, N-[6-(4-{[2-(4-piperonylpiperazin-1-yl)-2-oxoethyl]ethylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-fluorophenoxy)pyridin-3-yl]-4-trifluoromethylbenzamide, N-[6-(4-{[2-(4-piperonylpiperazin-1-yl)-2-oxoethyl]methylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methoxyphenoxy)pyridin-3-yl]-4-trifluoromethylbenzamide, N-[6-(4-{[2-(4-piperonylpiperazin-1-yl)-2-oxoethyl]ethylamino}-2-methylphenoxy)pyridin-3-yl]-3,4-dichlorobenzamide, N-[6-(4-{[2-(4-piperonylpiperazin-1-yl)-2-oxoethyl]methylamino}-2-methylphenoxy)pyridin-3-yl]-4-trifluoromethylbenzamide, N-(6-{4-[3-(4-piperonylpiperazin-1-yl)-3-oxopropyl]phenoxy}pyridin-3-yl)-3,4-dichlorobenzenesulfonamide, N-[6-(4-{4-[2-(4-piperonylpiperazin-1-yl)-2-oxoethyl]piperazin-1-yl}phenoxy)pyridin-3-yl]-4-trifluoromethylbenzamide, N-[6-(4-{4-[2-(4-piperonylpiperazin-1-yl)-2-oxoethyl]piperidin-1-yl}phenoxy)pyridin-3-yl]-4-trifluoromethylbenzamide, N-{6-[(4-{4-[2-(4-piperonylpiperazin-1-yl)-2-oxoethyl]piperidin-1-yl}phenyl)methylamino]pyridin-3-yl}-4-trifluoromethylbenzamide, N-[6-(4-{4-[2-(4-benzylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-4-trifluoromethylbenzamide, N-[6-(4-{4-[2-(4-piperonylpiperazin-1-yl)-2-oxoethyl]piperidin-1-yl}-2-methylphenoxy)pyridin-3-yl]-3,4-dichlorobenzamide, N-{6-[4-(4-benzylpiperazine-1-carbonyl)phenoxy]pyridin-3-yl}-4-trifluoromethylbenzamide, N-{6-[4-(4-benzylpiperazine-1-carbonyl)phenoxy]pyridin-3-yl}-3,4-dichlorobenzamide, N-[6-({4-[3-(4-piperonylpiperazin-1-yl)-3-oxopropyl]phenyl}methylamino)pyridin-3-yl]-4-trifluoromethylbenzamide, N-[6-(4-{[2-(4-piperonylpiperazin-1-yl)-2-oxoethyl]

ethylamino}-2-fluorophenoxy)pyridin-3-yl]-3,4-dichlorobenzamide, N-[6-(4-{[2-(4-piperonylpiperazin-1-yl)-2-oxoethyl]methylamino}-2-fluorophenoxy)pyridin-3-yl]-3,4-dichlorobenzamide, N-[6-(4-{[2-(4-piperonylpiperazin-1-yl)-2-oxoethyl]methylamino}-2-methoxyphenoxy)pyridin-3-yl]-3,4-dichlorobenzamide, N-[6-(4-{[2-(4-piperonylpiperazin-1-yl)-2-oxoethyl]methylamino}phenoxy)pyridin-3-yl]-3,4-dichlorobenzamide, 1-(6-{4-[3-(4-piperonylpiperazin-1-yl)-3-oxopropyl]phenoxy}pyridin-3-yl)-3-(3,4-dichlorophenyl)-1-ethylurea, N-(6-{4-[3-(4-piperonylpiperazin-1-yl)-3-oxopropyl]phenoxy}pyridin-3-yl)-4-trifluoromethylbenzamide, N-[6-(4-{[2-(4-benzylpiperazin-1-yl)-2-oxoethyl]methylamino}-2-methylphenoxy)pyridin-3-yl]-4-trifluoromethylbenzamide, N-[6-(4-{4-[2-(4-benzylpiperazin-1-yl)-2-oxoethyl]piperidin-1-yl}phenoxy)pyridin-3-yl]-3,4-dichlorobenzamide, N-(6-{4-[3-(4-piperonylpiperazine-1-carbonyl)piperidin-1-yl]phenoxy}pyridin-3-yl)-3,4-dichlorobenzamide, N-[6-(4-{4-[2-(4-benzylpiperazin-1-yl)-2-oxoethyl]piperidin-1-yl}phenoxy)pyridin-3-yl]-4-trifluoromethylbenzamide, N-{6-[(4-{4-[2-(4-benzylpiperazin-1-yl)-2-oxoethyl]piperidin-1-yl}phenyl)methylamino]pyridin-3-yl}-4-trifluoromethylbenzamide, N-(6-{4-[(2-{4-[4-(4-fluorobenzoyl)phenyl]piperazin-1-yl}-2-oxoethyl)methylamino]-2-methoxyphenoxy}pyridin-3-yl)-4-trifluoromethylbenzamide, 2-(4-piperonylpiperazin-1-yl)-N-{3-methyl-4-[5-(4-trifluoromethylphenoxymethyl)pyridin-2-yloxy]phenyl}-2-oxoacetamide, N-[6-(4-{[2-(4-piperonylpiperazin-1-yl)-2-oxoethyl]methylamino}-2-methylphenoxy)pyridin-3-yl]-2-fluoro-4-trifluoromethylbenzamide, N-[6-(4-{4-[2-(4-piperonylpiperazin-1-yl)-2-oxoethyl]piperidin-1-yl}-2-methoxyphenoxy)pyridin-3-yl]-4-trifluoromethylbenzamide and 4-(3-{3-methyl-4-[5-(4-trifluoromethylbenzoylamino)pyridin-2-yloxy]phenyl}-2-oxohexahydropyrimidin-1-yl)benzoic acid ethyl ester, or a salt thereof as an active ingredient.

The aromatic compound or a salt thereof serving as the active ingredient of the present invention is a known compound and described in Patent Document 1.

Specific examples of individual groups shown in the general formula (1) are as follows.

Examples of the lower alkenylene group include linear or branched alkenylene groups having 2 to 6 carbon atoms and 1 to 3 double bonds such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, and 1,4-hexadienylene groups.

Examples of the lower alkynylene group include linear or branched alkynylene groups having 2 to 6 carbon atoms and 1 to 3 triple bonds such as ethynylene, 1-propynylene, 1-methyl-1-propynylene, 2-methyl-1-propynylene, 2-propynylene, 2-butynylene, 1-butynylene, 3-butynylene, 2-pentynylene, 1-pentynylene, 3-pentynylene, 4-pentynylene, 2-pentyn-4-ynylene, 2-hexynylene, 1-hexynylene, 5-hexynylene, 3-hexynylene, 4-hexynylene, 3,3-diethyl-1-propynylene, and 2-ethyl-1-propynylene groups.

Examples of the lower alkoxy group include linear or branched alkoxy groups having 1 to 6 carbon atoms such as methoxy, ethoxy, propoxy, isopropoxy, butoxy, tert-butoxyl, pentyloxy, and hexyloxy groups.

Examples of the lower alkyl group include linear or branched alkyl groups having 1 to 6 carbon atoms such as methyl, ethyl, propyl, isopropyl, 2,2-dimethylpropyl, 1-ethylpropyl, butyl, isobutyl, tert-butyl, isopentyl, pentyl, and hexyl groups.

Examples of the lower alkyl group which may have a lower alkoxy group as a substituent include, in addition to the above described lower alkyl groups, linear or branched alkyl groups having 1 to 6 carbon atoms which may have a linear or branched alkoxy group having 1 to 6 carbon atoms as a substituent such as methoxymethyl, 1-ethoxyethyl, 2-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups.

Examples of the lower alkanoyl group include linear or branched alkanoyl groups having 1 to 6 carbon atoms such as formyl, acetyl, propionyl, butyryl, isobutyryl, pentanoyl, tert-butylcarbonyl, and hexanoyl groups.

Examples of the phenyl lower alkyl group include phenylalkyl groups whose alkyl moiety is a linear or branched alkyl group having 1 to 6 carbon atoms such as benzyl, 2-phenylethyl, 1-phenylethyl, 3-phenylpropyl, 4-phenylbutyl, 5-phenylpentyl, 6-phenylhexyl, 1,1-dimethyl-2-phenylethyl, and 2-methyl-3-phenylpropyl groups.

Examples of the lower alkylene group include linear or branched alkylene groups having 1 to 6 carbon atoms such as methylene, ethylene, trimethylene, 2-methyltrimethylene, 2,2-dimethylethylene, 2,2-dimethyltrimethylene, 1-methyltrimethylene, methylmethylene, ethylmethylene, tetramethylene, pentamethylene, and hexamethylene groups.

Examples of the lower alkenylene group which may have a phenyl group as a substituent include linear or branched alkenylene groups, which have 2 to 6 carbon atoms and 1 to 3 double bonds, and which may have a phenyl group as a substituent such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-pentene-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, 1,4-hexadienylene, 1-phenylvinylene, 3-phenyl-1-propenylene, 3-phenyl-1-methyl-1-propenylene, 3-phenyl-2-methyl-1-propenylene, 1-phenyl-2-propenylene, 1-phenyl-2-butenylene, 3-phenyl-1-butenylene, 1-phenyl-3-butenylene, 5-phenyl-2-pentenylene, 4-phenyl-1-pentenylene, 2-phenyl-3-pentenylene, 1-phenyl-4-pentenylene, 1-phenyl-1,3-butadienylene, 1-phenyl-1,3-pentadienylene, 1-phenyl-2-penten-4-ynylene, 1-phenyl-2-hexenylene, 3-phenyl-1-hexenylene, 4-phenyl-5-hexenylene, 6-phenyl-3-hexenylene, 5-phenyl-4-hexenylene, 1-phenyl-3,3-dimethyl-1-propenylene, 1-phenyl-2-ethyl-1-propenylene, 6-phenyl-1,3,5-hexatrienylene, 1-phenyl-1,3-hexadienylene, and 2-phenyl-1,4-hexadienylene groups.

Examples of the lower alkylene group which may be substituted with a group selected from the group consisting of a lower alkoxy group and a phenyl group include, in addition to the above described lower alkylene groups, linear or branched alkylene groups having 1 to 6 carbon atoms which may be substituted with 1 or 2 groups selected from the group consisting of a linear or branched alkoxy group having 1 to 6 carbon atoms and a phenyl group such as methoxymethylene, 2-phenylethylene, 3-ethyoxytrimethylene, 1-propoxy-2-methyltrimethylene, 1-phenyl-2,2-dimethylethylene, 3-phenyl-2,2-dimethyltrimethylene, 2-butoxy-1-methyltrimethylene, phenylmethylmethylene, 2-pentyloxyethylmethylene, 4-phenyl-2-hexyloxytetramethylene, 3-phenylpentamethylene, 5-phenylhexamethylene, ethoxymethylene, 1-phenylethylene, 3-phenyltrimethylene, and 2-phenyl-1-methoxyethylene groups.

Examples of the 5- to 15-membered monocyclic, bicyclic or tricyclic saturated or unsaturated heterocyclic group which has 1 to 4 nitrogen atoms, oxygen atoms or sulfur atoms include pyrrolidinyl, piperidinyl, piperazinyl, morpholino, pyridyl, 1,2,5,6-tetrahydropyridyl, 1,2,4-triazolyl, 1,2,3-triazolyl, 1,2,5-triazolyl, thiazolidinyl, 1,2,3,4-tetrazolyl, thienyl, quinolyl, 1,4-dihydroquinolyl, benzothiazolyl, pyrazyl, pyrimidyl, pyridazyl, 2H-pyrrolyl, pyrrolyl, 1,3,4-oxadiazolyl, tetrahydropyranyl, tetrahydrofuryl, furazanyl, carbostyryl, 3,4-dihydrocarbostyryl, 1,2,3,4-tetrahydroquinolyl, 1,2,3,4-tetrahydroisoquinolyl, indolyl, isoindolyl, indolinyl, benzoimidazolyl, benzooxazolyl, imidazolidinyl, isoquinolyl, quinazolidinyl, quinoxalinyl, cinnolinyl, phthalazinyl, carbazoyl, acridinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxathiinyl, phenoxazinyl, 4H-chromenyl, 1H-indazolyl, phenazinyl, xanthenyl, thianthrenyl, 2-imidazolinyl, 2-pyrrolinyl, furyl, oxazolyl, isooxazolyl, isooxazolidinyl, thiazolyl, isothiazolyl, pyranyl, 2-thiazolinyl, 2-pyrazolinyl, quinuclidinyl, 1,4-benzooxadinyl, 3,4-dihydro-2H-1,4-benzooxadinyl, 3,4-dihydro-2H-1,4-benzothiazinyl, 1,4-benzothiazinyl, 1,2,3,4-tetrahydroquinoxalinyl, 1,3-dithia-2,4-dihydronaphthalenyl, phenanthridinyl, 1,4-dithianaphthalenyl, dibenz[b,e]azepine, and 6,11-dihydro-5H-dibenz[b,e]azepine groups.

Examples of the halogen atom include a fluorine atom, chlorine atom, bromine atom and iodine atom.

Examples of the lower alkoxy group which may have a halogen atom as a substituent include linear or branched alkoxy groups having 1 to 6 carbon atoms which may have 1 to 3 halogen atoms as substituents such as methoxy, ethoxy, propoxy, isopropoxy, butoxy, tert-butoxy, pentyloxy, hexyloxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, and 5,6-dichlorohexyloxy groups.

Examples of the lower alkyl group which may have a halogen atom as a substituent include, in addition to the above described lower alkyl groups, linear or branched alkyl groups having 1 to 6 carbon atoms which may have 1 to 3 halogen atoms as substituents such as trifluoromethyl, trichloromethyl, chloromethyl, bromomethyl, fluoromethyl, iodomethyl, difluoromethyl, dibromomethyl, dichloromethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of the lower alkylsulfonyl group include linear or branched alkylsulfonyl groups having 1 to 6 carbon atoms such as methylsulfonyl, ethylsulfonyl, propylsulfonyl, isopropylsulfonyl, butylsulfonyl, tert-butylsulfonyl, pentylsulfonyl, and hexylsulfonyl groups.

Examples of the phenyl group which may be substituted, on the phenyl ring, with a lower alkyl group which may have a halogen atom include phenyl groups which may be substituted, on the phenyl ring, with 1 to 3 linear or branched alkyl groups having 1 to 6 carbon atoms which may have 1 to 3 halogen atoms such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, and 3-ethyl-4-trichloromethyl groups.

Examples of the lower alkylthio group include linear or branched alkylthio groups having 1 to 6 carbon atoms such as methylthio, ethylthio, propylthio, isopropylthio, butylthio, tert-butylthio, pentylthio, and hexylthio groups.

Examples of the amino group which may have a group selected from the group consisting of a lower alkyl group and a lower alkanoyl group as a substituent include amino groups which may have 1 or 2 groups selected from the group consisting of linear or branched alkyl groups having 1 to 6 carbon atoms and linear or branched alkanoyl groups having 1 to 6 carbon atoms as substituents such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-acetylamino, N-formylamino, N-propionylamino, N-butyrylamino, N-isobutyrylamino, N-pentanoylamino, N-tert-butylcarbonylamino, N-hexanoylamino, diacetylamino, N-acetyl-N-methylamino, and N-acetyl-N-ethylamino groups.

Examples of the naphthyl group which may be substituted on the naphthalene ring with 1 to 3 substituents selected from the group consisting of a lower alkyl group, a halogen atom, and an amino group which may have a group selected from the group consisting of a lower alkyl group and a lower alkanoyl group include naphthyl groups which may have, on the naphthalene ring, 1 to 3 substituents selected from the group consisting of a linear or branched alkyl group having 1 to 6 carbon atoms, a halogen atom, and an amino group which may have 1 or 2 substituents selected from the group consisting of a linear or branched alkyl group having 1 to 6 carbon atoms and a linear or branched alkanoyl group having 1 to 6 carbon atoms such as (1-or 2-)naphthyl, 1-methyl-(2-, 3-, 4-, 5-, 6-, 7- or 8-)naphthyl, 2-ethyl-(1-, 3-, 4-, 5-, 6-, 7- or 8-)naphthyl, 3-n-propyl-(1-, 2-, 4-, 5-, 6-, 7- or 8-)naphthyl, 4-n-butyl-(1-, 2-, 3-, 5-, 6-, 7- or 8-)naphthyl, 4-methyl-(1-, 2-, 3-, 5-, 6-, 7- or 8-)naphthyl, 5-n-pentyl-(1-, 2-, 3-, 4-, 6-, 7- or 8-)naphthyl, 6-n-hexyl-(1-, 2-, 3-, 4-, 5-, 7- or 8-)naphthyl, 1,7-dimethyl-(2-, 3-, 4-, 5-, 6- or 8-)naphthyl, 1,2,8-trimethyl-(3-, 4-, 5-, 6- or 7-)naphthyl, 1-dimethylamino-(2-, 3-, 4-, 5-, 6-, 7- or 8-)naphthyl, 2-dimethylamino-(1-, 3-, 4-, 5-, 6-, 7- or 8-)naphthyl, 3-methylamino-(1-, 2-, 4-, 5-, 6-, 7- or 8-)naphthyl, 5-amino-(1-, 2-, 3-, 4-, 6-, 7- or 8-)naphthyl, 5-dimethylamino-(1-, 2-, 3-, 4-, 6-, 7- or 8-)naphthyl, 4-(N-methyl-N-ethylamino)-(1-, 2-, 3-, 5-, 6-, 7- or 8-)naphthyl, 1-methyl-2-dimethylamino-(3-, 4-, 5-, 6-, 7- or 8-)naphthyl, 1-chloro-(2-, 3-, 4-, 5-, 6-, 7- or 8-)naphthyl, and 1-acetylamino-(2-, 3-, 4-, 5-, 6-, 7- or 8-)naphthyl groups.

Examples of the alkyl group which may have a lower alkoxy group as a substituent include, in addition to the above described lower alkyl groups which may have a lower alkoxy group as a substituent, linear or branched alkyl groups having 1 to 8 carbon atoms which may have a linear or branched alkoxy group having 1 to 6 carbon atoms as a substituent such as heptyl, 1-ethylpentyl, octyl, 7-methoxyheptyl, 1-ethoxyheptyl, 2-propoxyl-1-ethylpentyl, 3-isopropoxyoctyl, 7-butoxyheptyl, 8-pentyloxyoctyl, and 5-hexyloxy-1-ethylpentyl groups.

Examples of the amino substituted lower alkyl group which may have a lower alkyl group include linear or branched alkyl groups having 1 to 6 carbon atoms substituted with an amino group which may have 1 or 2 linear or branched alkyl groups having 1 to 6 carbon atoms such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-diisopropylaminoethyl, (N-ethyl-N-propylamino)methyl, and 2-(N-methyl-N-hexylamino)ethyl groups.

Examples of the cycloalkyl group include cycloalkyl groups having 3 to 16 carbon atoms such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cycloteradecyl, cyclopentadecyl, and cyclohexadecyl groups.

Examples of the cycloalkyl group which may be substituted with a group selected from the group consisting of an amino substituted lower alkyl group which may have a lower alkyl group and a lower alkyl group which may have a halogen atom as a substituent on the cycloalkyl ring include, in addition to the above described cycloalkyl groups, cycloalkyl groups having 3 to 16 carbon atoms which may be substituted, on the cycloalkyl ring, with 1 to 3 groups selected from the group consisting of a linear or branched alkyl group having 1 to 6 carbon atoms substituted with an amino group which may have 1 or 2 linear or branched alkyl groups having 1 to 6 carbon atoms and a linear or branched alkyl group having 1 to 6 carbon atoms which may have 1 to 3 halogen atoms as substituents such as 4-dimethylaminomethylcyclohexyl, 2-(aminomethyl)cyclopropyl, 3-(2-aminomethyl)cyclobutyl, 2-(1-aminoethyl)cyclopentyl, 3-(3-aminopropyl)cyclohexyl, 3-(4-aminobutyl)cycloheptyl, 4-(5-aminopentyl)cyclooctyl, 4-(6-aminohexyl)cyclohexyl, 2-(1,1-dimethyl-2-aminoethyl)cycloheptyl, 3-(2-methyl-3-aminopropyl)cyclopentyl, 3-(methylaminomethyl)cyclohexyl, 2-(1-ethylaminoethyl)cyclooctyl, 2-(2-propylaminoethyl)cyclohexyl, 3-(3-isopropylaminopropyl)cyclopentyl, 4-(4-butylaminobutyl)cycloheptyl, 2-(5-pentylaminopentyl)cyclohexyl, 2-(6-hexylaminohexyl)cyclopentyl, 3-(dimethylaminomethyl)cyclohexyl, 3-[(N-ethyl-N-propylamino)methyl]cycloheptyl, 4-[2-(N-methyl-N-hexylamino)ethyl]cyclooctyl, 4-dimethylaminomethylcyclononyl, 2-(aminomethyl)cyclodecyl, 3-(2-aminomethyl)cycloundecyl, 2-(1-aminoethyl)cyclododecyl, 3-(3-aminopropyl)cyclotridecyl, 3-(4-aminobutyl)cyclotetradecyl, 4-(5-aminopentyl)cyclopentadecyl, 4-(6-aminohexyl)cyclohexadecyl, 2-(1,1-dimethyl-2-aminoethyl)cyclononyl, 3-(2-methyl-3-aminopropyl)cyclodecyl, 3-(methylaminomethyl)cycloundecyl, 2-(1-ethylaminoethyl)cyclododecyl, 2-(2-propylaminoethyl)cyclotridecyl, 3-(3-isopropylaminopropyl)cyclotetradecyl, 4-(4-butylaminobutyl)cyclopentadecyl, 2-(5-pentylaminopentyl)cyclohexadecyl, 2-(6-hexylaminohexyl)cyclononyl, 3-(dimethylaminomethyl)cyclododecyl, 3-[(N-ethyl-N-propylamino)methyl]cyclodecyl, 4-[2-(N-methyl-N-hexylamino)ethyl]cyclohexadecyl, 2,2-dimethylcyclopropyl, and 2-trifluoromethylcyclopropyl groups.

Examples of the lower alkenyl group include linear or branched alkenyl groups having 2 to 6 carbon atoms and 1 to 3 double bonds such as vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl groups.

Examples of the lower alkenyl group which may have a halogen atom as a substituent include, in addition to the above described lower alkenyl groups, linear or branched alkenyl groups having 2 to 6 carbon atoms which may have 1 to 3 halogen atoms as substituents and which have 1 to 3 double bonds such as 3,3,3-trifluoro-1-propenyl, 2-bromovinyl, 3-chloro-1-propenyl, 3-iodo-1-methyl-1-propenyl, 3-fluoro-2-methyl-1-propenyl, 2-butenyl, 4,4,3-trichloro-1-butenyl, 4,4-difluoro-3-butenyl, 5-fluoro-2-pentenyl, 5,5,3-tribromo-1-pentenyl, 5-chloro-3-pentenyl, 5,5,5-trifluoro-4-pentenyl, 4-chloro-1,3-butadienyl, 5-fluoro-1,3-pentadienyl, 5-bromo-2-penten-4-ynyl, 6-fluoro-2-hexenyl, 6,6,5-trifluoro-1-hexenyl, 6-chloro-5-hexenyl, 5-bromo-3-hexenyl, 6-chloro-4-hexenyl, 3,3-dimethyl-2-chloro-1-propenyl, 3-fluoro-2-ethyl-1-propenyl, 6-chloro-1,3,5-hexatrienyl, 6-bromo-1,3-hexadienyl, and 6-fluoro-1,4-hexadienyl groups.

Examples of the benzoyl group (which may have, on the phenyl ring, 1 to 3 substituents selected from the group consisting of a lower alkyl group which may have a halogen atom as a substituent and a halogen atom) include benzoyl groups (which may have, on the phenyl ring, with 1 to 3 substituents selected from the group consisting of a linear or branched alkyl group having 1 to 6 carbon atoms and which may have 1 to 3 halogen atoms as substituents and a halogen atom) such as benzoyl, 3,4-difluorobenzoyl, 2-fluorobenzoyl, 3-bromobenzoyl, 4-iodobenzoyl, 4-methylbenzoyl, 2-methylbenzoyl, 3-methylbenzoyl, 2-ethylbenzoyl, 3-ethylbenzoyl, 4-ethylbenzoyl, 4-isopropylbenzoyl, 3-butylbenzoyl, 4-pentylbenzoyl, 4-hexylbenzoyl, 3,4-dimethylbenzoyl, 3,4-diethylbenzoyl, 2,4-dimethylbenzoyl, 2,5-dimethylbenzoyl, 2,6-dimethylbenzoyl, 3,4,5-trimethylbenzoyl, 2-trifluoromethylbenzoyl, 3-trifluoromethylbenzoyl, 4-trifluoromethylbenzoyl, 2-(bromomethyl)benzoyl, 3-(2-chloroethyl)benzoyl, 4-(2,3-dichloropropyl)benzoyl, 4-(4-fluorobutyl)benzoyl, 3-(5-chloropentyl)benzoyl, 4-(5-bromohexyl)benzoyl, 4-(5,6-dibromohexyl)benzoyl, 3,4-di(trifluoromethyl)benzoyl, 3,4-di(4,4,4-trichlorobutyl)benzoyl, 2,4-di(3-chloro-2-methylpropyl)benzoyl, 2,5-di(3-chloropropyl)benzoyl, 2,6-di(2,2,2-trifluoroethyl)benzoyl, 3,4,5-tri(trifluoromethyl)benzoyl, 4-(2,2,2-trichloroethyl)benzoyl, 2-methyl-4-trifluoromethylbenzoyl, 3-ethyl-4-trichloromethylbenzoyl, 2-chloro-4-trifluoromethylbenzoyl, 3-ethyl-4-fluorobenzoyl, 3-fluoro-4-trichloromethylbenzoyl, 2-methyl-3-trifluoromethyl-4-trifluoromethylbenzoyl, 3-fluorobenzoyl, 4-fluorobenzoyl, 2-bromobenzoyl, 4-bromobenzoyl, 2-iodobenzoyl, 3-iodobenzoyl, 2,3-dibromobenzoyl, 2,4-diiodobenzoyl, 2,5-difluorobenzoyl, 2,6-dichlorobenzoyl, 2,4,6-trichlorobenzoyl, 2,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 3,4-dichlorobenzoyl, 2,6-dichlorobenzoyl, 3,5-dichlorobenzoyl, 2,4,6-trifluorobenzoyl, and 2,4-difluorobenzoyl groups.

Examples of the halogen substituted lower alkyl group include linear or branched alkyl groups having 1 to 6 carbon atoms which have 1 to 3 halogen atoms as substituents such as trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of the lower alkylenedioxy group include linear or branched alkylene groups having 1 to 4 carbon atoms such as methylenedioxy, ethylenedioxy, trimethylenedioxy, and tetramethylenedioxy groups.

Examples of the amino group which may have a substituent selected from the group consisting of a lower alkyl group, a lower alkanoyl group, a benzoyl group and a cycloalkyl group include amino groups which may have 1 or 2 substituents selected from the group consisting of a linear or branched alkyl group having 1 to 6 carbon atoms, a linear or branched alkanoyl group having 1 to 6 carbon atoms, a benzoyl group, and a cycloalkyl group having 3 to 16 carbon atoms such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, N-benzoylamino, N-ethyl-N-benzoylamino, N-methyl-N-benzoylamino, N-acetyl-N-benzoylamino, cyclopropylamino, cyclobutylamino, cyclopentylamino, cyclohexylamino, cycloheptylamino, cyclooctylamino, N-methyl-N-cyclohexylamino, N-methyl-N-cyclopentylamino, N-methyl-N-cycloheptylamino, N-cyclohexyl-N-acetylamino, N-cyclopentyl-N-benzoylamino, cyclononylamino, cyclodecylamino, cyclododecylamino, cyclotridecylamino, cyclotetradecylamino, cyclopentadecylamino, N-methyl-N-cyclohexadecylamino, N-methyl-N-cyclononylamino, N-methyl-N-cyclodecylamino, N-cycloundecyl-N-acetylamino, and N-cyclohexadecyl-N-benzoyl groups.

Examples of the lower alkanoyl group which may have a halogen atom as a substituent include, in addition to the above described lower alkanoyl groups, linear or branched alkanoyl groups having 2 to 6 carbon atoms which may have 1 to 3 halogen atoms as substituents such as 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, and 5,6-dibromohexanoyl groups.

Examples of the lower alkoxycarbonyl group include alkoxycarbonyl groups whose alkoxy moiety is a linear or branched alkoxy group having 1 to 6 carbon atoms such as methoxycarbonyl, ethoxycarbonyl, propoxycarbonyl, isopropoxycarbonyl, butoxycarbonyl, tert-butoxycarbonyl, pentyloxycarbonyl, and hexyloxycarbonyl groups.

Examples of the lower alkanoyloxy group include linear or branched alkanoyloxy groups having 2 to 6 carbon atoms such as acetyloxy, propionyloxy, butyryloxy, isobutyryloxy, pentanoyloxy, tert-butylcarbonyloxy, and hexanoyloxy groups.

Examples of the 5- or 6-membered saturated or unsaturated heterocyclic group having 1 to 4 nitrogen atoms, oxygen atoms or sulfur atoms include pyrrolidinyl, piperidinyl, piperazinyl, morpholino, thiomorpholino, pyridyl, 1,2,5,6-tetrahydropyridyl, thienyl, pyrazyl, pyrimidyl, pyridazyl, pyrrolyl, 2H-pyrrolyl, imidazolidinyl, pyrazolyl, imidazolyl, pyrazolidinyl, furazanyl, 2-imidazolinyl, imidazolidinyl, 2-pyrrolinyl, furyl, oxazolyl, isooxazolidinyl, isooxazolyl, thiazolyl, isothiazolyl, pyranyl, 2-pyrazolidinyl, 1,2,4-triazolyl, 1,2,3-triazolyl, 1,2,5-triazolyl, thiazolidinyl, 2-thiazolinyl, 1,2,3,4-tetrazolyl, 1,3,4-oxadiazolyl, tetrahydropyranyl, and tetrahydrofuryl groups.

Examples of the 5-to 7-membered saturated heterocyclic ring formed by binding $R^{11}$ and $R^{12}$ each other, together with nitrogen atoms bound to them, through or not through a nitrogen atom, a sulfur atom or an oxygen atom, include pyrrolidinyl, piperidinyl, piperazinyl, morpholino, thiomorpholino, and homopiperazinyl groups.

Examples of the imidazolyl lower alkyl group include imidazolylalkyl groups whose alkyl moiety is a linear or branched alkyl group having 1 to 6 carbon atoms such as (1, 2, 4 or 5-)imidazolylmethyl, 2-[(1, 2, 4 or 5-)imidazolyl]ethyl, 1-[(1, 2, 4 or 5-)imidazolyl]ethyl, 3-[(1, 2, 4 or 5-)imidazolyl]propyl, 4-[(1, 2, 4 or 5-)imidazolyl]butyl, 5-[(1, 2, 4 or 5-)imidazolyl]pentyl, 6-[(1, 2, 4 or 5-)imidazolyl]hexyl, 1,1-dimethyl-2-[(1, 2, 4 or 5-)imidazolyl]ethyl, and 2-methyl-3-[(1, 2, 4 or 5-)imidazolyl]propyl groups.

Examples of the 1,2,4-triazolyl lower alkyl group include 1,2,4-triazolylalkyl groups whose alkyl moiety is a linear or branched alkyl group having 1 to 6 carbon atoms such as (1, 3 or 5-)1,2,4-triazolylmethyl, 2-[(1, 3 or 5-)1,2,4-triazolyl]ethyl, 1-[(1, 3 or 5-)1,2,4-triazolyl]ethyl, 3-[(1, 3 or 5-)1,2,4-triazolyl]propyl, 4-[(1, 3 or 5-)1,2,4-triazolyl]butyl, 5-[(1, 3 or 5-)1,2,4-triazolyl]pentyl, 6-[(1, 3 or 5-)1,2,4-triazolyl]hexyl, 1,1-dimethyl-2-[(1, 3 or 5-)1,2,4-triazolyl]ethyl, and 2-methyl-3-[(1, 3 or 5-)1,2,4-triazolyl]propyl groups.

Examples of the 1,2,3-triazolyl lower alkyl group include 1,2,3-triazolylalkyl groups whose alkyl moiety is a linear or branched alkyl group having 1 to 6 carbon atoms such as (1, 4 or 5-)1,2,3-triazolylmethyl, 2-[(1, 4 or 5-)1,2,3-triazolyl]ethyl, 1-[(1, 4 or 5-)1,2,3-triazolyl]ethyl, 3-[(1, 4 or 5-)1,2,3-triazolyl]propyl, 4-[(1, 4 or 5-)1,2,3-triazolyl]butyl, 5-[(1, 4 or 5-)1,2,3-triazolyl]pentyl, 6-[(1, 4 or 5-)1,2,3-triazolyl]hexyl, 1,1-dimethyl-2-[(1, 4 or 5-)1,2,3-triazolyl]ethyl, and 2-methyl-3-[(1, 4 or 5-)1,2,3-triazolyl]propyl groups.

Examples of the 1,2,5-triazolyl lower alkyl group include 1,2,5-triazolylalkyl groups whose alkyl moiety is a linear or branched alkyl group having 1 to 6 carbon atoms such as (1, 3 or 4-)1,2,5-triazolylmethyl, 2-[(1, 3 or 4-)1,2,5-triazolyl]ethyl, 1-[(1, 3 or 4-)1,2,5-triazolyl]ethyl, 3-[(1, 3 or 4-)1,2,5-triazolyl]propyl, 4-[(1, 3 or 4-)1,2,5-triazolyl]butyl, 5-[(1, 3 or 4-)1,2,5-triazolyl]pentyl, 6-[(1, 3 or 4-)1,2,5-triazolyl]hexyl, 1,1-dimethyl-2-[(1, 3 or 4-)1,2,5-triazolyl]ethyl, and 2-methyl-3-[(1, 3 or 4-)1,2,5-triazolyl]propyl groups.

Examples of the pyrazolyl lower alkyl group include pyrazolylalkyl groups whose alkyl moiety is a linear or branched alkyl group having 1 to 6 carbon atoms such as (1, 3, 4 or 5-)pyrazolylmethyl, 2-[(1, 3, 4 or 5-)pyrazolyl]ethyl, 1-[(1, 3, 4 or 5-)pyrazolyl]ethyl, 3-[(1, 3, 4 or 5-)pyrazolyl]propyl, 4-[(1, 3, 4 or 5-)pyrazolyl]butyl, 5-[(1, 3, 4 or 5-)pyrazolyl]pentyl, 6-[(1, 3, 4 or 5-)pyrazolyl]hexyl, 1,1-dimethyl-2-[(1, 3, 4 or 5-)pyrazolyl]ethyl, and 2-methyl-3-[(1, 3, 4 or 5-)pyrazolyl]propyl groups.

Examples of the pyrimidinyl lower alkyl group which may have an oxo group as a substituent on the pyrimidine ring include pyrimidinylalkyl groups which may have 1 to 3 oxo groups as substituents on the pyrimidine ring and whose alkyl moiety is a linear or branched alkyl group having 1 to 6 carbon atoms such as (2, 4, 5 or 6-)pyrimidinylmethyl, 2-[(2, 4, 5 or 6-)pyrimidinyl]ethyl, 1-[(2, 4, 5 or 6-)pyrimidinyl]ethyl, 3-[(2, 4, 5 or 6-)pyrimidinyl]propyl, 4-[(2, 4, 5 or 6-)pyrimidinyl]butyl, 5-[(2, 4, 5 or 6-)pyrimidinyl]pentyl, 6-[(2, 4, 5 or 6-)pyrimidinyl]hexyl, 1,1-dimethyl-2-[(2, 4, 5 or 6-)pyrimidinyl]ethyl, 2-methyl-3-[(2, 4, 5 or 6-)pyrimidinyl]propyl, [(1, 3, 4 or 5-)2,6-dioxopryrimidinyl]methyl, [(1, 3, 4, 5 or 6-)2-oxopyrimidinyl]methyl, [(1, 2, 4 or 5-)6-oxopyrimidinyl]methyl, [(1, 2, 5 or 6-)4-oxopyrimidinyl]methyl, [(1, 3, 5 or 6-)2,4-dioxopyrimidinyl]methyl, 2-[(4 or 6-)2,5-dioxopyrimidinyl]ethyl, 1-[(1, 3, 4 or 5-)2,6-dioxopyrimidinyl]ethyl, 3-[(1, 3 or 5-)2,4,6-trioxopyrimidinyl]propyl, 4-[(1, 3, 4 or 5-)2,6-dioxopyrimidinyl]butyl, 5-[(4 or 6-)2,5-dioxopyrimidinyl]pentyl, 6-[(1, 3, 5 or 6-)2,4-dioxopyrimidinyl]hexyl, 1,1-dimethyl-[(1, 3, 4 or 5-)2,6-dioxopyrimidinyl]ethyl, and 2-methyl-3-[(1, 3, 4 or 5-)2,6-dioxopyrimidinyl]propyl groups.

Examples of the 3,5-dioxoisoxazolidin-4-ylidene lower alkyl group include 3,5-dioxoisoxazolidin-4-ylidenealkyl groups whose alkyl moiety is a linear or branched alkyl group having 1 to 6 carbon atoms such as 3,5-dioxoisoxazolidin-4-ylidenemethyl, 3,5-dioxoisoxazolidin-4-ylideneethyl, 3,5-dioxoisoxazolidin-4-ylidenepropyl, 3,5-dioxoisoxazolidin-4-ylideneisopropyl, 3,5-dioxoisoxazolidin-4-ylidenebutyl, 3,5-dioxoisoxazolidin-4-ylidenepentyl, and 3,5-dioxoisoxazolidin-4-ylidenehexyl groups.

Examples of the 1,2,4-oxadiazolyl lower alkyl group which may have a lower alkyl group as a substituent on the 1,2,4-oxadiazol ring include 1,2,4-oxadiazolylalkyl groups which may have a linear or branched alkyl group having 1 to 6 carbon atoms as a substituent on the 1,2,4-oxadiazol ring and whose alkyl moiety is a linear or branched alkyl group having 1 to 6 carbon atoms such as (3 or 5-)1,2,4-oxadiazolylmethyl, 2-[(3 or 5-)1,2,4-oxadiazolyl]ethyl, 1-[(3 or 5-)1,2,4-oxadiazolyl]ethyl, 3-[(3 or 5-)1,2,4-oxadiazolyl]propyl, 4-[(3 or 5-)1,2,4-oxadiazolyl]butyl, 5-[(3 or 5-)1,2,4-oxadiazolyl]pentyl, 6-[(3 or 5-)1,2,4-oxadiazolyl]hexyl, 1,1-dimethyl-2-[(3 or 5-)1,2,4-oxadiazolyl]ethyl, 2-methyl-3-[(3 or 5-)1,2,4-oxadiazolyl]propyl, 5-methyl-3-(1,2,4-oxadiazolyl)methyl, 3-ethyl-2-[5-(1,2,4-oxadiazolyl)]ethyl, 1-[3-propyl-5-(1,2,4-oxadiazolyl)]ethyl, 3-[5-butyl-3-(1,2,4-oxadiazolyl)]propyl, 4-[3-pentyl-5-(1,2,4-oxadiazolyl)]butyl, 5-[5-hexyl-3-(1,2,4-oxadiazolyl)]pentyl, 6-[3-methyl-5-(1,2,4-oxadiazolyl)]hexyl, 1,1-dimethyl-2-[5-isopropyl-3-(1,2,4-oxadiazolyl)]ethyl, and 2-methyl-3-[3-isobutyl-5-(1,2,4-oxadiazolyl)]propyl groups.

Examples of the thiazolydinyl lower alkyl group which may have an oxo group as a substituent on the thiazolydine ring include thiazolydinylalkyl groups which may have 1 to 3 oxo groups as substituents on the thiazolydine ring and whose alkyl moiety is a linear or branched alkyl group having 1 to 6 carbon atoms such as (2, 3, 4 or 5-)thiazolidinylmethyl, 2-[(2, 3, 4 or 5-)thiazolidinyl]ethyl, 1-[(2, 3, 4 or 5-)thiazolidinyl]ethyl, 3-[(2, 3, 4 or 5-)thiazolidinyl]propyl, 4-[(2, 3, 4 or 5-)thiazolidinyl]butyl, 5-[(2, 3, 4 or 5-)thiazolidinyl]pentyl, 6-[(2, 3, 4 or 5-)thiazolidinyl]hexyl, 1,1-dimethyl-2-[(2, 3, 4 or 5-)thiazolidinyl]ethyl, 2-methyl-3-[(2, 3, 4 or 5-)thiazolidinyl]propyl, 2,4-dioxo-5-thiazolidinylmethyl, 2-[2-oxo-(3, 4 or 5-)thiazolidinyl]ethyl, 1-[4-oxo-(2, 3 or 5-)thiazolidinyl]ethyl, 3-[5-oxo-(2, 3 or 4-)thiazolidinyl]propyl, 4-[2,5-dioxo-(3 or 4-)thiazolidinyl]butyl, 5-[2,4,5-trioxo-3-thiazolidinyl]pentyl, 6-[4,5-dioxo-(2 or 3-)thiazolidinyl]hexyl, 1,1-dimethyl-2-[2,4-dioxo-(3 or 5-)thiazolidinyl]ethyl, 2-methyl-3-[2,4-dioxo-(3 or 5-)thiazolidinyl]propyl, and 3-[2,4-dioxo-(3 or 5-)thiazolidinyl]propyl groups.

Examples of the phenyl lower alkyl group which may have a lower alkylenedioxy group as a substituent on the phenyl ring include, in addition to the above described phenyl lower alkyl groups, phenylalkyl groups which may have a linear or branched alkylenedioxy group having 1 to 4 carbon atoms as a substituent on the phenyl ring and whose alkyl moiety is a linear or branched alkyl group having 1 to 6 carbon atoms such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyflethyl, and 2-methyl-3-(3,4-ethylenedioxyphenyl)propyl groups.

Examples of the lower alkoxycarbonyl lower alkyl group include alkoxycarbonylalkyl groups whose alkoxy moiety is a linear or branched alkoxy group having 1 to 6 carbon atoms and whose alkyl moiety is a linear or branched alkyl group having 1 to 6 carbon atoms such as methoxycarbonylmethyl, ethoxycarbonylmethyl, 2-methoxycarbonylethyl, 2-ethoxycarbonylethyl, 1-ethoxycarbonylethyl, 3-methoxycarbonylpropyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, and hexyloxycarbonylmethyl groups.

Examples of the carboxy lower alkyl group include carboxyalkyl groups whose alkyl moiety is a linear or branched alkyl group having 1 to 6 carbon atoms such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, and 2-methyl-3-carboxypropyl groups.

Examples of the morpholino substituted lower alkanoyl group include morpholino substituted alkanoyl groups whose alkanoyl moiety is a linear or branched alkanoyl group having 2 to 6 carbon atoms such as 2-[(2, 3 or 4-)morpholino]acetyl group, 3-[(2, 3 or 4-)morpholino]propionyl, 2-[(2, 3 or 4-)morpholino]propionyl, 4-[(2, 3 or 4-)morpholino]butyryl, 5-[(2, 3 or 4-)morpholino]pentanoyl, 6-[(2, 3 or 4-)morpholino]hexanoyl, 2,2-dimethyl-2-[(2, 3 or 4-)morpholino]propionyl, and 2-methyl-3-[(2, 3 or 4-)morpholino]propionyl groups.

Examples of the piperazinylcarbonyl lower alkyl group which may be substituted on the piperazine ring with a phenyl lower alkyl group which may have a lower alkylenedioxy group as a substituent on the phenyl ring include piperazinylcarbonylalkyl groups whose alkyl moiety is a linear or branched alkyl group having 1 to 6 carbon atoms and which may be substituted on the piperazine ring with 1 to 3 phenylalkyl groups which may have a linear or branched alkylenedioxy group having 1 to 4 carbon atoms as a substituent on the phenyl group and whose alkyl moiety is a linear or branched alkyl group having 1 to 6 carbon atoms such as [(1, 2 or 3-)piperazinyl]carbonylmethyl, 2-[(1, 2 or 3-)piperazinyl]carbonylethyl, 1-[(1, 2 or 3-)piperazinyl]carbonylethyl, 3-[(1, 2 or 3-)piperazinyl]carbonylpropyl, 4-[(1, 2 or 3-)piperazinyl]carbonylbutyl, 5-[(1, 2 or 3-)piperazinyl]carbonylpentyl, 6-[(1, 2 or 3-)piperazinyl]carbonylhexyl, 1,1-dimethyl-2-[(1, 2 or 3-)piperazinyl]carbonylethyl, 2-methyl-3-[(1, 2 or 3-)piperazinyl]carbonylpropyl, (4-benzyl-1-piperazinylcarbonyl)methyl, 2-[4-(2-phenylethyl)-1-piperazinylcarbonyl]ethyl, 1-[4-(3-phenylpropyl)-1-piperazinylcarbonyl]ethyl, 3-[4-(4-phenylbutyl)-1-piperazinylcarbonyl]propyl, 4-[4-(5-phenylpentyl)-1-piperazinylcarbonyl]butyl, 5-[4-(6-phenylpropyl)-1-piperazinylcarbonyl]pentyl, 6-(4-benzyl-1-piperazinylcarbonyl)hexyl, 1,1-dimethyl-2-(4-benzyl-1-piperazinylcarbonyl)ethyl, 2-methyl-3-(4-benzyl-1-piperazinylcarbonyl)propyl, [4-(3,4-methylenedioxybenzyl)-1-piperazinylcarbonyl]methyl, 2-{4-[2-(2,3-ethylenedioxyphenyl)ethyl]-1-piperazinylcarbonyl}ethyl, 1-{4-[3-(3,4-trimethylenedioxyphenyl)propyl]-1-piperazinylcarbonyl}ethyl, 3-{4-[4-(2,3-tetramethylenedioxyphenyl)butyl]-1-piperazinylcarbonyl}propyl, 4-{4-[5-(3,4-methylenedioxyphenyl)pentyl]-1-piperazinylcarbonyl}butyl, 5-{4-[3-(2,3-ethylenedioxyphenyl)propyl]-1-piperazinylcarbonyl}pentyl, 6-[4-(3,4-trimethylenedioxybenzyl)-1-piperazinylcarbonyl]hexyl, 1,1-dimethyl-2-[4-(2,3-tetramethylenedioxybenzyl)-1-piperazinylcarbonyl]ethyl, 2-methyl-3-[4-(3,4-methylenedioxybenzyl)-1-piperazinylcarbonyl]propyl, (3,4-dibenzyl-1-piperazinylcarbonyl)methyl, (3,4,5-tribenzyl-1-piperazinylcarbonyl)methyl, [2,4-di(3,4-methylenedioxybenzyl)-1-piperazinylcarbonyl]methyl, [2,4,6-tri(3,4-methylenedioxybenzyl)-1-piperazinylcarbonyl]methyl, and [3-benzyl-4-(3,4-methylenedioxybenzyl)-1-piperazinylcarbonyl]methyl groups.

Examples of the piperazinyl lower alkanoyl group which may be substituted on the piperazine ring with a phenyl lower alkyl group which may have a lower alkylenedioxy group as a substituent on the phenyl ring include piperazinylalkanoyl groups whose alkanoyl moiety is a linear or branched alkanoyl group having 2 to 6 carbon atoms and which may be substituted on the piperazine ring with 1 to 3 phenylalkyl groups which may have a linear or branched alkylenedioxy group having 1 to 4 carbon atoms as a substituent on the phenyl ring and whose alkyl moiety is a linear or branched alkyl group having 1 to 6 carbon atoms, such as 2-[(1, 2 or 3-)piperazinyl]acetyl, 3-[(1, 2 or 3-)piperazinyl]propionyl, 2-[(1, 2 or 3-)piperazinyl]propionyl, 4-[(1, 2 or 3-)piperazinyl]butyryl, 5-[(1, 2 or 3-)piperazinyl]pentanoyl, 6-[(1, 2 or 3-)piperazinyl]hexanoyl, 2,2-dimethyl-3-[(1, 2 or 3-)piperazinyl]propionyl, 2-methyl-3-[(1, 2 or 3-)piperazinyl]propionyl, 2-(4-benzyl-1-piperazinyl)acetyl, 3-[4-(2-phenylethyl)-1-piperazinyl]propionyl, 2-[4-(3-phenylpropyl)-1-piperazinyl]propionyl, 4-[4-(4-phenylbutyl)-1-piperazinyl]butyryl, 5-[4-(5-phenylpentyl)-1-piperazinyl]pentanoyl, 6-[4-(6-phenylpropyl)-1-piperazinyl]hexanoyl, 6-(4-benzyl-1-piperazinyl)hexanoyl, 2,2-dimethyl-3-(4-benzyl-1-piperazinyl)propionyl, 2-methyl-3-(4-benzyl-1-piperazinyl)propionyl, 2-[4-(3,4-methylenedioxybenzyl)-1-piperazinyl]acetyl, 3-{4-[2-(2,3-ethylenedioxyphenyl)ethyl]-1-piperazinyl}propionyl, 2-{4-[3-(3,4-trimethylenedioxyphenyl)propyl]-1-piperazinyl}propionyl, 4-{4-[4-(2,3-tetramethylenedioxyphenyl)butyl]-1-piperazinyl}butyryl, 5-{4-[5-(3,4-methylenedioxyphenyl)pentyl]-1-piperazinyl}pentanoyl, 5-{4-[3-(2,3-ethylenedioxyphenyl)propyl]-1-piperazinyl}pentanoyl, 6-[4-(3,4-trimethylenedioxybenzyl)-1-piperazinyl]hexanoyl, 2,2-dimethyl-3-[4-(2,3-tetramethylenedioxybenzyl)-1-piperazinyl]propionyl, 2-methyl-3-[4-(3,4-methylenedioxybenzyl)-1-piperazinyl]propionyl, 2-(3,4-dibenzyl-1-2-(3,4,5-tribenzyl-1-piperazinyl)acetyl, 2-[2,4-di(3,4-methylenedioxybenzyl)-1-piperazinyl]acetyl, 2-[2,4,6-tri(3,4-methylenedioxybenzyl)-1-piperazinyl]acetyl, and 2-[3-benzyl-4-(3,4-methylenedioxybenzyl)-1-piperazinyl]acetyl groups.

Examples of the morpholinocarbonyl substituted lower alkyl group include morpholinocarbonylalkyl groups whose alkyl moiety is a linear or branched alkyl group having 1 to 6 carbon atoms such as [(2, 3 or 4-)morpholino]carbonylmethyl, 2-[(2, 3 or 4-)morpholino]carbonylethyl, 1-[(2, 3 or 4-)morpholino]carbonylethyl, 3-[(2, 3 or 4-)morpholino]carbonylpropyl, 4-[(2, 3 or 4-)morpholino]carbonylbutyl, 5-[(2, 3 or 4-)morpholino]carbonylpentyl, 6-[(2, 3 or 4-)morpholino]carbonylhexyl, 1,1-dimethyl-2-[(2, 3 or 4-)morpholino]carbonylethyl, and 2-methyl-3-[(2, 3 or 4-)morpholino]carbonylpropyl groups.

Examples of the imidazolyl lower alkanoyl group include imidazolylalkanoyl groups whose alkanoyl moiety is a linear or branched alkanoyl group having 2 to 6 carbon atoms such as 2-[(1, 2, 4 or 5-)imidazolyl]acetyl, 3-[(1, 2, 4 or 5-)imidazolyl]propionyl, 2-[(1, 2, 4 or 5-)imidazolyl]propionyl, 4-[(1, 2, 4 or 5-)imidazolyl]butyryl, 5-[(1, 2, 4 or 5-)imidazolyl]pentanoyl, 6-[(1, 2, 4 or 5-)imidazolyl]hexanoyl, 2,2-dimethyl-3-[(1, 2, 4 or 5-)imidazolyl]propionyl, and 2-methyl-3-[(1, 2, 4 or 5-)imidazolyl]propionyl groups.

Examples of the cycloalkylcarbonyl group include cycloalkylcarbonyl groups whose cycloalkyl moiety is a cycloalkyl group having 3 to 16 carbon atoms such as cyclopropylcarbonyl, cyclobutylcarbonyl, cyclopentylcarbonyl, cyclohexylcarbonyl, cycloheptylcarbonyl, cyclooctylcarbonyl, cyclononylcarbonyl, cyclodecylcarbonyl, cycloundecylcarbonyl, cyclododecylcarbonyl, cyclotridecylcarbonyl, cyclotetradecylcarbonyl, cyclopentadecylcarbonyl, and cyclohexadecylcarbonyl groups.

Examples of the amino substituted lower alkanoyl group which may have a lower alkyl group as a substituent include linear or branched alkanoyl groups having 2 to 6 carbon atoms substituted with an amino group which may have 1 or 2 linear or branched alkyl groups having 1 to 6 carbon atoms as substituents such as aminoacetyl, 2-aminopropionyl, 3-aminopropionyl, 4-aminobutyryl, 5-aminopentanoyl, 6-aminohexanoyl, 2,2-dimethyl-3-aminopropionyl, 2-methyl-3-aminopropionyl, methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, dimethylaminoacetyl, 3-diisopropylaminopropionyl, (N-ethyl-N-propylamino)acetyl, and 2-(N-methyl-N-hexylamino)acetyl groups.

Examples of the lower alkylene group which may have a hydroxyl group as a substituent include, in addition to the above described lower alkylene groups, linear or branched alkylene groups having 1 to 6 carbon atoms which may have 1 to 3 hydroxyl groups as substituents such as 1-hydroxymethylene, 2-hydroxyethylene, 1-hydroxyethylene, 2-hydroxytrimethylene, 3-hydroxytrimethylene, 1-hydroxytrimethylene, 3-hydroxy-2-methyltrimethylene, 1-hydroxy-2-methyltrimethylene, 3-hydroxy-2,2-dimethyltrimethylene, 1-hydroxy-2,2-dimethyltrimethylene, 3-hydroxy-1-methyltrimethylene, 2-hydroxy-1-methyltrimethylene, 1-hydroxymethylmethylene, hydroxymethylmethylene, 2-hydroxymethyltrimethylene, 2-hydroxymethyl-2-methyltrimethylene, (2-hydroxyethyl)methylene, (1-hydroxyethyl)methylene, 4-hydroxytetramethylene, 2-hydroxytetramethylene, 3-hydroxytetramethylene, 1-hydroxytetramethylene, 5-hydroxypentamethylene, 4-hydroxypentamethylene, 3-hydroxypentamethylene, 2-hydroxypentamethylene, 1-hydroxypentamethylene, 6-hydroxyhexamethylene, 5-hydroxyhexamethylene, 4-hydroxyhexamethylene, 3-hydroxyhexamethylene, 2-hydroxyhexamethylene, 1-hydroxyhexamethylene, 1,2-dihydroxytrimethylene, 2,2,4-trihydroxytetramethylene, 1,2,6-trihydroxyhexamethylene, and 3,4,5-trihydroxypentamethylene groups.

Examples of the alkyl group which may have a hydroxyl group as a substituent include, in addition to the above described lower alkyl groups, linear or branched alkyl groups having 1 to 16 carbon atoms which may have 1 to 3 hydroxyl groups as substituents such as heptyl, octyl, nonyl, decyl, undecyl, dodecyl, tridecyl, tetradecyl, pentadecyl, 1-methylhexyl, hexadecyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the hydroxyl group substituted alkyl group include linear or branched alkyl groups having 1 to 16 carbon atoms and 1 to 3 hydroxyl groups as substituents such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the cycloalkyl group which may have a substituent selected from the group consisting of a hydroxyl group and a lower alkyl group include, in addition to the above described cycloalkyl groups, cycloalkyl groups having 3 to 16 carbon atoms which may have 1 to 3 substituents selected from the group consisting of a hydroxyl group and a linear or branched alkyl group having 1 to 6 carbon atoms such as 2-hydroxycyclopropyl, 3-hydroxycyclobutyl, 3-hydroxycyclopentyl, 2-hydroxycyclohexyl, 4-hydroxycyclohexyl, 3-hydroxycycloheptyl, 4-hydroxycyclooctyl, 5-hydroxycyclononyl, 3-hydroxycyclodecyl, 4-hydroxycycloundecyl, 5-hydroxycyclododecyl, 6-hydroxycyclotridecyl, 7-hydroxycyclotetradecyl, 6-hydroxycyclopentadecyl, 8-hydroxycyclohexadecyl, 2,4-dihydroxycyclohexyl, 2,4,6-trihydroxycyclohexyl, 1-methylcyclopentyl, 2-ethylcyclopropyl, 3-n-propylcyclobutyl, 2-n-butylcyclohexyl, 4-n-pentylcycloheptyl, 4-n-hexylcyclooctyl, 2,3-dimethylcyclohexyl, 2,3,4-trimethylcyclohexyl, and 2-methyl-4-hydroxycyclohexyl groups.

Examples of the phenoxy lower alkyl group include phenoxyalkyl groups whose alkyl moiety is a linear or branched alkyl group having 1 to 6 carbon atoms such as phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl, 1-phenoxyisopropyl, and 2-methyl-3-phenoxypropyl groups.

Examples of the amino lower alkoxy group which may have a lower alkyl group as a substituent include linear or branched alkoxy groups having 1 to 6 carbon atoms substituted with an amino group which may have 1 or 2 linear or branched alkyl groups having 1 to 6 carbon atoms such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, 2-diethylaminoethoxy, 2-diisopropylaminoethoxy, (N-ethyl-N-propylamino)methoxy, and 2-(N-methyl-N-hexylamino)ethoxy groups.

Examples of the hydroxyl group substituted lower alkyl group include linear or branched alkyl groups having 1 to 6 carbon atoms which have 1 to 3 hydroxyl groups as substituents such as hydroxymethyl, 1-hydroxyethyl, 2-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the amino group which may have a lower alkylsulfonyl as a substituent include amino groups which may have 1 or 2 linear or branched alkylsulfonyl groups having 1 to 6 carbon atoms as substituents such as amino, methylsulfonylamino, ethylsulfonylamino, propylsulfonylamino, isopropylsulfonylamino, butylsulfonylamino, tert-butylsulfonylamino, pentylsulfonylamino, hexylsulfonylamino, dimethylsulfonylamino, diethylsulfonylamino, dipropylsulfonylamino, dibutylsulfonylamino, dipentylsulfonylamino, dihexylsulfonylamino, N-methylsulfonyl-N-ethylsulfonylamino, N-ethylsulfonyl-N-propylsulfonylamino, N-methylsulfonyl-N-butylsulfonylamino, and N-methylsulfonyl-N-hexylsulfonylamino groups.

Examples of the lower alkynyl group include linear or branched alkynyl groups having 2 to 6 carbon atoms such as ethynyl, 2-propynyl, 2-butynyl, 3-butynyl, 1-methyl-2-propynyl, 2-pentynyl, and 2-hexynyl groups.

Examples of the anilino group which may have a halogen atom as a substituent on the phenyl ring include anilino groups which may have 1 to 3 halogen atoms as substituents on the phenyl ring such as anilino, 2-fluoroanilino, 3-fluoroanilino, 4-fluoroanilino, 2-bromoanilino, 3-bromoanilino, 4-bromoanilino, 2-iodoanilino, 3-iodoanilino, 4-iodoanilino, 2,3-dibromoanilino, 2,4-diiodoanilino, 2,5-difluoroanilino, 2,6-dichloroanilino, 2,4,6-trichloroanilino, 2,6-difluoroanilino, 3,5-difluoroanilino, 2,6-difluoroanilino, 2-chloroanilino, 3-chloroanilino, 4-chloroanilino, 2,3-dichloroanilino, 2,4-dichloroanilino, 2,5-dichloroanilino, 3,4-dichloroanilino, 2,6-dichloroanilino, 3,5-dichloroanilino, 2,4,6-trifluoroanilino, 2,4-difluoroanilino, and 3,4-difluoroanilino groups.

Examples of the piperazinyl group which may have a lower alkyl group as a substituent on the piperazine ring include piperazinyl groups which may have 1 to 3 linear or branched alkyl groups having 1 to 6 carbon atoms as substituents on the piperazine ring such as (1-, 2- or 3-)piperazinyl, 4-methyl-(1-, 2- or 3-)piperazinyl, 2,3-dimethyl-(1- or 5-)piperazinyl, and 2,3,4-trimethyl-(1-, 5- or 6-)piperazinyl groups.

Examples of the pyrrolidinyl group which may have an oxo group as a substituent on the pyrrolidine ring include pyrrolidinyl groups which may have 1 or 2 oxo groups as substituents on the pyrrolidine ring such as (1-, 2- or 3-)pyrrolidinyl, 2-oxo-(1-, 3-, 4- or 5-)pyrrolidinyl, 3-oxo-(1-, 2-, 4- or 5-)pyrrolidinyl, 2,3-dioxo-(1-, 4- or 5-)pyrrolidinyl, and 2,5-dioxo-(1-, 3- or 4-)pyrrolidinyl groups.

Examples of the lower alkanoyl amino group include linear or branched alkanoyl amino groups having 2 to 6 carbon atoms which have 1 to 3 halogen atoms as substituents such as acetyl amino, propionyl amino, butyryl amino, pentanoyl amino, 2-methylpropionyl amino, and hexanoyl amino groups.

Examples of the phenyl group which may be substituted on the phenyl ring with 1 to 3 groups selected from the group consisting of a lower alkyl group; a lower alkoxy group which may have a halogen atom as a substituent; a halogen atom; an amino lower alkoxy group which may have a lower alkyl group as a substituent; a hydroxyl group substituted lower alkyl group; a phenyl lower alkyl group; a lower alkynyl group; an amino group which may have a lower alkylsulfonyl group as a substituent; a lower alkylthio group; a cycloalkyl group; a phenylthio group; an adamantyl group; an anilino group which may have a halogen atom as a substituent on the phenyl ring; a lower alkoxycarbonyl group; a piperazinyl group which may have a lower alkyl group as a substituent on the piperazine ring; a lower alkanoylamino group; a cyano group; a pyrrolidinyl group which may have an oxo group as a substituent on the pyrrolidine ring; and a phenoxy group include phenyl groups which may be substituted on the phenyl ring with 1 to 3 groups selected from the group consisting of a linear or branched alkyl group having 1 to 6 carbon atoms; a linear or branched alkoxy group having 1 to 6 carbon atoms which may have 1 to 3 halogen atoms; a halogen atom; an aminoalkoxy group whose alkoxy moiety is a linear or branched alkoxy group having 1 to 6 carbon atoms and which may have 1 or 2 linear or branched alkyl groups having 1 to 6 carbon atom as substituents; a linear or branched alkyl group having 1 to 6 carbon atoms and 1 to 3 hydroxyl groups as substituents; a phenylalkyl group whose alkyl moiety is a linear or branched alkyl group having 1 to 6 carbon atoms; a linear or branched alkynyl group having 2 to 6 carbon atoms; an amino group which may have 1 or 2 linear or branched alkylsulfonyl groups having 1 to 6 carbon atoms as substituents; a linear or branched alkylthio group having 1 to 6 carbon atoms; a cycloalkyl group having 3 to 16 carbon atoms; a phenylthio group; an adamantyl group; an anilino group which may have 1 to 3 halogen atoms as substituents on the phenyl ring; an alkoxycarbonyl group whose akloxy moiety is a linear or branched alkoxy group having 1 to 6 carbon atoms; an amino group which may have 1 or 2 linear or branched alkanoyl groups having 2 to 6 carbon atoms; a cyano group; a piperazinyl group which may have 1 to 3 linear or branched alkyl groups having 1 to 6 carbon atoms as substituents on the piperazine ring; a pyrrolidinyl group which may have 1 or 2 oxo groups as substituents on the pyrrolidine ring; and a phenoxy group such as phenyl, 2-methylphenyl, 3-methylphenyl, 4-methylphenyl, 2-ethylphenyl, 3-ethylphenyl, 4-ethylphenyl, 2-isopropylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethyiphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-methyl-3-trifluoromethoxy-4-trifluoromethoxyphenyl, 2-phenoxyphenyl, 3-phenoxyphenyl, 4-phenoxyphenyl, 2,3-diphenoxyphenyl, 3,4-diphenoxyphenyl, 2,6-diphenoxyphenyl, 3,4,5-triphenoxyphenyl, 2-methyl-4-phenoxyphenyl, 3-ethyl-4-phenoxyphenyl, 2-methoxy-4-phenoxyphenyl, 3-ethoxy-4-phenoxyphenyl, 2-methyl-3-phenoxy-4-trifluoromethoxyphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 4-methylthiophenyl, 4-cyclohexylphenyl, 4-chloro-2-anilinophenyl, 2-(4-chloro anilino)-5-ethoxy carbonylphenyl, 4-[2-(N,N-diethylamino) ethoxy]phenyl, 4-(4-methyl-1-piperazinyl)phenyl, 4-(2-oxo-1-pyrrolidinyl)phenyl, 4-methylsulfonylaminophenyl, 4-(2-hydroxyethyl)phenyl, 4-benzylphenyl, 4-ethynylphenyl, 4-phenylthiophenyl, 4-(1-adamantyl)phenyl, 5-acetylamino-2-chlorophenyl, 2-propanoylaminophenyl, 3-cyanophenyl, 2-cyanophenyl, 4-cyanophenyl, 3,4-dicyanophenyl, and 3,4,5-tricyanophenyl groups.

Examples of the phenyl lower alkyl group which may be substituted on the phenyl ring with 1 to 3 groups selected from the group consisting of a halogen atom, a lower alkoxy group which may have a halogen atom as a substituent, and a lower alkyl group include, in addition to the above described phenyl lower alkyl groups, phenylalkyl groups whose alkyl moiety is a linear or branched alkyl group having 1 to 6 carbon atoms and which may be substituted on the phenyl ring with 1 to 3 groups selected from the group consisting of a halogen atom, a linear or branched alkoxy group having 1 to 6 carbon atoms which may have 1 to 3 halogen atoms as substituents, and a linear or branched alkyl group having 1 to 6 carbon atoms such as 4-fluorobenzyl, 2-chlorobenzyl, 3-chlorobenzyl, 4-chlorobenzyl, 2-(2-fluorophenyl)ethyl, 2-(4-fluorophenyl) ethyl, 2-(4-chlorophenyl)ethyl, 3,4-dibromobenzyl, 3,4-diiodobenzyl, 2,4-difluorobenzyl, 2,5-dichlorobenzyl, 2,6-dichlorobenzyl, 3,4,5-trifluorobenzyl, 3-(4-chlorophenyl)propyl, 1-(2-bromophenyl)ethyl, 4-(3-fluorophenyl)butyl, 5-(4-iodophenyl)pentyl, 6-(4-chlorophenyl)hexyl, 1,1-dimethyl-2-(3-fluorophenyl)ethyl, 2-methyl-3-(4-chlorophenyl)propyl, 2-methylbenzyl, 2-(3-methylphenyl)ethyl, 3-(4-methylphenyl)propyl, 1-(2-ethylphenyl)ethyl, 4-(3-ethylphenyl)butyl, 5-(4-ethylphenyl)pentyl, 6-(4-isopropylphenyl)hexyl, 1,1-dimethyl-2-(3-butylphenyl) ethyl, 2-methyl-3-(4-pentylphenyl)propyl, 4-hexylbenzyl, 3,4-dimethylbenzyl, 3,4-diethylbenzyl, 2,4-dimethylbenzyl, 2,5-dimethylbenzyl, 2,6-dimethylbenzyl, 3,4,5-trimethylbenzyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl) propyl, 4-(4-ethoxyphenyl)butyl, 5-(4-isopropoxyphenyl) pentyl, 6-(3-butoxyphenyl)hexyl, 1,1-dimethyl-2-(4-pentyloxyphenyl)ethyl, 2-methyl-3-(4-hexyloxyphenyl) propyl, 3,4-dimethoxybenzyl, 3,4-diethoxybenzyl, 2,4-dimethoxybenzyl, 2,5-dimethoxybenzyl, 2,6-dimethoxybenzyl, 3,4,5-trimethoxybenzyl, 2-trifluoromethoxybenzyl, 3-trifluoromethoxybenzyl, 4-trifluoromethoxybenzyl, 2-[2-(bromomethoxy)phenyl]ethyl, 1-[3-(2-chloroethoxy)phenyl]ethyl, 3-[4-(2,3-dichloropropoxy)phenyl]propyl, 4-[4-(4-fluorobutoxy)phenyl]butyl, 5-[3-(5-chloropentyloxy)phenyl]pentyl, 6-[4-(5-bromohexyloxy)phenyl]hexyl, 1,1-dimethyl-2-[4-(5,6-dibromohexyloxy)phenyl]ethyl, 3,4-di(trifluoromethoxy)benzyl, 3,4-di(4,4,4-trichlorobutoxy)benzyl, 2,4-di(3-chloro-2-methoxypropyl)benzyl, 2,5-di(3-chloropropoxy)benzyl, 2,6-di(2,2,2-trifluoroethoxy)benzyl, 3,4,5-tri(trifluoromethoxy) benzyl, 4-(2,2,2-trichloroethoxy)benzyl, 2-methyl-4-trifluoromethoxybenzyl, 3-ethyl-4-trichloromethoxybenzyl, 2-methoxy-4-trifluoromethoxybenzyl, 3-ethoxy-4-trichloromethoxybenzyl, 2-methyl-3-trifluoromethoxy-4-trifluoromethoxybenzyl, 2-chloro-3-methylbenzyl, 4-fluoro-2-trifluoromethoxybenzyl, and 3-chloro-2-methyl-4-methoxybenzyl groups.

Examples of the phenyl lower alkyl group which has a lower alkylenedioxy group as a substituent on the phenyl ring include phenylalkyl groups which have a linear or branched alkylenedioxy group having 1 to 4 carbon atoms as a substituent on the phenyl ring and whose alkyl moiety is a linear or branched alkyl group having 1 to 6 carbon atoms such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-metylenedioxyphenyflethyl, and 2-methyl-3-(3,4-ethylenedioxyphenyl)propyl groups.

Examples of the amino group which may have a lower alkanoyl group as a substituent include amino groups which may have a linear or branched alkanoyl group having 1 to 6 carbon atoms as a substituent such as amino, N-acetylamino, N-formylamino, N-propionylamino, N-butyrylamino, N-isobutyrylamino, N-pentanoylamino, N-tert-butylcarbonylamino, and N-hexanoylamino groups.

Examples of the 1,2,3,4-tetrahydroquinolyl group which may have, on the tetrahydroquinoline ring, 1 to 3 substituents selected from the group consisting of an oxo group, a lower alkoxy group, and a lower alkylenedioxy group include 1,2,3,4-tetrahydroquinolyl groups which may have, on the tetrahydroquinoline ring, 1 to 3 substituents selected from the group consisting of an oxo group, a linear or branched alkoxy group having 1 to 6 carbon atoms, and a linear or branched alkylenedioxy group having 1 to 4 carbon atoms such as (1, 2, 3, 4, 5, 6, 7 or 8-)1,2,3,4-tetrahydroquinolyl, 2-oxo-(1, 3, 4, 5, 6, 7 or 8-)1,2,3,4-tetrahydroquinolyl, 2-oxo-6,7-methylenedioxy-(1, 3, 4, 5 or 8-)1,2,3,4-tetrahydroquinolyl, 4-oxo-(1, 2, 3, 5, 6, 7 or 8-)1,2,3,4-tetrahydroquinolyl, 2,4-dioxo-(1, 3, 5, 6, 7 or 8-)1,2,3,4-tetrahydroquinolyl, 2,4-dioxo-6,7-methylenedioxy-(1, 3, 5 or 8-)1,2,3,4-tetrahydroquinolyl, 5,6-ethylenedioxy-(1, 2, 3, 4, 7 or 8-)1,2,3,4-tetrahydroquinolyl, 7,8-trimethylenedioxy-(1, 2, 3, 4, 5 or 6-)1,2,3,4-tetrahydroquinolyl, 6,7-tetramethylenedioxy-(1, 2, 3, 4, 5 or 8-)1,2,3,4-tetrahydroquinolyl, 5-methoxy-2-oxo-(1, 3, 4, 6, 7 or 8-)1,2,3,4-tetrahydroquinolyl, and 2-oxo-6,7-ethylenedioxy-(1, 3, 4, 5 or 8-)1,2,3,4-tetrahydroquinolyl groups.

Examples of the cycloalkyl lower alkyl group include cycloalkylalkyl groups having 3 to 16 carbon atoms whose alkyl moiety is a linear or branched alkyl group having 1 to 6 carbon atoms such as cyclopropylmethyl, cyclohexylmethyl, 2-cyclopropylethyl, 1-cyclobutylethyl, 3-cyclopentylpropyl, 4-cyclohexylbutyl, 5-cycloheptylpentyl, 6-cyclooctylhexyl, 1,1-dimethyl-2-cyclononylethyl, 2-methyl-3-cyclodecylpropyl, cycloundecylmethyl, 2-cyclododecylethyl, 1-cyclotridecylethyl, 3-cyclotetradecylpropyl, 4-cyclopentadecylbutyl, and 5-cyclohexadecylpentyl groups.

Examples of the pyridyl lower alkyl group include pyridylalkyl groups whose alkyl moiety is a linear or branched alkyl group having 1 to 6 carbon atoms such as (2, 3 or 4-)pyridylmethyl, 2-[(2, 3 or 4-)pyridyl]ethyl, 1-[(2, 3 or 4-)pyridyl]ethyl, 3-[(2, 3 or 4-)pyridyl]propyl, 4-[(2, 3 or 4-)pyridyl]butyl, 1,1-dimethyl-2-[(2, 3 or 4-)pyridyl]ethyl, 5-[(2, 3 or 4-)pyridyl]pentyl, 6-[(2, 3 or 4-)pyridyl]hexyl, 1-[(2, 3 or 4-)pyridyl]isopropyl, and 2-methyl-3-[(2, 3 or 4-)pyridyl]propyl groups.

Examples of the amino group substituted lower alkyl group which may have a substituent selected from the group consisting of a lower alkyl group and a lower alkanoyl group include linear or branched alkyl groups having 1 to 6 carbon atoms and an amino group which may have 1 or 2 substituents selected from the group consisting of a linear or branched alkyl group having 1 to 6 carbon atoms and a linear or branched alkanoyl group having 1 to 6 carbon atoms such as aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N,N-dimethylamino)ethyl, 2-(N-methyl-N-hexylamino)ethyl, formylaminomethyl, acetylaminomethyl, 1-propionylaminoethyl, 2-acetylaminoethyl, 3-butyrylaminopropyl, 4-pentanoylaminobutyl, 5-hexanoylaminopentyl, 6-acetylaminohexyl, N-methyl-N-acetylaminomethyl, 2-(N-ethyl-N-propanoylamino)ethyl, (N-ethyl-N-butyrylamino)methyl, 2-(N-methyl-N-hexanoylamino)ethyl, and 3-(N,N-dimethylamino) propyl groups.

Examples of the lower alkoxy lower alkyl group include linear or branched alkyl groups having 1 to 6 carbon atoms which have a linear or branched alkoxy group having 1 to 6 carbon atoms, as a substituent such as methoxymethyl, 1-ethoxyethyl, 2-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups.

Examples of the 1,2,3,4-tetrahydroisoquinolylcarbonyl substituted lower alkyl group include 1,2,3,4-tetrahydroisoquinolylcarbonyl-alkyl groups whose alkyl moiety is a linear or branched alkyl group having 1 to 6 carbon atoms such as (1, 2, 3, 4, 5, 6, 7 or 8-)1,2,3,4-tetrahydroisoquinolylcarbonylmethyl, 2-[(1, 2, 3, 4, 5, 6, 7 or 8-)1,2,3,4-tetrahydroisoquinolylcarbonyl]ethyl, 1-[((1, 2, 3, 4, 5, 6, 7 or 8-)1,2,3,4-tetrahydroisoquinolylcarbonyl)ethyl, 3-[(1, 2, 3, 4, 5, 6, 7 or 8-)1,2,3,4-tetrahydroisoquinolylcarbonyl]propyl, 4-[(1, 2, 3, 4, 5, 6, 7 or 8-)1,2,3,4-tetrahydroisoquinolylcarbonyl]butyl, 1,1-dimethyl-2-[(1, 2, 3, 4, 5, 6, 7 or 8-)1,2,3,4-tetrahydroisoquinolylcarbonyl]ethyl, 5-[(1, 2, 3, 4, 5, 6, 7 or 8-)1,2,3,4-tetrahydroisoquinolylcarbonyl]pentyl, 6-[(1, 2, 3, 4, 5, 6, 7 or 8-)1,2,3,4-tetrahydroisoquinolylcarbonyl]hexyl, 1-[(1, 2, 3, 4, 5, 6, 7 or 8-)1,2,3,4-tetrahydroisoquinolylcarbonyl]isopropyl, and 2-methyl-3-[(1, 2, 3, 4, 5, 6, 7 or 8-)1,2,3,4-tetrahydroisoquinolylcarbonyl]propyl groups.

Examples of the piperidinylcarbonyl group which may have, on the piperidine ring, a substituent selected from the group consisting of a lower alkoxycarbonyl group, a phenyl lower alkyl group, and a furyl lower alkyl group include piperidinylcarbonyl groups which may have, on the piperidine ring, 1 to 3 substituents selected from the group consisting of an alkoxycarbonyl group whose alkoxy moiety is a linear or branched alkoxy group having 1 to 6 carbon atoms, a phenylalkyl group whose alkyl moiety is a linear or branched alkyl group having 1 to 6 carbon atoms, and a furylalkyl group whose alkyl moiety is a linear or branched alkyl group having 1 to 6 carbon atoms such as (1, 2, 3 or 4-)piperidinylcarbonyl, 1-benzyl-(2, 3 or 4-)piperidinylcarbonyl, 1-(2 or 3-)furylmethyl-(2, 3 or 4-)piperidinylcarbonyl, 1-(2-phenylethyl)-(2, 3 or 4-)piperidinylcarbonyl, 1-{2-[(1 or 2-)furyl]ethyl}-(2, 3 or 4-)piperidinylcarbonyl, 1-(1-phenylethyl)-(2, 3 or 4-)piperidinylcarbonyl, 1-{3-[(1 or 2-)furyl]propyl]}-(2, 3 or 4-)piperidinylcarbonyl, 1-(3-phenylpropyl)-(2, 3 or 4-)piperidinylcarbonyl, 1-{1-[(1 or 2-)furyl]ethyl]}-(2, 3 or 4-)piperidinylcarbonyl, 1-(4-phenylbutyl)-(2, 3 or 4-)piperidinylcarbonyl, 1-{4-[(1 or 2-)furyl]butyl]}-(2, 3 or 4-)piperidinylcarbonyl, 1-(5-phenylpentyl)-(2, 3 or 4-)piperidinylcarbonyl, 1-{5-[(1 or 2-)furyl]pentyl]}-(2, 3 or 4-)piperidinylcarbonyl, 1-(6-phenylhexyl)-(2, 3 or 4-)piperidinylcarbonyl, 1-{6-[(1 or 2-)furyl]hexyl]}-(2, 3 or 4-)piperidinylcarbonyl, 1,2-dibenzyl-(3, 4, 5 or 6-)piperidinylcarbonyl, 1,3-di(1 or 2-)furylmethyl-(2, 4, 5 or 6-)piperidinylcarbonyl, 1,3,5-tribenzyl-(2, 4 or 6-)piperidinylcarbonyl, 1,2,6-tri(1 or 2-)furylmethyl-(3, 4 or 5-)piperidinylcarbonyl, 1-benzyl-3-(1 or 2-)furylmethyl-(2, 4, 5 or 6-)piperidinylcarbonyl, 1-{1-[(1 or 2-)furyl]ethyl]}-(2, 3 or 4-)piperidinylcarbonyl, 1-methoxycarbonyl-(2, 3 or 4-)piperidinylcarbonyl, 1-ethoxycarbonyl-(2, 3 or 4-)piperidinylcarbonyl, 1-propoxycarbonyl-(2, 3 or 4-)piperidinylcarbonyl, 1-butoxycarbonyl-(2, 3 or 4-)piperidinylcarbonyl, 1-tert-butoxycarbonyl-(2, 3 or 4-)piperidinylcarbonyl, 1-pentyloxycarbonyl-(2, 3 or 4-)piperidinylcarbonyl, 1-hexyloxycarbonyl-(2, 3 or 4-)piperidinylcarbonyl, 1,2-dimethoxycarbonyl-(3, 4, 5 or 6-)piperidinylcarbonyl, 1,2,6-triethoxycarbonyl-(3, 4 or 5-)piperidinylcarbonyl, 1-(1 or 2-)furylmethyl-3-tert-butoxycarbonyl-(3, 4, 5 or 6-)piperidinylcarbonyl, 1-benzyl-2-methoxycarbonyl-(2, 4, 5 or 6-)piperidinylcarbonyl, and 1-(1 or 2-)furylmethyl-2,4-dimethoxycarbonyl-(3, 5 or 6-)piperidinylcarbonyl groups.

Examples of the thiazolidinyl lower alkanoyl group which may have an oxo group as a substituent on the thiazolidine ring include thiazolidinylalkanoyl groups which may have 1 to 3 oxo groups as substituents on the thiazolidine ring and whose alkanoyl moiety is a linear or branched alkanoyl group having 2 to 6 carbon atoms such as 2-[(2, 3, 4 or 5-)thiazolidinyl]acetyl, 3-[(2, 3, 4 or 5-)thiazolidinyl]propionyl, 2-[(2, 3, 4 or 5-)thiazolidinyl]propionyl, 4-[(2, 3, 4 or 5-)thiazolidinyl]butyryl, 5-[(2, 3, 4 or 5-)1,2,4-thiazolidinyl]pentanoyl, 6-[(2, 3, 4 or 5-)thiazolidinyl]hexanoyl, 2,2-dimethyl-3-[(2, 3, 4 or 5-)thiazolidinyl]propionyl, 2-methyl-3-[(2, 3, 4 or 5-)thiazolidinyl]propionyl, 2,4-dioxo-(3 or 5-)thiazolidinylacetyl, 3-[2-oxo-(3, 4 or 5-)thiazolidinyl]propionyl, 2-[4-oxo-(2, 3 or 5-)thiazolidinyl]propionyl, 4-[5-oxo-(2, 3 or 4-)thiazolidinyl]butyryl, 5-[2,5-dioxo-(3 or 4-)thiazolidinyl]pentanoyl, 6-[2,4,5-trioxo-3-thiazolidinyl]hexanoyl, 2-[4,5-dioxo-(2 or 3-)thiazolidinyl]acetyl, 2,2-dimethyl-3-[2,4-dioxo-(3 or 5-)thiazolidinyl]propionyl, and 2-methyl-3-[2,4-dioxo-(3 or 5-)thiazolidinyl]propionyl groups.

Examples of the piperidinyl group which may be substituted on the piperidine ring with a group selected from the group consisting of a lower alkoxycarbonyl group, a phenyl lower alkyl group, a lower alkyl group, a benzoyl group and a furyl lower alkyl group include piperidinyl groups which may be substituted on the piperidine ring with 1 to 3 groups selected from the group consisting of an alkoxycarbonyl group whose alkoxy moiety is a linear or branched alkoxy group having 1 to 6 carbon atoms, a phenylalkyl group whose alkyl moiety is a linear or branched alkyl group having 1 to 6 carbon atoms, a linear or branched alkyl group having 1 to 6 carbon atoms, a benzoyl group, and a furylalkyl group whose alkyl moiety is a linear or branched alkyl group having 1 to 6 carbon atoms such as (1, 2, 3 or 4-)piperidinyl, 1-benzyl-(2, 3 or 4-)piperidinyl, 1-(2 or 3-)furylmethyl-(2, 3 or 4-)piperidinyl, 1-(2-phenylethyl)-(2, 3 or 4-)piperidinyl, 1-{2-[(1 or 2-)furyl]ethyl}-(2, 3 or 4-)piperidinyl, 1-(1-phenylethyl)-(2, 3 or 4-)piperidinyl, 1-{3-[(1 or 2-)furyl]propyl]}-(2, 3 or 4-)piperidinyl, 1-(3-phenylpropyl)-(2, 3 or 4-)piperidinyl, 1-{1-[(1 or 2-)furyl]ethyl]}-(2, 3 or 4-)piperidinyl, 1-(4-phenylbutyl)-(2, 3 or 4-)piperidinyl, 1-{4-[(1 or 2-)furyl]butyl]}-(2, 3 or 4-)piperidinyl, 1-(5-phenylpentyl)-(2, 3 or 4-)piperidinyl, 1-{5-[(1 or 2-)furyl]pentyl]}-(2, 3 or 4-)piperidinyl, 1-(6-phenylhexyl)-(2, 3 or 4-)piperidinyl, 1-{6-[(1 or 2-)furyl]hexyl]}-(2, 3 or 4-)piperidinyl, 1,2-dibenzyl-(3, 4, 5 or 6-)piperidinyl, 1,3-di(1 or 2-)furylmethyl-(2, 4, 5 or 6-)piperidinyl, 1,3,5-tribenzyl-(2, 4 or 6-)piperidinyl, 1,2,6-tri(1 or 2-)furylmethyl-(3, 4 or 5-)piperidinyl, 1-benzyl-3-(1 or 2-)furylmethyl-(2, 4, 5 or 6-)piperidinyl, 1-{1-[(1 or 2-)furyl]ethyl]}-(2, 3 or 4-)piperidinyl, 1-benzoyl-(2, 3 or 4-)piperidinyl, 1,2-dibenzoyl-(3, 4, 5 or 6-)piperidinyl, 1,3,5-tribenzoyl-(2, 4 or 6-)piperidinyl, 1-methyl-(2, 3 or 4-)piperidinyl, 1-ethyl-(2, 3 or 4-)piperidinyl, 1-propyl-(2, 3 or 4-)piperidinyl, 1-isopropyl-(2, 3 or 4-)piperidinyl, 1-butyl-(2, 3 or 4-)piperidinyl, 1-isobutyl-(2, 3 or 4-)piperidinyl, 1-tert-butyl-(2, 3 or 4-)piperidinyl, 1-pentyl-(2, 3 or 4-)piperidinyl, 1-hexyl-(2, 3 or 4-)piperidinyl, 1,2-dimethyl-(3, 4, 5 or 6-)piperidinyl, 1,2,6-trimethyl-(3, 4 or 5-)piperidinyl, 1-methyl-3-benzyl-(3, 4, 5 or 6-)piperidinyl, 1-benzoyl-2-methyl-(2, 4, 5 or 6-)piperidinyl, 1-(1 or 2-)furylmethyl-2,4-dimethyl-(3, 5 or 6-)piperidinyl, 1-methoxycarbonyl-(2, 3 or 4-)piperidinyl, 1-ethoxycarbonyl-(2, 3 or 4-)piperidinyl, 1-propoxycarbonyl-(2, 3 or 4-)piperidinyl, 1-butoxycarbonyl-(2, 3 or 4-)piperidinyl, 1-tert-butoxycarbonyl-(2, 3 or 4-)piperidinyl, 1-pentyloxycarbonyl-(2, 3 or 4-)piperidinyl, 1-hexyloxycarbonyl-(2, 3 or 4-)piperidinyl, 1,2-dimethoxycarbonyl-(3, 4, 5 or 6-)piperidinyl, 1,2,6-triethoxycarbonyl-(3, 4 or 5-)piperidinyl, 1-methyl-3-tert-butoxycarbonyl-(3, 4, 5 or 6-)piperidinyl, 1-benzoyl-2-methoxycarbonyl-(2, 4, 5 or 6-)piperidinyl, 1-(1 or 2-)furylmethyl-2,4-dimethoxycarbonyl-(3, 5 or 6-)piperidinyl, and 1-benzyl-2,4-dimethoxycarbonyl-(3, 5 or 6-)piperidinyl groups.

Examples of the carbonyl lower alkyl group substituted with a group:

[Formula 54]

(hereinafter called "A group") include A group substituted carbonylalkyl groups whose alkyl moiety is a linear or branched alkyl group having 1 to 6 carbon atoms such as A group substituted carbonylmethyl, 2-A group substituted carbonylethyl, 1-A group substituted carbonylethyl, 3-A group substituted carbonylpropyl, 4-A group substituted carbonylbutyl, 1,1-dimethyl-2-A group substituted carbonylethyl, 5-A group substituted carbonylpentyl, 6-A group substituted carbonylhexyl, 1-A group substituted carbonylisopropyl, and 2-methyl-3-A group substituted carbonylpropyl groups.

Examples of the carbonyl lower alkyl group substituted with a group:

[Formula 55]

wherein $R^{34}$ is an oxo group or a phenyl group, and d is an integer of 0 to 3 (hereinafter called "B group"), include B group substituted carbonylalkyl groups whose alkyl moiety is a linear or branched alkyl group having 1 to 6 carbon atoms such as B group substituted carbonylmethyl, 2-B group substituted carbonylethyl, 1-B group substituted carbonylethyl, 3-B group substituted carbonylpropyl, 4-B group substituted carbonylbutyl, 1,1-dimethyl-2-B group substituted carbonylethyl, 5-B group substituted carbonylpentyl, 6-B group substituted carbonylhexyl, 1-B group substituted carbonylisopropyl, and 2-methyl-3-B group substituted carbonylpropyl groups.

Examples of the pyrrolidinyl lower alkyl group include pyrrolidinylalkyl groups whose alkyl moiety is a linear or branched alkyl group having 1 to 6 carbon atoms such as (1-, 2-, or 3-)pyrrolidinylmethyl, 2-[(1-, 2-, or 3-)pyrrolidinyl]ethyl, 1-[(1-, 2-, or 3-)pyrrolidinyl]ethyl, 3-[(1-, 2-, or 3-)pyrrolidinyl]propyl, 4-[(1-, 2-, or 3-)pyrrolidinyl]butyl, 5-[(1-, 2-, or 3-)pyrrolidinyl]pentyl, 6-[(1-, 2-, or 3-)pyrrolidinyl]hexyl, 1,1-dimethyl-2-[(1-, 2-, or 3-)pyrrolidinyl]ethyl, and 2-methyl-3-[(1-, 2-, or 3-)pyrrolidinyl]propyl groups.

Examples of the morpholino lower alkyl group include morpholinoalkyl groups whose alkyl moiety is a linear or branched alkyl group having 1 to 6 carbon atoms such as (2-, 3- or 4-)morpholinomethyl, 2-[(2-, 3- or 4-)morpholino]ethyl, 1-[(2-, 3- or 4-)morpholino]ethyl, 3-[(2-, 3- or 4-)morpholino]propyl, 4-[(2-, 3- or 4-)morpholino]butyl, 5-[(2-, 3- or 4-)morpholino]pentyl, 6-[(2-, 3- or 4-)morpholino]hexyl, 1,1-dimethyl-2-[(2-, 3- or 4-)morpholino]ethyl, and 2-methyl-3-[(2-, 3- or 4-)morpholino]propyl groups.

Examples of the phenyl lower alkenyl group include phenylalkenyl groups whose alkenyl moiety is a linear or branched alkenyl group having 2 to 6 carbon atoms and which have 1 to 3 double bonds such as styryl, 3-phenyl-2-propenyl group (trivial name: cinnamyl group), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl, and 6-phenyl-1,3,5-hexatrienyl groups.

Examples of the anilinocarbonyl lower alkyl group which may have a lower alkyl group as a substituent on the phenyl ring include anilinocarbonylalkyl groups whose alkyl moiety is a linear or branched alkyl group having 1 to 6 carbon atoms and which may have 1 to 3 linear or branched alkyl groups having 1 to 6 carbon atoms as substituents on the phenyl ring such as anilinocarbonylmethyl, 2-anilinocarbonylethyl, 1-anilinocarbonylethyl, 3-anilinocarbonylpropyl, 4-anilinocarbonylbutyl, 5-anilinocarbonylpentyl, 6-anilinocarbonylhexyl, 1,1-dimethyl-2-anilinocarbonylethyl, 2-methyl-3-anilinocarbonylpropyl, (4-methylanilinocarbonyl)methyl, 2-(3-methylanilinocarbonyl)ethyl, 3-(4-methylanilinocarbonyl)propyl, 1-(2-ethylanilinocarbonyl)ethyl, 4-(3-ethylanilinocarbonyl)butyl, 5-(4-ethylanilinocarbonyl)pentyl, 6-(4-isopropylanilinocarbonyl)hexyl, 1,1-dimethyl-2-(3-butylanilinocarbonyl)ethyl, 2-methyl-3-(4-pentylanilinocarbonyl)propyl, 4-hexylanilinocarbonylmethyl, 3,4-dimethylanilinocarbonylmethyl, 3,4-diethylanilinocarbonylmethyl, 2,4-dimethylanilinocarbonylmethyl, 2,5-dimethylanilinocarbonylmethyl, 2,6-dimethylanilinocarbonylmethyl, and 3,4,5-trimethylanilinocarbonylmethyl groups.

Examples of the piperazinyl lower alkyl group which may have, on the piperazine ring, a substituent selected from the group consisting of a lower alkyl group and a phenyl lower alkyl group which may have a lower alkylenedioxy group as a substituent on the phenyl ring include piperazinylalkyl groups whose alkyl moiety is a linear or branched alkyl group having 1 to 6 carbon atoms and which may have, on the piperazine ring, 1 to 3 substituents selected from the group consisting of a linear or branched alkyl group having 1 to 6 carbon atoms and a phenylalkyl group which may have a linear or branched alkylenedioxy group having 1 to 4 carbon atoms as a substituent on the phenyl ring and whose alkyl moiety is a linear or branched alkyl group having 1 to 6 carbon atoms such as [(1-, 2- or 3-)piperazinyl]methyl, 2-[(1-, 2- or 3-)piperazinyl]ethyl, 1-[(1-, 2- or 3-)piperazinyl]ethyl, 3-[(1-, 2- or 3-)piperazinyl]propyl, 4-[(1-, 2- or 3-)piperazinyl]butyl, 5-[(1-, 2- or 3-)piperazinyl]pentyl, 6-[(1-, 2- or 3-)piperazinyl]hexyl, 1,1-dimethyl-2-[(1-, 2- or 3-)piperazinyl]ethyl, 2-methyl-3-[(1-, 2- or 3-)piperazinyl]propyl, [1-methyl-(2-, 3- or 4-)piperazinyl]methyl, 2-[1-ethyl-(2-, 3- or 4-)piperazinyl]ethyl, 1-[4-propyl-(1-, 2- or 3-)piperazinyl]ethyl, 3-[3-isopropyl-(1-, 2-, 4-, 5- or 6-)piperazinyl]propyl, 4-[2-butyl-(1-, 3-, 4-, 5- or 6-)piperazinyl]butyl, 5-[1-isobutyl-(2-, 3- or 4-)piperazinyl]pentyl, 3-[4-methyl-(1-, 2- or 3-)piperazinyl]propyl, 6-[1-tert-butyl-(2-, 3- or 4-)piperazinyl]hexyl, 1,1-dimethyl-2-[4-pentyl-(1-, 2- or 3-)piperazinyl]ethyl, [1,2-dimethyl-(3-, 4-, 5- or 6-)piperazinyl]methyl, [1,2,6-trimethyl-(3-, 4- or 5-)piperazinyl]methyl, and 2-[4-(3,4-methylenedioxybenzyl)-(1-, 2- or 3-)piperazinyl]ethyl groups.

Examples of the amidino lower alkyl group which may have a lower alkyl group as a substituent include amidinoalkyl groups whose alkyl moiety is a linear or branched alkyl group having 1 to 6 carbon atoms and which may have 1 or 2 linear or branched alkyl groups having 1 to 6 carbon atoms as substituents such as amidinomethyl, 2-amidinoethyl, 1-amidinoethyl, 3-amidinopropyl, 4-amidinobutyl, 5-amidinopentyl, 6-amidinohexyl, 1,1-dimethyl-2-amidinoethyl, 2-methyl-3-amidinopropyl, N,N-dimethylamidinomethyl, 2-(N,N-dimethylamidino)ethyl, 1-(N-methylamidino)ethyl, 3-(N-ethylamidino)propyl, 4-(N-n-propylamidino)propyl, 5-(N-n-pentylamidino)pentyl, 6-(N-n-hexylamidino)hexyl, and (N-methyl-N-ethylamidino)methyl groups.

Examples of the carbazolyl group which may have a lower alkyl group as a substituent on the carbazole ring include carbazolyl groups which may have 1 to 3 linear or branched alkyl groups having 1 to 6 carbon atoms as substituents on the carbazole ring such as (1-, 2-, 3- or 4-)carbazolyl, 9-methyl-(1-, 2-, 3- or 4-)carbazolyl, 9-ethyl-(1-, 2-, 3- or 4-)carbazolyl, 1-ethyl-(2-, 3-, 4-, 5-, 6-, 7-, 8- or 9-)carbazolyl, 2-n-propyl-(1-, 3-, 4-, 5-, 6-, 8- or 9-)carbazolyl, 3-n-butyl-(1-, 2-, 4-, 5-, 6-, 7-, 8- or 9-)carbazolyl, 4-n-pentyl-(1-, 2-, 3-, 5-, 6-, 7-, 8- or 9-)carbazolyl, 5-n-hexyl-(1-, 2-, 3-, 4-, 6-, 7-, 8- or 9-)carbazolyl, 6,9-dimethyl-(1-, 2-, 3-, 4-, 5-, 7- or 8-)carbazolyl, and 1,7,8-trityl-(2-, 3-, 4-, 5-, 6-, 7-, 8- or 9-)carbazolyl groups.

Examples of the amidino group which may have a lower alkyl group as a substituent include amidino groups which may have 1 or 2 linear or branched alkyl groups having 1 to 6 carbon atoms as substituents such as amidino, N,N-dimethylamidino, N-methylamidino, N-ethylamidino, N-n-propylamidino, N-n-butylamidino, N-n-pentylamidino, N-n-hexylamidino, N,N-diethylamidino, and N-methyl-N-ethylamidino groups.

Examples of the phenyl lower alkyl group (which may have, on the phenyl ring, 1 to 3 substituents selected from the group consisting of a lower alkylenedioxy group and a lower alkoxy group), include, in addition to the above described phenyl lower alkyl groups, phenylalkyl groups whose alkyl moiety is a linear or branched alkyl group having 1 to 6 carbon atoms (and which may have, on the phenyl ring, 1 to 3 substituents selected from the group consisting of a linear or branched alkylenedioxy group having 1 to 4 carbon atoms and a linear or branched alkoxy group having 1 to 6 carbon atoms) such as 3,4-methylenedioxybenzyl, 3,4-trimethylenedioxybenzyl, 2-(2,3-ethylenedioxyphenyl)ethyl, 1-(3,4-trimethylenedioxyphenyl)ethyl, 3-(2,3-tetramethylenedioxyphenyl)propyl, 4-(3,4-methylenedioxyphenyl)butyl, 5-(2,3-ethylenedioxyphenyl)pentyl, 6-(3,4-trimethylenedioxyphenyl)hexyl, 1,1-dimethyl-2-(2,3-methylenedioxyphenyl)ethyl, 2-methyl-3-(3,4-ethylenedioxyphenyl)propyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl)propyl, 4-(4-ethoxyphenyl)butyl, 5-(4-isopropoxyphenyl)pentyl, 6-(3-butoxyphenyl)hexyl, 1,1-dimethyl-2-(4-pentyloxyphenyl)ethyl, 2-methyl-3-(4-hexyloxyphenyl)propyl, 3,4-dimethoxybenzyl, 3,4-diethoxybenzyl, 2,4-dimethoxybenzyl, 2,5-dimethoxybenzyl, 2,6-dimethoxybenzyl, and 3,4,5-trimethoxybenzyl groups.

Examples of the piperazinyl substituted oxalyl group which may have, on the piperazine ring, 1 to 3 substituents selected from the group consisting of a phenyl lower alkyl group (which may have, on the phenyl ring, 1 to 3 substituents selected from the group consisting of a lower alkylenedioxy group and a lower alkoxy group) and a pyridyl lower alkyl group include piperazinyl substituted oxalyl groups which may have, on the piperazine ring, 1 to 3 substituents selected from the group consisting of a phenylalkyl group whose alkyl moiety is a linear or branched alkyl group having 1 to 6 carbon atoms (and which may have, on the phenyl ring, 1 to 3 substituents selected from the group consisting of a linear or branched alkylenedioxy group having 1 to 4 carbon atoms and a linear or branched alkoxy group having 1 to 6 carbon atoms) and a pyridylalkyl group whose alkyl moiety is a linear or branched alkyl group having 1 to 6 carbon atoms such as 4-(3,4-methylenedioxybenzyl)-(1-, 2- or 3-)piperazinyloxalyl, 4-(2-, 3- or 4-pyridylmethyl)-(1-, 2- or 3-)piperazinyloxalyl, 4-(3,4-dimethyoxybenzyl)-1-, 2- or 3-)piperazinyloxalyl, 4-(2,3-methylenedioxybenzyl)-(1-, 2- or 3-)piperazinyloxalyl, 4-(3,4-ethylenedioxybenzyl)-(1-, 2- or 3-)piperazinyloxalyl, 4-[2-(2-, 3- or 4-pyridyl)ethyl]-(1-, 2- or 3-)piperazinyloxalyl, 4-[3-(2-, 3- or 4-pyridyl)propyl-(1-, 2- or 3-)piperazinyloxalyl, 2,4-bis(2-, 3- or 4-pyridylmethyl)-(1-, 2- or 3-)piperazinyloxalyl, 2-(3,4-methylenedioxybenzyl)-4-(2-, 3- or 4-pyridylmethyl)-(1-, 2- or 3-)piperazinyloxalyl, and 2,3,4-tri(2-, 3- or 4-pyridylmethyl)-(1-, 2- or 3-)piperazinyloxalyl groups.

Examples of the cyano substituted lower alkyl group include cyanoalkyl groups whose alkyl moiety is a linear or branched alkyl group having 1 to 6 carbon atoms such as cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, and 2-methyl-3-cyanopropyl groups.

Examples of the 5-to 7-membered saturated heterocyclic ring formed by binding $R^{36}$ and $R^{37}$ each other, together with nitrogen atoms bound to them, through or not through a nitrogen atom, an oxygen atom, or a sulfur atom include pyrrolidinyl, piperidinyl, piperazinyl, morpholino, thiomorpholino, and homopiperazinyl groups.

Examples of the 5-to 10-membered saturated or unsaturated heterocyclic ring formed by binding $R^{14}$ and $R^{15}$ each other, together with nitrogen atoms bound to them, through or not through a nitrogen atom, an oxygen atom, or a sulfur atom include 1,2,3,4,5,6-hexahydropyrimidinyl, pyrrolidinyl, piperidinyl, piperazinyl, morpholino, thiomorpholino, homopiperazinyl, homopiperidinyl, thiazolidinyl, 1,2,5,6-tetrahydropyridyl, pyrrolyl, pyrazolyl, imidazolyl, 2-pyrrolinyl, 2-imidazolinyl, imidazolidinyl, 2-pyrazolinyl, pyrazolidinyl, 1,2-dihydropyridyl, 1,2-dihydroquinolyl, 1,2,3,4-tetrahydroquinolyl, 1,2,3,4-tetrahydroisoquinolyl, 1,2-dihydroisoquinolyl, indolyl, isoindolyl, indolinyl, isoindolinyl, 3,4-dihydro-2H-1,4-benzooxazinyl, 3,4-dihydro-2H-1,4-benzothiazolidinyl, 1,4-benzothiazinyl, 1,2,3,4-tetrahydroquinoxalinyl, 1,2,3,4-tetrahydrocinnolinyl, 1,2,3,4-tetrahydrophthalazinyl, 1,2,3,4-tetrahydroquinazolinyl, 1,2-dihydroquinoxalinyl, 3,4-dihydroquinoxalinyl, 1,4-dihydroquinoxalinyl, 1,2-dihydrocinnolinyl, 1,2-dihydrophthalazinyl, 3,4-dihydrophthalazinyl, 1,2-dihydroquinazolinyl, 3,4-dihydroquinazolinyl, indazolyl, indazolinyl, 6-azabicyclo[3,2,1]octyl, 3-aza-spiro[5,5]undecyl, and thiazolidinyl groups. Preferably, $R^{14}$ and $R^{15}$, together with the nitrogen atom to which they bind, bind to each other, directly or via a nitrogen atom to form a 6-membered saturated heterocyclic group. Most preferably, they include piperidinyl and piperazinyl groups.

Examples of the phenyl lower alkoxy group include phenylalkoxy groups whose alkoxy moiety is a linear or branched alkoxy group having 1 to 6 carbon atoms such as benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, and 2-methyl-3-phenylpropoxy groups.

Examples of the phenyl substituted lower alkyl group which has 1 or 2 phenyl groups which may be substituted on the phenyl ring with 1 to 3 substituents selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy groups; and which may have a pyridyl group on the lower alkyl group include in addition to the above described phenyl lower alkyl groups, phenyl substituted alkyl groups which have 1 or 2 phenyls which may be substituted on the phenyl ring with 1 to 3 substituents selected from the group consisting of a linear or branched alkanoyl group having 1 to 6 carbon atoms, an amino group which may have 1 or 2 linear or branched alkanoyl groups having 1 to 6 carbon atoms as substituents, an alkoxycarbonyl group whose akloxy moiety is a linear or branched alkoxy group having 1 to 6 carbon atoms, a cyano group, a nitro group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, a phenylalkoxy groups whose alkoxy moiety is a linear or branched alkoxy group having 1 to 6 carbon atoms, a hydroxy group, and a linear or branched alkylenedioxy group having 1 to 4 carbon atoms; which may have a pyridyl group on the alkyl group, and whose alkyl moiety is a linear or branched alkyl group having 1 to 6 carbon atoms, such as 1-phenyl-1-(2, 3 or 4-)pyridyl methyl, 1,1-diphenylmethyl, 1,1-di(4-fluorophenyl)methyl, 1-phenyl-1-(4-methoxyphenyl)methyl, 3,4-methylenedioxybenzyl, 3,4-ethylenedioxybenzyl, 3,4-trimethylenedioxybenzyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, 3,4-dimethoxybenzyl, 3,5-dimethoxybenzyl, 2-chlorobenzyl, 3-chlorobenzyl, 4-chlorobenzyl, 2-methylbenzyl, 3-methylbenzyl, 4-methylbenzyl, 3,4-dimethylbenzyl, 2,3-dimethylbenzyl, 2-methoxybenzyl, 3-methoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-methoxycarbonylbenzyl, 3-methoxycarbonylbenzyl, 4-tert-butylbenzyl, 4-ethylbenzyl, 4-isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 4-phenylbenzyl, 3,3-diphenylpropyl, 3-methyl-4-nitrobenzyl, 4-(4-methoxyphenyl)butyl, 2-(4-methylphenyl)ethyl, 4-tert-butoxycarbonylbenzyl, 3-chloro-6-methoxybenzyl, 4-acetylaminobenzyl, 4-nitro-3-methylbenzyl, 4-hydroxybenzyl, 3-hydroxybenzyl, 2-hydroxybenzyl, 4-tert-butyrylbenzyl, 4-benzyloxybenzyl, 4-pivaloylbenzyl, 2-(4-acetylphenyl)ethyl, 1-(3-propionylphenyl)ethyl, 3-(2-butyrylphenyl)propyl, 4-(4-pentanoylphenyl)butyl, 5-(3-hexanoylphenyl)pentyl, 6-(2,4-diacetylphenyl)hexyl, 1,1-dimethyl-2-(2,4,6-triacetylphenyl)ethyl, 2-methyl-3-(3,4-diacetylphenyl)propyl, 2-(4-aminophenyl)ethyl, 1-(3-propionylaminophenyl)ethyl, 3-(2-butyrylaminophenyl)propyl, 4-(4-pentanoylamino)phenylbutyl, 5-(hexanoylaminophenyl)pentyl, 6-(N-acetyl-N-propionylaminophenyl)hexyl, 1,1-dimethyl-2-(3,4-diaminophenyl)ethyl, 2-methyl-3-(3,4,5-triacetylaminophenyl)propyl, 2-(2-ethoxycarbonylphenyl)ethyl, 1-(3-propoxycarbonylphenyl)ethyl, 3-(4-pentyloxycarbonylphenyl)propyl, 4-(3-hexyloxycarbonylphenyl)butyl, 5-(3,4-dimethoxycarbonylphenyl)pentyl, 6-(3,4,5-triethoxycarbonylphenyl)hexyl, 1,1-dimethyl-2-(4-butoxycarbonylphenyl)ethyl, 2-methyl-3-(4-methoxycarbonylphenyl)propyl, 2-(2-cyanophenyl)ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl)ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl)hexyl, 1,1-dimethyl-2-(2,4-dinitrophenyl)ethyl, 2-methyl-3-(2,4,6-trinitrophenyl)propyl, 2-(2-phenylphenyl)ethyl, 1-(3-phenylphenyl)ethyl, 3-(4-phenylphenyl)propyl, 4-(2-phenylphenyl)butyl, 5-(3-phenylphenyl)pentyl, 6-(4-phenylphenyl)hexyl, 1,1-dimethyl-2-(2,4-diphenylphenyl)ethyl, 2-methyl-3-(2,4,6-triphenylphenyl)propyl, 2-(2-fluorophenyl)ethyl, 1-(3-bromophenyl)ethyl, 3-(4-iodophenyl)propyl, 4-(2-bromophenyl)butyl, 5-(3-chlorophenyl)pentyl, 6-(4-bromophenyl)hexyl, 1,1-dimethyl-2-(2,4-dichlorophenyl)ethyl, 2-methyl-3-(2,4,6-trifluorophenyl)propyl, 2-(2-ethylphenyl)ethyl, 1-(3-propylphenyl)ethyl, 3-(4-butylphenyl)propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl)phenyl]propyl, 2-(2-ethoxyphenyl)ethyl, 1-(3-propoxyphenyl)ethyl, 3-(4-butoxyphenyl)propyl, 4-(2-pentyloxyphenyl)butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri(trifluoromethoxy)phenyl]propyl, 2-(2-benzyloxyphenyl)ethyl, 1-[3-(2-phenylethoxy)phenyl]ethyl, 3-[4-(3-phenylpropoxy)phenyl]propyl, 4-[2-(4-phenylbutoxy)phenyl]butyl, 5-[3-(5-phenylpentyloxy)phenyl]pentyl, 6-[4-(6-phenylhexyloxy)phenyl]hexyl, 1,1-dimethyl-2-(2,4-dibenzyloxyphenyl)ethyl, 2-methyl-3-(2,4,6-tribenzyloxyphenyl)propyl, 2-(2-hydroxyphenyl)ethyl, 1-(3-hydroxyphenyl)ethyl, 3-(4-hydroxyphenyl)propyl, 4-(2-hydroxyphenyl)butyl, 5-(3-hydroxyphenyl)pentyl, 6-(4-hydroxyphenyl)hexyl, 1,1-dimethyl-2-(2,4-dihydroxyphenyl)ethyl, 2-methyl-3-(2,4,6-trihydroxyphenyl)propyl, 2-(3,4-methylenedioxyphenyl)ethyl, 1-(2,3-ethylenedioxyphenyl)ethyl, 3-(3,4-trimethylenedioxyphenyl)propyl, 4-(3,4-tetramethylenedioxyphenyl)butyl, 5-(3,4-methylenedioxyphenyl)pentyl, 6-(3,4-ethylenedioxyphenyl)hexyl, 1,1-dimethyl-2-(3,4-methylenedioxy)ethyl, and 2-methyl-3-(3,4-methylenedioxyphenyl)propyl groups. Preferably, they include phenyl substituted lower alkyl groups which may be substituted on the phenyl ring with group(s), as substituent(s), selected from the group consisting of a lower alkanoyl group, an amino group which may have a lower alkanoyl group as a substituent, a lower alkoxycarbonyl group, a cyano group, a nitro group, a phenyl group, a halogen atom, a lower alkyl group which may have a halogen atom as a substituent, a lower alkoxy group which may have a halogen atom as a substituent, a phenyl lower alkoxy group, a hydroxyl group, and a lower alkylenedioxy groups.

Examples of the pyridyl lower alkyl group which may have, on the pyridine ring, 1 to 3 substituents selected from the group consisting of a hydroxyl group and a lower alkyl group which may have a hydroxyl group as a substituent include, in addition to the above described pyridyl lower alkyl groups, pyridylalkyl groups which may have, on the pyridine ring, 1 to 3 substituents selected from the group consisting of a hydroxy group and a linear or branched alkyl group having 1 to 6 carbon atoms which may have 1 to 3 hydroxy groups as substituents, and whose alkyl moiety is a linear or branched alkyl group having 1 to 6 carbon atoms such as [2-methyl-(3, 4, 5 or 6-)pyridyl]methyl, [2-methyl-3-hydroxy-5-hydroxymethyl-(4 or 6-)pyridyl]methyl, 2-[3-ethyl-(2, 4, 5 or 6-)pyridyl]ethyl, 1-[4-propyl-(2, 3, 5 or 6-)pyridyl]ethyl, 3-[2-butyl-(3, 4, 5 or 6-)pyridyl]propyl, 4-[3-pentyl-(2, 4, 5 or 6-)pyridyl]butyl, 1,1-dimethyl-2-[4-hexyl-(2, 3, 5 or 6-)pyridyl]ethyl, 5-[2,3-dimethyl-(4, 5 or 6-)pyridyl]pentyl, 6-[2,4,6-trimethyl-(3 or 5-)pyridyl]hexyl, 1-[2-hydroxy-(2, 3, 5 or 6-)pyridyl]isopropyl, 2-methyl-3-[3-hydroxy-(2, 4, 5 or 6-)pyridyl]propyl, [2-hydroxy-(3, 4, 5 or 6-)pyridyl]methyl, 2-[3-hydroxy-(2, 4, 5 or 6-)pyridyl]ethyl, 1-[4-hydroxy-(2, 3, 5 or 6-)pyridyl]ethyl, 3-[2-hydroxy-(3, 4, 5 or 6-)pyridyl]propyl, 4-[3-hydroxy-(2, 4, 5 or 6-)pyridyl]butyl, 1,1-dimethyl-2-[4-hydroxy-(2, 3, 5 or 6-)pyridyl]ethyl, 5-[2,3-dihydroxy-(4, 5 or 6-)pyridyl]pentyl, 6-[2,4,6-trihydroxy-(3 or 5-)pyridyl]hexyl, [2-hydroxymethyl-(3, 4, 5 or 6-)pyridyl]methyl, 2-[3-(2-hydroxyethyl)-(2, 4, 5 or 6-)pyridyl]ethyl, 1-[4-(3-hydroxypropyl)-(2, 3, 5 or 6-)pyridyl]ethyl, 3-[2-(4-hydroxybutyl)-(3, 4, 5 or 6-)pyridyl]propyl, 4-[3-(5-hydroxypentyl)-(2, 4, 5 or 6-)pyridyl]butyl, 1,1-dimethyl-2-[4-(6-hydroxyhexyl)-(2, 3, 5 or 6-)pyridyl]ethyl, 5-[2,3-di(hydroxymethyl)-(4, 5 or 6-)pyridyl]pentyl, 6-[2,4,6-tri(hydroxymethyl)-(3 or 5-)pyridyl]hexyl, 1-[2-hydroxymethyl-(2, 3, 5 or 6-)pyridyl]isopropyl, 2-methyl-3-[3-(2,3-dihydroxypropyl)-(2, 4, 5 or 6-)pyridyl]propyl, [2-methyl-3-(2,2,4-trihydroxybutyl)-(4, 5 or 6-)pyridyl]methyl, and [2-methyl-5-hydroxymethyl-(3, 4 or 6-)pyridyl]methyl groups.

Examples of the pyrrolyl lower alkyl group which may have 1 to 3 lower alkyl groups as substituents on the pyrrole ring include pyrrolylalkyl groups which may have 1 to 3 linear or branched alkyl groups having 1 to 6 carbon atoms on the pyrrole ring and whose alkyl moiety is a linear or branched alkyl group having 1 to 6 carbon atoms such as [(1, 2 or 3-)pyrrolyl]methyl, 2-[(1, 2 or 3-)pyrrolyl]ethyl, 1-[(1, 2 or 3-)pyrrolyl]ethyl, 3-[(1, 2 or 3-)pyrrolyl]propyl, 4-[(1, 2 or 3-)pyrrolyl]butyl, 5-[(1, 2 or 3-)pyrrolyl]pentyl, 6-[(1, 2 or 3-)pyrrolyl]hexyl, 1,1-dimethyl-2-[(1, 2 or 3-)pyrrolyl]ethyl, 2-methyl-3-[(1, 2 or 3-)pyrrolyl]propyl, [1-methyl-(2 or 3-)pyrrolyl]methyl, 2-[2-ethyl-(1, 3, 4 or 5-)pyrrolyl]ethyl, 1-[3-propyl-(1, 2, 4 or 5-)pyrrolyl]ethyl, 3-[1-butyl-(2, 3 or 4-)pyrrolyl]propyl, 4-[2-pentyl-(1, 3, 4 or 5-)pyrrolyl]butyl, 5-[3-hexyl-(1, 2, 4 or 5-)pyrrolyl]pentyl, 6-[1,2-dimethyl-(3, 4 or 5-)pyrrolyl]hexyl, 1,1-dimethyl-2-[1,2,3-trimethyl-(4 or 5-)pyrrolyl]ethyl, and 2-methyl-3-[1-ethyl-2-methyl-(3, 4 or 5-)pyrrolyl]propyl groups.

Examples of the benzoxazolyl lower alkyl group include benzoxazolylalkyl groups whose alkyl moiety is a linear or branched alkyl group having 1 to 6 carbon atoms such as [(2, 4, 5, 6 or 7-)benzooxazolyl]methyl, 2-[(2, 4, 5, 6 or 7-)benzooxazolyl]ethyl, 1-[(2, 4, 5, 6 or 7-)benzooxazolyl]ethyl, 3-[(2, 4, 5, 6 or 7-)benzooxazolyl]propyl, 4-[(2, 4, 5, 6 or 7-)benzooxazolyl]butyl, 5-[(2, 4, 5, 6 or 7-)benzooxazolyl]pentyl, 6-[(2, 4, 5, 6 or 7-)benzooxazolyl]hexyl, 1,1-dimethyl-2-[(2, 4, 5, 6 or 7-)benzooxazolyl]ethyl, and 2-methyl-3-[(2, 4, 5, 6 or 7-)benzooxazolyl]propyl groups. Examples of the benzothiazolyl lower alkyl group include benzothiazolylalkyl groups whose alkyl moiety is a linear or branched alkyl group having 1 to 6 carbon atoms such as [(2, 4, 5, 6 or 7-)benzothiazolyl]methyl, 2-[(2, 4, 5, 6 or 7-)benzothiazolyl]ethyl, 1-[(2, 4, 5, 6 or 7-)benzothiazolyl]ethyl, 3-[(2, 4, 5, 6 or 7-)benzothiazolyl]propyl, 4-[(2, 4, 5, 6 or 7-)benzothiazolyl]butyl, 5-[(2, 4, 5, 6 or 7-)benzothiazolyl]pentyl, 6-[(2, 4, 5, 6 or 7-)benzothiazolyl]hexyl, 1,1-dimethyl-2-[(2, 4, 5, 6 or 7-)benzothiazolyl]ethyl, and 2-methyl-3-[(2, 4, 5, 6 or 7-)benzothiazolyl]propyl groups.

Examples of the furyl lower alkyl group include furylalkyl groups whose alkyl moiety is a linear or branched alkyl group having 1 to 6 carbon atoms such as [(2 or 3-)furyl]methyl, 2-[(2 or 3-)furyl]ethyl, 1-[(2 or 3-)furyl]ethyl, 3-[(2 or 3-)furyl]propyl, 4-[(2 or 3-)furyl]butyl, 5-[(2 or 3-)furyl]pentyl, 6-[(2 or 3-)furyl]hexyl, 1,1-dimethyl-2-[(2 or 3-)furyl]ethyl, and 2-methyl-3-[(2 or 3-)furyl]propyl groups.

Examples of the thiazolidinyl lower alkyl group which may have an oxo group as a substituent on the thiazolidine ring include thiazolidinylalkyl groups which may have 1 to 3 oxo groups as substituents on the thiazolidine ring and whose alkyl moiety is a linear or branched alkyl group having 1 to 6 carbon atoms such as (2, 3, 4 or 5-)thiazolidinylmethyl, 2-[(2, 3, 4 or 5-)thiazolidinyl]ethyl, 1-[(2, 3, 4 or 5-)thiazolidinyl] ethyl, 3-[(2, 3, 4 or 5-)thiazolidinyl]propyl, 4-[(2, 3, 4 or 5-)thiazolidinyl]butyl, 5-[(2, 3, 4 or 5-)thiazolidinyl]pentyl, 6-[(2, 3, 4 or 5-)thiazolidinyl]hexyl, 1,1-dimethyl-2-[(2, 3, 4 or 5-)thiazolidinyl]ethyl, 2-methyl-3-[(2, 3, 4 or 5-)thiazolidinyl]propyl, [2,4-dioxo-(3 or 5-)thiazolidinyl]methyl, 2-[2-oxo-(3, 4 or 5-)thiazolidinyl]ethyl, 1-[4-oxo-(2, 3 or 5-)thiazolidinyl]ethyl, 3-[2-oxo-(3, 4 or 5-)thiazolidinyl]propyl, 4-[5-oxo-(2, 3 or 4-)thiazolidinyl]butyl, 5-[2,5-dioxo-(3 or 4-)thiazolidinyl]pentyl, 6-[2,4,5-trioxo-3-thiazolidinyl] hexyl, 1-[4,5-dioxo-(2 or 3-)thiazolidinyl]ethyl, 2-[4,5-dioxo-(2- or 3-)thiazolidinyl]ethyl, 1,1-dimethyl-2-[2,4-dioxo-(3 or 5-)thiazolidinyl]ethyl, and 2-methyl-3-[2,4-dioxo-(3 or 5-)thiazolidinyl]propyl groups.

Examples of the thiazolidinylidene lower alkyl group which may have an oxo group as a substituent on the thiazolidine ring include thiazolidinylidenealkyl groups which may have 1 to 3 oxo groups as substituents on the thiazolidine ring and whose alkyl moiety is a linear or branched alkyl group having 1 to 6 carbon atoms such as (2, 4 or 5-)thiazolidinylidenemethyl, (2, 4 or 5-)thiazolidinylideneethyl, (2, 4 or 5-)thiazolidinylidenepropyl, (2, 4 or 5-)thiazolidinylideneisopropyl, (2, 4 or 5-)thiazolidinylidenebutyl, (2, 4 or 5-)thiazolidinylidenepentyl, (2, 4 or 5-)thiazolidinylidenehexyl, 4,5-dioxo-2-thiazolidinylidenemethyl, 2,5-dioxo-4-thiazolidinylidenemethyl, 2,4-dioxo-5-thiazolidinylidenemethyl, 4-oxo-(2 or 5-)thiazolidinylideneethyl, 5-oxo-(2 or 4-)thiazolidinylidenepropyl, and 2-oxo-(4 or 5-)thiazolidinylidenebutyl groups.

Examples of the benzoyl group which may be substituted on the phenyl ring with 1 to 3 groups selected from the group consisting of a cyano group, an amino group which may have a lower alkylsulfonyl group as a substituent, a halogen atom, a lower alkoxy group, a lower alkyl group which may have a halogen atom as a substituent, a thiazolidinyl lower alkyl group which may have an oxo group as a substituent on the thiazolidine ring, a thiazolidinylidene lower alkyl group which may have an oxo group as a substituent on the thiazolidine ring, and a lower alkylenedioxy group include benzoyl groups which may be substituted on the phenyl ring with 1 to 3 groups selected from the group consisting of a cyano group; an amino group which may have 1 or 2 linear or branched alkylsulfonyl groups having 1 to 6 carbon atoms as substituents; a halogen atom; a linear or branched alkoxy group having 1 to 6 carbon atoms; a linear or branched alkyl group having 1 to 6 carbon atoms which may have 1 to 3 halogen atoms as substituents; a thiazolidinylalkyl group which may have 1 to 3 oxo groups as substituents on the thiazolidine ring and whose alkyl moiety is a linear or branched alkyl group having 1 to 6 carbon atoms; a thiazolidinylidenealkyl group which may have 1 to 3 oxo groups as substituents on the thiazolidine ring and whose alkyl moiety is a linear or branched alkyl group having 1 to 6 carbon atoms; and a linear or branched alkylenedioxy group having 1 to 4 carbon atoms such as benzoyl, 4-cyanobenzoyl, 3,4-methylenedioxybenzoyl, 2-aminobenzoyl, 3-aminobenzoyl, 4-aminobenzoyl, 3,4-diaminobenzoyl, 2,4,6-triaminobenzoyl, 4-methoxybenzoyl, 4-trifluoromethylbenzoyl, 4-chlorobenzoyl, 3,4-difluorobenzoyl, 2-fluorobenzoyl, 3-bromobenzoyl, 4-iodobenzoyl, 3,4-dimethoxybenzoyl, 4-fluorobenzoyl, 3-cyanobenzoyl, 2-cyanobenzoyl, 2,3-dicyanobenzoyl, 3,4,5-tricyanobenzoyl, 4-methylbenzoyl, 4-(2,4-dioxothiazolidinylmethyl)benzoyl, 4-(2,4-dioxothiazolidinylidenemethyl)benzoyl, 2-methylbenzoyl, 3-methylbenzoyl, 2-ethylbenzoyl, 3-ethylbenzoyl, 4-ethylbenzoyl, 4-isopropylbenzoyl, 3-butylbenzoyl, 4-pentylbenzoyl, 4-hexylbenzoyl, 3,4-dimethylbenzoyl, 3,4-diethylbenzoyl, 2,4-dimethylbenzoyl, 2,5-dimethylbenzoyl, 2,6-dimethylbenzoyl, 3,4,5-trimethylbenzoyl, 2-methoxybenzoyl, 3-methoxybenzoyl, 2-ethoxybenzoyl, 3-ethoxybenzoyl, 4-ethoxybenzoyl, 4-isopropoxybenzoyl, 3-butoxybenzoyl, 4-pentyloxybenzoyl, 4-hexyloxybenzoyl, 3,4-diethoxybenzoyl, 2,4-dimethoxybenzoyl, 2,5-dimethoxybenzoyl, 2,6-dimethoxybenzoyl, 3,4,5-trimethoxybenzoyl, 2-trifluoromethylbenzoyl, 3-trifluoromethylbenzoyl, 4-trifluoromethylbenzoyl, 2-(bromomethyl)benzoyl, 3-(2-chloroethyl)benzoyl, 4-(2,3-dichloropropyl)benzoyl, 4-(4-fluorobutyl)benzoyl, 3-(5-chloropentyl)benzoyl, 4-(5-bromohexyl)benzoyl, 4-(5,6-dibromohexyl)benzoyl, 3,4-di(trifluoromethyl)benzoyl, 3,4-di(4,4,4-trichlorobutyl)benzoyl, 2,4-di(3-chloro-2-methylpropyl)benzoyl, 2,5-di(3-chloropropyl)benzoyl, 2,6-di(2,2,2-trifluoroethyl)benzoyl, 3,4,5-tri(trifluoromethyl) benzoyl, 4-(2,2,2-trichloroethyl)benzoyl, 2-methyl-4-trifluoromethylbenzoyl, 3-ethyl-4-trichloromethylbenzoyl, 2-methoxy-4-trifluoromethylbenzoyl, 3-ethyl-4-fluorobenzoyl, 3-ethoxy-4-trichloromethylbenzoyl, 2-methyl-3-trifluoromethyl-4-trifluoromethylbenzoyl, 3-fluorobenzoyl, 4-fluorobenzoyl, 2-bromobenzoyl, 4-bromobenzoyl, 2-iodobenzoyl, 3-iodobenzoyl, 2,3-dibromobenzoyl, 2,4-diiodobenzoyl, 2,5-difluorobenzoyl, 2,6-dichlorobenzoyl, 2,4,6-trichlorobenzoyl, 2,4-difluorobenzoyl, 3,4-difluorobenzoyl, 3,5-difluorobenzoyl, 2,6-difluorobenzoyl, 2-chlorobenzoyl, 3-chlorobenzoyl, 4-chlorobenzoyl, 2,3-dichlorobenzoyl, 2,4-dichlorobenzoyl, 2,5-dichlorobenzoyl, 3,4-dichlorobenzoyl, 2,6-dichlorobenzoyl, 3,5-dichlorobenzoyl, 2,4,6-trifluorobenzoyl, 2,4-difluorobenzoyl, 3,4-difluorobenzoyl, 3,4-methylenedioxybenzoyl, 3,4-trimethylenedioxybenzoyl, 2,3-ethylenedioxybenzoyl, 3,4-trimethylenedioxybenzoyl, 2,3-tetramethylenedioxybenzoyl, 2,3-methylenedioxybenzoyl, 3,4-ethylenedioxybenzoyl, and 2-methanesulfonylaminobenzoyl groups.

Examples of the thiazolidinyl lower alkanoyl group which may be substituted on the thiazolidine ring with a group selected from the group consisting of an oxo group and a group of the formula:

[Formula 56]

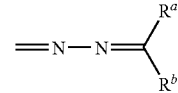

wherein $R^a$ and $R^b$ each represent a lower alkyl group, include thiazolidinylalkanoyl groups which may be substituted on the thiazolidine ring with 1 to 3 substituents selected from the group consisting of an oxo group and a group of the formula:

[Formula 57]

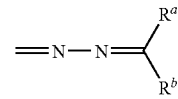

wherein $R^a$ and $R^b$ each represent a linear or branched alkyl group having 1 to 6 carbon atoms, and whose alkanoyl moiety is a linear or branched alkanoyl group having 2 to 6 carbon atoms such as 2-[(2, 3, 4 or 5-)thiazolidinyl]acetyl, 3-[(2, 3, 4 or 5-)thiazolidinyl]propionyl, 2-[(2, 3, 4 or 5-)thiazolidinyl] propionyl, 4-[(2, 3, 4 or 5-)thiazolidinyl]butyryl, 5-[(2, 3, 4 or 5-)thiazolidinyl]pentanoyl, 6-[(2, 3, 4 or 5-)thiazolidinyl] hexanoyl, 2,2-dimethyl-3-[(2, 3, 4 or 5-)thiazolidinyl]propionyl, 2-methyl-3-[(2, 3, 4 or 5-)thiazolidinyl]propionyl, [2,4-dioxo-(3 or 5-)thiazolidinyl]acetyl, 3-[2-oxo-(3, 4 or 5-)thiazolidinyl]propionyl, 2-[4-oxo-(2, 3 or 5-)thiazolidinyl]propionyl, 4-[5-oxo-(2, 3 or 4-)thiazolidinyl]butyryl, 5-[2,5-dioxo-(3 or 4-)thiazolidinyl]pentanoyl, 6-[2,4,5-trioxo-3-thiazolidinyl]hexanoyl, 2-[4,5-dioxo-(2 or 3-)thiazolidinyl]acetyl, 2,2-dimethyl-3-[2,4-dioxo-(3 or 5-)thiazolidinyl]propionyl, 2-methyl-3-[2,4-dioxo-(3 or 5-)thiazolidinyl] propionyl, 2-[4-oxo-2-isopropylidenehydrazono-(3 or 5-)thiazolidinyl]acetyl, 2-[2-oxo-5-isopropylidenehydrazono-(3 or 4-)thiazolidinyl]acetyl, 2-[2,4-di(isopropylidenehydrazono)-(3 or 5-)thiazolidinyl]acetyl, 3-[2-methylidenehydrazono-(3, 4 or 5-)thiazolidinyl]propionyl, 2-[4-ethylidenehydrazono-(2, 3 or 5-)thiazolidinyl]propionyl, 4-[5-propylidenehydrazono-(2, 3 or 4-)thiazolidinyl]butyryl, 5-[2,5-di(isopropylidenehydrazono)-(3 or 4-)thiazolidinyl] pentanoyl, 6-[2,4,5-tri(isopropylidenehydrazono)-3-thiazolidinyl]hexanoyl, 2-[4,5-di(isopropylidenehydrazono)-(2 or 3-)thiazolidinyl]acetyl, 2,2-dimethyl-3-[4-butylidenehydrazono(2, 3 or 5-)thiazolidinyl]propionyl, 2-methyl-3-[5-pentylidene-(2, 3 or 4-)thiazolidinyl]propionyl, and 2-(hexylidenehydrazono)-(3, 4 or 5-)thiazolidinylacetyl groups.

Examples of the lower alkyl group which may have a substituent selected from the group consisting of a hydroxyl group and a halogen atom include, in addition to the above described lower alkyl groups, linear or branched alkyl groups having 1 to 6 carbon atoms which may have 1 to 3 substituents selected from the group consisting of a hydroxy group and a halogen atom such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, 2-hydroxy-3-fluoropropyl, and 2,2-dichloro-3-hydroxybutyl groups.

Examples of the carbamoyl group which may have a group selected from the group consisting of a lower alkoxy lower alkyl group and a lower alkyl group include carbamoyl groups which may have 1 or 2 groups selected from the group consisting of a linear or branched alkyl group having 1 to 6 carbon atoms and which has a linear or branched alkoxy group having 1 to 6 carbon atoms and a linear or branched alkyl group having 1 to 6 carbon atoms such as carbamoyl, N-(2-methoxyethyl)carbamoyl, methylcarbamoyl, ethylcarbamoyl, propylcarbamoyl, isopropylcarbamoyl, butylcarbamoyl, tert-butylcarbamoyl, pentylcarbamoyl, hexylcarbamoyl, dimethylcarbamoyl, diethylcarbamoyl, dipropylcarbamoyl, dibutylcarbamoyl, dipentylcarbamoyl, dihexylcarbamoyl, N-methyl-N-ethylcarbamoyl, N-ethyl-N-propylcarbamoyl, N-methyl-N-butylcarbamoyl, N-methyl-N-hexylcarbamoyl, N-(methoxymethyl)carbamoyl, N-(3-propoxypropyl)carbamoyl, N-(4-butoxybutyl)carbamoyl, N-(4-ethoxybutyl) carbamoyl, N-(5-pentyloxypentyl)carbamoyl, N-(5-methoxypentyl)carbamoyl, N-(6-hexyloxyhexyl)carbamoyl, di(2-methoxyethyl)carbamoyl, N-(2-methoxyethyl)-N-methylcarbamoyl, and N-(2-methoxyethyl)-N-ethylcarbamoyl groups.

Examples of the phenyl group which may be substituted on the phenyl ring with 1 to 3 groups selected from the group consisting of a carbamoyl group which may have a group selected from the group consisting of a lower alkoxy lower alkyl group and a lower alkyl group, a lower alkoxycarbonyl group, a carboxy group, a cyano group, a phenyl group, a halogen atom, a lower alkyl group which may have a halogen atom as a substituent, a lower alkoxy group which may have a halogen atom as a substituent, a benzoyl group which may have a halogen atom as a substituent on the phenyl ring, a phenyl lower alkyl group which may have a halogen atom as a substituent on the phenyl ring, and a hydroxyl group include phenyl groups which may be substituted on the phenyl ring with 1 to 3 groups selected from the group consisting of a carbamoyl group which may have 1 or 2 groups selected from the group consisting of an alkoxyalkyl group whose alkoxy moiety is a linear or branched alkoxy group having 1 to 6 carbon atoms and whose alkyl moiety is a linear or branched alkyl group having 1 to 6 carbon atoms and a linear or branched alkyl group having 1 to 6 carbon atoms; an alkoxycarbonyl group whose akloxy moiety is a linear or branched alkoxy group having 1 to 6 carbon atoms; a carboxy group; a cyano group; a phenyl group;

a halogen atom; a linear or branched alkyl group having 1 to 6 carbon atoms which may have 1 to 3 halogen atoms as substituents; a linear or branched alkoxy group having 1 to 6 carbon atoms which may have 1 to 3 halogen atoms as substituents; a benzoyl group which may have 1 to 3 halogen atoms as substituents on the phenyl ring; a phenylalkyl group which may have 1 to 3 halogen atoms as substituents on the phenyl ring and whose alkyl moiety is a linear or branched alkyl group having 1 to 6 carbon atoms, and a hydroxyl group such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,3-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy) phenyl, 3,4-di(4,4,4-trichlorobutoxy)phenyl, 2,4-di(3-chloro-2-methoxypropyl)phenyl, 2,5-di(3-chloropropoxy) phenyl, 2,6-di(2,2,2-trifluoroethoxy)phenyl, 3,4,5-tri (trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl) phenyl, 2,5-di(3-chloropropyl)phenyl, 2,6-di(2,2,2-trifluoroethyl)phenyl, 3,4,5-tri(trifluoromethyl)phenyl, 4-(2, 2,2-trichloroethyl)phenyl, 2-methyl-4-trifluoromethylphenyl, 3-ethyl-4-trichloromethylphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 4-isopropoxycarbonylphenyl, 3-butoxycarbonylphenyl, 4-tert-butoxycarbonylphenyl, 4-pentyloxycarbonylphenyl, 4-hexyloxycarbonylphenyl, 3,4-dimethoxycarbonylphenyl, 3,4-diethoxycarbonylphenyl, 2,4-dimethoxycarbonylphenyl, 2,5-diethoxycarbonylphenyl, 2,6-dimethoxycarbonylphenyl, 3,4,5-triethoxycarbonylphenyl, 2-cyanophenyl, 3-cyanophenyl, 4-cyanophenyl, 3,4-dicyanophenyl, 3,5-dicyanophenyl, 2,4-dicyanophenyl, 2,5-dicyanophenyl, 2,6-dicyanophenyl, 3,4,5-tricyanophenyl, 2-phenylphenyl, 3-phenylphenyl, 4-phenylphenyl, 3,4-diphenylphenyl, 3,5-diphenylphenyl, 2,4-diphenylphenyl, 2,5-diphenylphenyl, 2,6-diphenylphenyl, 3,4,5-triphenylphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 2-hydroxyphenyl, 3-hydroxyphenyl, 4-hydroxyphenyl, 3,4-dihydroxyphenyl, 3,5-dihydroxyphenyl, 2,4-dihydroxyphenyl, 2,5-dihydroxyphenyl, 2,6-dihydroxyphenyl, 3,4,5-trihydroxyphenyl, 3-benzylphenyl, 2-(2-phenylethyl)phenyl, 4-(1-phenylethyl)phenyl, 2-(3-phenylpropyl)phenyl, 3-(4-phenylbutyl)phenyl, 4-(5-phenylpentyl)phenyl, 2-(6-phenylhexyl)phenyl, 4-(1,1-dimethyl-2-phenylethyl)phenyl, 3-(2-methyl-3-phenylpropyl)phenyl, 2-(4-fluorobenzyl)phenyl, 2-methyl-5-chlorophenyl, 2-methoxy-5-chlorophenyl, 4-(4-fluorobenzoyl)phenyl, 4-(4-fluorobenzyl)phenyl, 3-(2-chlorobenzyl)phenyl, 4-(3-chlorobenzyl)phenyl, 2-(4-chlorobenzyl)phenyl, 3-[2-(4-fluorophenyl)ethyl]phenyl, 4-[2-(4-chlorophenyl)ethyl]phenyl, 2-(3,4-dibromobenzyl)phenyl, 3-(3,4-diiodobenzyl)phenyl, 4-(2,4-difluorobenzyl)phenyl, 2-(2,5-dichlorobenzyl)phenyl, 3-(2,6-dichlorobenzyl)phenyl, 4-(3,4,5-trifluorobenzyl)phenyl, 2-[3-(4-chlorophenyl)propyl]phenyl, 3-[1-(2-bromophenyl)ethyl]phenyl, 4-[4-(3-fluorophenyl)butyl]phenyl, 2-[5-(4-iodophenyl)pentyl]phenyl, 3-[6-(4-chlorophenyl)hexyl]phenyl, 2-[1,1-dimethyl-2-(3-fluorophenyl)ethyl]phenyl, 4-[2-methyl-3-(4-chlorophenyl)propyl]phenyl, 2,4-dibenzylphenyl, 2,4,6-tribenzylphenyl, 2-chloro-4-cyanophenyl, 3-hydroxy-4-phenylphenyl, 3-ethoxycarbonyl-2-benzoylphenyl, 2-benzyl-4-methyl-6-methoxyphenyl, 4-[(2-methoxyethyl)carbamoyl]phenyl, 3-(N-ethyl-N-isopropylcarbamoyl)phenyl, 4-dimethylcarbamoylphenyl, 2-carboxyphenyl, 3-carboxyphenyl, and 4-carboxyphenyl groups.

Examples of the phenyl group which has a lower alkylenedioxy group as a substituent on the phenyl ring include phenyl groups which has a linear or branched alkylenedioxy group having 1 to 4 carbon atom as a substituent on the phenyl ring such as 3,4-methylenedioxyphenyl, 3,4-trimethylenedioxyphenyl, 2,3-ethylenedioxyphenyl, 2,3-tetramethylenedioxyphenyl, 2,3-methylenedioxyphenyl, 3,4-ethylenedioxyphenyl, and 2,3-trimethylenedioxyphenyl groups.

Examples of the naphthyl lower alkyl group include naphthylalkyl groups whose alkyl moiety is a linear or branched alkyl group having 1 to 6 carbon atoms such as (1 or 2-)naphthylmethyl, 2-[(1 or 2-)naphthyl]ethyl, 1-[(1 or 2-)naphthyl]ethyl, 3-[(1 or 2-)naphthyl]propyl, 4-[(1 or 2-)naphthyl]butyl, 5-[(1 or 2-)naphthyl]pentyl, 6-[(1 or 2-)naphthyl]hexyl, 1,1-dimethyl-2-[(1 or 2-)naphthyl]ethyl, and 2-methyl-3-[(1 or 2-)naphthyl]propyl groups.

Examples of the phenoxy group which may be substituted on the phenyl ring with 1 to 3 groups selected from the group consisting of a cyano group, a lower alkyl group which may have a halogen atom as a substituent, and a lower alkoxy group which may have a halogen atom as a substituent include phenoxy groups which may be substituted on the phenyl group with 1 to 3 groups selected from the group consisting of a cyano group, a linear or branched alkyl group having 1 to 6 carbon atoms which may have 1 to 3 halogen atoms as substituents, and a linear or branched alkoxy group having 1 to 6 carbon atoms which may have 1 to 3 halogen atoms as substituents such as phenoxy, 2-methylphenoxy, 3-methylphenyl, 4-methylphenoxy, 2-ethylphenoxy, 3-ethylphenoxy, 4-ethylphenoxy, 4-isopropylphenoxy, 3-butylphenoxy, 4-pentylphenoxy, 4-hexylphenoxy, 3,4-dimethylphenoxy, 3,4-diethylphenoxy, 2,4-dimethylphenoxy, 2,5-dimethylphenoxy, 2,6-dimethylphenoxy, 3,4,5-trimethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 4-isopropoxyphenoxy, 3-butoxyphenoxy, 4-pentyloxyphenoxy, 4-hexyloxyphenoxy, 3,4-dimethoxyphenoxy, 3,4-diethoxyphenoxy, 2,4-dimethoxyphenoxy, 2,5-dimethoxyphenoxy, 2,6-dimethoxyphenoxy, 3,4,5-trimethoxyphenoxy, 2-trifluoromethoxyphenoxy, 3-trifluoromethoxyphenoxy, 4-trifluoromethoxyphenoxy, 2-(bromomethoxy)phenoxy, 3-(2-chloroethoxy)phenoxy, 4-(2,3-dichloropropoxy)phenoxy, 4-(4-fluorobutoxy)phenoxy, 3-(5-chloropentyloxy)phenoxy, 4-(5-bromohexyloxy)phenoxy, 4-(5,6-dibromohexyloxy)phenoxy, 3,4-di(trifluoromethoxy)phenoxy, 3,4-di(4,4,4-trichlorobutoxy)phenoxy, 2,4-di(3-chloro-2-methoxypropyl)phenoxy, 2,5-di(3-chloropropoxy)phenoxy, 2,6-di(2,2,2-trifluoroethoxy)phenoxy, 3,4,5-tri(trifluoromethoxy)phenoxy, 4-(2,2,2-trichloroethoxy)phenoxy, 2-methyl-4-trifluoromethoxyphenoxy, 3-ethyl-4-trichloromethoxyphenoxy, 2-methoxy-4-trifluoromethoxyphenoxy, 3-ethoxy-4-trichloromethoxyphenoxy, 2-trifluoromethylphenoxy, 3-trifluoromethylphenoxy, 4-trifluoromethylphenoxy, 2-(bromomethyl)phenoxy, 3-(2-chloroethyl)phenoxy, 4-(2,3-dichloropropyl)phenoxy, 4-(4-fluorobutyl)phenoxy, 3-(5-chloropentyl)phenoxy, 4-(5-bromohexyl)phenoxy, 4-(5,6-dibromohexyl)phenoxy, 3,4-di(trifluoromethyl)phenoxy, 3,4-di(4,4,4-trichlorobutyl)phenoxy, 2,4-di(3-chloro-2-methylpropyl)phenoxy, 2,5-di(3-chloropropyl)phenoxy, 2,6-di(2,2,2-trifluoroethyl)phenoxy, 3,4,5-tri(trifluoromethyl)phenoxy, 4-(2,2,2-trichloroethyl)phenoxy, 2-methyl-4-trifluoromethylphenoxy, 3-ethyl-4-trichloromethylphenoxy, 2-cyanophenoxy, 3-cyanophenoxy, 4-cyanophenoxy, 3,4-dicyanophenoxy, 3,5-dicyanophenoxy, 2,3-dicyanophenoxy, 2,4-dicyanophenoxy, 2,5-dicyanophenoxy, 2,6-dicyanophenoxy, 3,4,5-tricyanophenoxy, 2-cyano-4-methylphenoxy, 3-cyano-4-methoxyphenoxy, 3-cyano-5-trifluoromethylphenoxy, and 4-cyano-3-trifluoromethoxyphenoxy groups.

Examples of the phenyl lower alkoxy group which may be substituted on the phenyl ring with 1 to 3 groups selected from the group consisting of a halogen atom, a lower alkyl group which may have a halogen atom as a substituent, and a lower alkoxy group which may have a halogen atom as a substituent include, in addition to the above described phenyl lower alkoxy groups, phenylalkoxy groups which may be substituted on the phenyl ring with 1 to 3 groups selected from the group consisting of a halogen atom, a linear or branched alkyl group having 1 to 6 carbon atoms which may have 1 to 3 halogen atoms as substituents, and a linear or branched alkoxy group having 1 to 6 carbon atoms which may have 1 to 3 halogen atoms as substituents, and whose alkoxy moiety is a linear or branched alkoxy group having 1 to 6 carbon atoms such as 2,5-difluorobenzyloxy, 2,4-difluorobenzyloxy, 3,4-difluorobenzyloxy, 3,5-difluorobenzyloxy, 2,6-difluorobenzyloxy, 3-trifluoromethylbenzyloxy, 2-trifluoromethylbenzyloxy, 4-trifluoromethylbenzyloxy, 3,4-dimethoxybenzyloxy, 3,5-dimethoxybenzyloxy, 2-chlorobenzyloxy, 3-chlorobenzyloxy, 4-chlorobenzyloxy, 2-methylbenzyloxy, 3-methylbenzyloxy, 4-methylbenzyloxy, 3,4-dimethylbenzyloxy, 2,3-dimethylbenzyloxy, 2-methoxybenzyloxy, 3-methoxybenzyloxy, 4-methoxybenzyloxy, 2,3-dichlorobenzyloxy, 2,4-dichlorobenzyloxy, 2,5-dichlorobenzyloxy, 3,4-dichlorobenzyloxy, 2,6-dichlorobenzyloxy, 4-fluorobenzyloxy, 3-fluorobenzyloxy, 2-fluorobenzyloxy, 3-trifluoromethoxybenzyloxy, 4-trifluoromethoxybenzyloxy, 2-trifluoromethoxybenzyloxy, 4-tert-butylbenzyloxy, 4-ethylbenzyloxy, 4-isopropylbenzyloxy, 4-methoxy-3-chlorobenzyloxy, 2-(4-methoxyphenyl)ethoxy, 2-(4-fluorophenyl)ethoxy, 2-(4-chlorophenyl)ethoxy, 2-(3-methoxyphenyl)ethoxy, 2-(4-methylphenyl)ethoxy, 3-methyl-4-chlorobenzyloxy, 4-(4-methoxyphenyl)butoxy, 2-(4-methylphenyl)ethoxy, 4-tert-butoxybenzyloxy, 3-chloro-6-methoxybenzyloxy, 4-methoxy-3-methylbenzyloxy, 2-(2-fluorophenyl)ethoxy, 1-(3-bromophenyl)ethoxy, 3-(4-iodophenyl)propoxy, 4-(2-bromophenyl)butoxy, 5-(3-chlorophenyl)pentyloxy, 6-(4-bromophenyl)hexyloxy, 1,1-dimethyl-2-(2,4-dichlorophenyl)ethoxy, 2-methyl-3-(2,4,6-trifluorophenyl)propoxy, 2-(2-ethylphenyl)ethoxy, 1-(3-propylphenyl)propoxy, 3-(4-butylphenyl)propoxy, 4-(2-pentylphenyl)butoxy, 5-(3-hexylphenyl)pentyloxy, 6-(4-trifluoromethylphenyl)hexyloxy, 1,1-dimethyl-2-(2,4-dimethylphenyl)ethoxy, 2-methyl-3-[2,4,6-tri (trifluoromethyl)phenyl]propoxy, 2-(2-ethoxyphenyl)ethoxy, 1-(3-propoxyphenyl)ethoxy, 3-(4-butoxyphenyl)propoxy, 4-(2-pentyloxyphenyl)butoxy, 5-(3-hexyloxyphenyl)pentyloxy, 6-(4-trifluoromethoxyphenyl)hexyloxy, 1,1-dimethyl-2-(2,4-dimethoxyphenyl)ethoxy, and 2-methyl-3-[2,4,6-tri(trifluoromethoxy)phenyl]propoxy groups.

Examples of the 1,2,3,4-tetrahydronaphthyl substituted lower alkyl group which may have 1 to 5 lower alkyl groups as substituents on the 1,2,3,4-tetrahydronaphthalene ring include 1,2,3,4-tetrahydronaphthyl substituted alkyl groups which may have 1 to 5 linear or branched alkyl groups having 1 to 6 carbon atoms as substituents on the 1,2,3,4-tetrahydronaphthalene ring, and whose alkyl moiety is a linear or branched alkyl group having 1 to 6 carbon atoms such as (1, 2, 5 or 6-)1,2,3,4-tetrahydronaphthylmethyl, 2-[(1, 2, 5 or 6-)1,2,3,4-tetrahydronaphthyl]ethyl, 1-[(1, 2, 5 or 6-)1,2,3,4-tetrahydronaphthyl]ethyl, 3-[(1, 2, 5 or 6-)1,2,3,4-tetrahydronaphthyl]propyl, 4-[(1, 2, 5 or 6-)1,2,3,4-tetrahydronaphthyl]butyl, 5-[(1, 2, 5 or 6-)1,2,3,4-tetrahydronaphthyl]pentyl, 6-[(1, 2, 5 or 6-)1,2,3,4-tetrahydronaphthyl]hexyl, 1,1-dimethyl-2-[(1, 2, 5 or 6-)1,2,3,4-tetrahydronaphthyl]ethyl, 2-methyl-3-[(1, 2, 5 or 6-)1,2,3,4-tetrahydronaphthyl]propyl, 1,1,4,4-tetramethyl(2, 3, 5 or 6-)1,2,3,4-tetrahydronaphthylmethyl, 1,1,4,4,5-pentamethyl(2, 3, 6, 7 or 8-)1,2,3,4-tetrahydronaphthylmethyl, 1,4,4-trimethyl(2, 3, 5, 6, 7 or 8-)1,2,3,4-tetrahydronaphthylmethyl, 5,6-dimethyl(2, 3, 7 or 8-)1,2,3,4-tetrahydronaphthylmethyl, 2-[1-methyl-(1, 2, 3, 4, 5, 6, 7 or 8-)1,2,3,4-tetrahydronaphthyl]ethyl, 1-[2-ethyl-(1, 2, 3, 4, 5, 6, 7 or 8-)1,2,3,4-tetrahydronaphthyl]ethyl, 3-[3-propyl-(1, 2, 3, 4, 5, 6, 7 or 8-)1,2,3,4-tetrahydronaphthyl]propyl, 4-[(4-butyl-(1, 2, 3, 4, 5, 6, 7 or 8-)1,2,3,4-tetrahydronaphthyl]butyl, 5-[5-pentyl-(1, 2, 3, 4, 6, 7 or 8-)1,2,3,4-tetrahydronaphthyl]pentyl, 6-[6-hexyl-(1, 2, 3, 4, 5, 7 or 8-)1,2,3,4-tetrahydronaphthyl]hexyl, 1,1-dimethyl-2-[1,7-dimethyl-(1, 2, 3, 4, 5, 6 or 8-)1,2,3,4-tetrahydronaphthyl]ethyl, and 2-methyl-3-[1,1,4-trimethyl-(2, 3, 4, 5, 6, 7 or 8-)1,2,3,4-tetrahydronaphthyl]propyl groups.

Examples of the piperidinyl group which may have 1 to 3 lower alkyl groups as substituents on the piperidine ring include piperidinyl group which may have 1 to 3 linear or branched alkyl groups having 1 to 6 carbon atoms as substituents on the piperidine ring such as (1, 2, 3 or 4-)piperidinyl, 1-methyl-(2, 3 or 4-)piperidinyl, 1-ethyl-(2, 3 or 4-)piperidinyl, 1-propyl-(2, 3 or 4-)piperidinyl, 1-isopropyl-(2, 3 or 4-)piperidinyl, 1-butyl-(2, 3 or 4-)piperidinyl, 1-isobutyl-(2, 3 or 4-)piperidinyl, 1-tert-butyl-(2, 3 or 4-)piperidinyl, 1-pentyl-(2, 3 or 4-)piperidinyl, 1-hexyl-(2, 3 or 4-)piperidinyl, 1,2-dimethyl-(3, 4, 5 or 6-)piperidinyl, and 1,2,6-trimethyl-(3, 4 or 5-)piperidinyl groups.

Examples of the quinolyl lower alkyl group include quinolylalkyl groups whose alkyl moiety is a linear or branched alkyl group having 1 to 6 carbon atoms such as (2, 3, 4, 5, 6, 7 or 8-)quinolylmethyl, 2-[(2, 3, 4, 5, 6, 7 or 8-)quinolyl]ethyl, 1-[(2, 3, 4, 5, 6, 7 or 8-)quinolyl] ethyl, 3-[(2, 3, 4, 5, 6, 7 or 8-)quinolyl]propyl, 4-[(2, 3, 4, 5, 6, 7 or 8-) quinolyl]butyl, 5-[(2, 3, 4, 5, 6, 7 or 8-) quinolyl]pentyl, and 6-[(2, 3, 4, 5, 6, 7 or 8-) quinolyl]hexyl groups.

Examples of the 1,2,3,4-tetrazolyl lower alkyl group which may have, on the tetrazole ring, a substituent selected from the group consisting of a lower alkyl group and a phenyl lower alkyl group include 1,2,3,4-tetrazolylalkyl groups whose alkyl moiety is a linear or branched alkyl group having 1 to 6 carbon atoms and which may have, on the tetrazole ring, a substituent selected from the group consisting of a linear or branched alkyl group having 1 to 6 carbon atoms and a phenyl alkyl group whose alkyl moiety is a linear or branched alkyl group having 1 to 6 carbon atoms, such as [(1 or 5-)1,2,3,4-tetrazolyl]methyl, 2-[(1 or 5-)1,2,3,4-tetrazolyl]ethyl, 1-[(1 or 5-)1,2,3,4-tetrazolyl]ethyl, 3-[(1 or 5-)1,2,3,4-tetrazolyl]propyl, 4-[(1 or 5-)1,2,3,4-tetrazolyl]butyl, 5-[(1 or 5-)1,2,3,4-tetrazolyl]pentyl, 6-[(1 or 5-)1,2,3,4-tetrazolyl]hexyl, 5-[1-methyl-5-(1,2,3,4-tetrazolyl)]pentyl, 6-[1-methyl-5-(1,2,3,4-tetrazolyl)]hexyl, 5-methyl-1-(1,2,3,4-tetrazolyl)methyl, 2-[5-ethyl-1-(1,2,3,4-tetrazolyl]hexyl, 1,1-dimethyl-2-[(1 or 5-)1,2,3,4-tetrazoly)]ethyl, 2-methyl-3-[(1 or 5-)1,2,3,4-tetrazolyl]propyl, [1-methyl-5-(1,2,3,4-tetrazolyl)]methyl, [1-ethyl-5-(1,2,3,4-tetrazolyl)]methyl, 2-[1-propyl-5-(1,2,3,4-tetrazolyl)]ethyl, 1-[1-butyl-5-(1,2,3,4-tetrazolyl)]ethyl, 3-[1-pentyl-5-(1,2,3,4-tetrazolyl)]propyl, 3-[5-propyl-1-(1,2,3,4-tetrazolyl)]propyl, 4-[5-butyl-1-(1,2,3,4-tetrazolyl)]butyl, 5-[5-pentyl-1-(1,2,3,4-tetrazolyl)]pentyl, 6-[5-hexyl-1-(1,2,3,4-tetrazolyl)]hexyl, [1-ethyl-5-(1,2,3,4-tetrazolyl)]methyl, [1-benzyl-5-(1,2,3,4-tetrazolyl)]methyl, 1-[(2-phenylethyl)-5-(1,2,3,4-tetrazolyl)]methyl, 2-[1-(3-phenylpropyl)-5-(1,2,3,4-tetrazolyl)]ethyl, 1-[1-(4-phenylbutyl)-5-(1,2,3,4-tetrazolyl)]ethyl, 3-[1-(5-phenylpentyl)-5-(1,2,3,4-tetrazolyl)]propyl, 4-[1-(6-phenylhexyl)-5-(1,2,3,4-tetrazolyl)]butyl, 5-[1-(1,1-dimethyl-2-phenylethyl)-5-(1,2,3,4-tetrazolyl)]methyl, 6-[1-(2-methyl-3-phenylpropyl)-5-(1,2,3,4-tetrazolyl)]hexyl, 5-benzyl-1-(1,2,3,4-tetrazolyl)methyl, 2-[5-(1-phenylethyl)-1-(1,2,3,4-tetrazolyl)]ethyl, 3-[5-(3-phenylpropyl)-1-(1,2,3,4-tetrazolyl)]propyl, 4-[5-(4-phenylbutyl)-1-(1,2,3,4-tetrazolyl)]butyl, 5-[5-(5-phenylpentyl)-1-(1,2,3,4-tetrazolyl)]pentyl, and 6-[5-(6-phenylhexyl)-1-(1,2,3,4-tetrazolyl)]hexyl groups.

Examples of the thiazolyl lower alkyl group which may have a phenyl group as a substituent on the thiazole ring include thiazolylalkyl groups which may have 1 or 2 phenyl groups as substituents on the thiazole ring and whose alkyl moiety is a linear or branched alkyl group having 1 to 6 carbon atoms such as [(2, 4 or 5-)thiazolyl]methyl, 2-[(2, 4 or 5-)thiazolyl]ethyl, 1-[(2, 4 or 5-)thiazolyl]ethyl, 3-[(2, 4 or 5-)thiazolyl]propyl, 4-[(2, 4 or 5-)thiazolyl]butyl, 5-[(2, 4 or 5-)thiazolyl]pentyl, 6-[(2, 4 or 5-)thiazolyl]hexyl, 1,1-dimethyl-2-[(2, 4 or 5-)thiazolyl]ethyl, 2-methyl-3-[(2, 4 or 5-)thiazolyl]propyl, [2-phenyl-(4 or 5-)thiazolyl]methyl, 2-[4-phenyl-(2 or 5-)thiazolyl]ethyl, 1-[5-phenyl-(2 or 4-)thiazolyl]ethyl, 3-[2-phenyl-(2 or 5-)thiazolyl]propyl, 4-(2,4-diphenyl-5-thiazolyl)butyl, 5-(2,5-diphenyl-4-thiazolyl)pentyl, 6-(4,5-diphenyl-2-thiazolyl)hexyl, 1,1-dimethyl-2-[2-phenyl-(4 or 5-)thiazolyl]ethyl, 2-methyl-3-[4-phenyl-(2 or 5-)thiazolyl]propyl, [4-phenyl-(2 or 5-)thiazolyl]methyl, [5-phenyl-(2 or 4-)thiazolyl]methyl, (2,4-diphenyl-5-thiazolyl)methyl, (2,5-diphenyl-4-thiazolyl)methyl, and (4,5-diphenyl-2-thiazolyl)methyl groups.

Examples of the benzoyl lower alkyl group which may have, on the phenyl ring, 1 to 3 substituents selected from the group consisting of a lower alkoxy group and a halogen atom include benzoylalkyl groups which may have, on the phenyl ring, 1 to 3 substituents selected from the group consisting of a linear or branched alkoxy group having 1 to 6 carbon atoms and a halogen atom and whose alkyl moiety is a linear or branched alkyl group having 1 to 6 carbon atoms such as benzoylmethyl, 2-benzoylethyl, 1-benzoylethyl, 3-benzoylpropyl, 4-benzoylbutyl, 5-benzoylpentyl, 6-benzoylhexyl, 1,1-dimethyl-2-benzoylethyl, 2-methyl-3-benzoylpropyl, 4-fluorobenzoylmethyl, 2-chlorobenzoylmethyl, 3-chlorobenzoylmethyl, 4-chlorobenzoylmethyl, 2-(4-fluorobenzoyl)ethyl, 2-(4-chlorobenzoyl)ethyl, 3,4-dibromobenzoylmethyl, 3,4-diiodobenzoylmethyl, 2,4-difluorobenzoylmethyl, 2,5-dichlorobenzoylmethyl, 2,6-dichlorobenzoylmethyl, 3,4,5-trifluorobenzoylmethyl, 3-(4-chlorobenzoyl)propyl, 1-(2-bromobenzoyl)ethyl, 4-(3-fluorobenzoyl)butyl, 5-(4-iodobenzoyl)pentyl, 6-(4-chlorobenzoyl)hexyl, 1,1-dimethyl-2-(3-fluorobenzoyl)ethyl, 2-methyl-3-(4-chlorobenzoyl)propyl, 2-methoxybenzoylmethyl, 2-(3-methoxybenzoyl)ethyl, 2-(4-methoxybenzoyl)ethyl, 4-methoxybenzoylmethyl, 1-(2-ethoxybenzoyl)ethyl, 3-(3-ethoxybenzoyl)propyl, 4-(4-ethoxybenzoyl)butyl, 5-(4-isopropoxybenzoyl)pentyl, 6-(3-butoxybenzoyl)hexyl, 1,1-dimethyl-2-(4-pentyloxybenzoyl)ethyl, 2-methyl-3-(4-hexyloxybenzoyl)propyl, 3,4-dimethoxybenzoylmethyl, 3,4-diethoxybenzoylmethyl, 2,4-dimethoxybenzoylmethyl, 2,5-dimethoxybenzoylmethyl, 2,6-dimethoxybenzoylmethyl, 3,4,5-trimethoxybenzoylmethyl, 2-chloro-4-methoxybenzoylmethyl, and 3-fluoro-5-ethoxybenzoylmethyl groups.

Examples of the piperidinyl lower alkyl group which may have a lower alkyl group as a substituent on the piperidine ring include piperidinylalkyl groups which may have 1 to 3 linear or branched alkyl groups having 1 to 6 carbon atoms as substituents on the piperidine ring and whose alkyl moiety is a linear or branched alkyl group having 1 to 6 carbon atoms such as [(1, 2, 3 or 4-)piperidinyl]methyl, 2-[(1, 2, 3 or 4-)piperidinyl]ethyl, 1-[(1, 2, 3 or 4-)piperidinyl]ethyl, 3-[(1, 2, 3 or 4-)piperidinyl]propyl, 4-[(1, 2, 3 or 4-)piperidinyl]butyl, 5-[(1, 2, 3 or 4-)piperidinyl]pentyl, 6-[(1, 2, 3 or 4-)piperidinyl]hexyl, 1,1-dimethyl-2-[(1, 2, 3 or 4-)piperidinyl]ethyl, 2-methyl-3-[(1, 2, 3 or 4-)piperidinyl]propyl, [1-methyl-(2, 3 or 4-)piperidinyl]methyl, 2-[1-ethyl-(2, 3 or 4-)piperidinyl]ethyl, 1-[4-propyl-(1, 2 or 3-)piperidinyl]ethyl, 3-[3-isopropyl-(1, 2, 4, 5 or 6-)piperidinyl]propyl, 4-[2-butyl-(1, 3, 4, 5 or 6-)piperidinyl]butyl, 5-[1-isobutyl-(2, 3 or 4-)piperidinyl] pentyl, 6-[1-tert-butyl-(2, 3 or 4-)piperidinyl]hexyl, 1,1-dimethyl-2-[4-pentyl-(1, 2 or 3-)piperidinyl]ethyl, 2-methyl-3-[1-hexyl-(2, 3 or 4-)piperidinyl]propyl, [1,2-dimethyl-(3, 4, 5 or 6-)piperidinyl]methyl, and [1,2,6-trimethyl-(3, 4 or 5-)piperidinyl]methyl groups.

Examples of the imidazolyl group which may have 1 to 3 phenyl groups as substituents on the imidazole ring include imidazolyl groups which may have 1 to 3 phenyl groups as substituents on the imidazole ring such as (1, 2, 4 or 5-)imidazolyl, 1-phenyl-(2, 4 or 5-)imidazolyl, 2-phenyl-(1, 4 or 5-)imidazolyl, 4-phenyl-(1, 2 or 5-)imidazolyl, 5-phenyl-(1, 2 or 4-)imidazolyl, 1,2-diphenyl-(4 or 5-)imidazolyl, 2,4-diphenyl-(1 or 5-)imidazolyl, 4,5-diphenyl-(1 or 2-)imidazolyl, 2,5-diphenyl-(1 or 4-)imidazolyl, and 2,4,5-triphenyl-1-imidazolyl groups.

Examples of the benzimidazolyl group which may have 1 to 3 lower alkyl groups as substituents on the benzimidazole ring include benzimidazolyl group which may have 1 to 3 linear or branched alkyl groups having 1 to 6 carbon atoms as substituents on the benzimidazole ring such as (1, 2, 4, 5, 6 or 7-)benzimidazolyl, 1-methyl-(2, 4, 5, 6 or 7-)benzimidazolyl, 2-ethyl-(1, 4, 5, 6 or 7-)benzimidazolyl, 4-propyl-(1, 2, 5, 6 or 7-)benzimidazolyl, 5-butyl-(1, 2, 4, 6 or 7-)benzimidazolyl, 6-pentyl-(1, 2, 4, 5 or 7-)benzimidazolyl, 7-hexyl-(1, 2, 4, 5 or 6-)benzimidazolyl, 1-ethyl-(2, 4, 5, 6 or 7-)benzimidazolyl] hexyl, 1-butyl-(2, 4, 5, 6 or 7-)benzimidazolyl, 1-isopropyl-(1, 2, 4, 5, 6 or 7-)benzimidazolyl, 1,2-dimethyl-(4, 5, 6 or 7-)benzimidazolyl, 1-methyl-4-ethyl-(2, 5, 6 or 7-)benzimidazolyl, 1-propyl-5-methyl-(2, 4, 6 or 7-)benzimidazolyl, and 1,2,5-trimethyl-(2, 4, 5, 6 or 7-)benzimidazolyl groups.

Examples of the pyridyl lower alkoxy group include pyridylalkoxy groups whose alkyl moiety is a linear or branched alkyl group having 1 to 6 carbon atoms such as (2, 3 or 4-)pyridylmethoxy, 2-[(2, 3 or 4-)pyridyl]ethoxy, 1-[(2, 3 or 4-)pyridyl]ethoxy, 3-[(2, 3 or 4-)pyridyl]propoxy, 4-[(2, 3 or 4-)pyridyl]butoxy, 1-1-dimethyl-2-[(2, 3 or 4-)pyridyl]ethoxy, 5-[(2, 3 or 4-)pyridyl]pentyloxy, 6-[(2, 3 or 4-)pyridyl]hexyloxy, 1-[(2, 3 or 4-)pyridyl]isopropoxy, and 2-methyl-3-[(2, 3 or 4-)pyridyl]propoxy groups.

Examples of the 1,2,3,4-tetrahydroquinolyl lower alkyl group which may have an oxo group as a substituent on the tetrahydroquinoline ring include 1,2,3,4-tetrahydroquinolylalkyl groups which may have 1 or 2 oxo groups as substituents on the tetrahydroquinoline ring and whose alkyl moiety is a linear or branched alkyl group having 1 to 6 carbon atoms such as (1, 2, 3, 4, 5, 6, 7 or 8-)1,2,3,4-tetrahydroquinolylmethyl, 2-[(1, 2, 3, 4, 5, 6, 7 or 8-)1,2,3,4-tetrahydroquinolyl]ethyl, 1-[(1, 2, 3, 4, 5, 6, 7 or 8-)1,2,3,4-tetrahydroquinolyl]ethyl, 3-[(1, 2, 3, 4, 5, 6, 7 or 8-)1,2,3,4-tetrahydroquinolyl]propyl, 4-[(1, 2, 3, 4, 5, 6, 7 or 8-)1,2,3,4-tetrahydroquinolyl]butyl, 5-[(1, 2, 3, 4, 5, 6, 7 or 8-)1,2,3,4-tetrahydroquinolyl]pentyl, 6-[(1, 2, 3, 4, 5, 6, 7 or 8-)1,2,3,4-tetrahydroquinolyl]hexyl, 1,1-dimethyl-2-[(1, 2, 3, 4, 5, 6, 7 or 8-)1,2,3,4-tetrahydroquinolyl]ethyl, 2-methyl-3-[(1, 2, 3, 4, 5, 6, 7 or 8-)1,2,3,4-tetrahydroquinolyl]propyl, [2-oxo-(1, 3, 4, 5, 6, 7 or 8-)1,2,3,4-tetrahydroquinolyl]methyl, [4-oxo-(1, 2, 3, 5, 6, 7 or 8-)1,2,3,4-tetrahydroquinolyl]methyl, [2,4-dioxo-(1, 3, 5, 6, 7 or 8-)1,2,3,4-tetrahydroquinolyl]methyl, 2-[2-oxo-(1, 3, 4, 5, 6, 7 or 8-)1,2,3,4-tetrahydroquinolyl]ethyl, 3-[4-oxo-(1, 2, 3, 5, 6, 7 or 8-)1,2,3,4-tetrahydroquinolyl]propyl, 4-[2, 4-dioxo-(1, 3, 5, 6, 7 or 8-)1,2,3,4-tetrahydroquinolyl]butyl, 5-[2-oxo-(1, 3, 4, 5, 6, 7 or 8-)1,2,3,4-tetrahydroquinolyl] pentyl, and 6-[4-oxo-(1, 2, 3, 5, 6, 7 or 8-)1,2,3,4-tetrahydroquinolyl]hexyl groups.

Examples of the 1,3,4-oxadiazolyl lower alkyl group which may have an oxo group as a substituent on the 1,3,4-oxadiazole ring include 1,3,4-oxadiazolylalkyl groups which may have an oxo group as a substituent on the 1,3,4-oxadiazole ring and whose alkyl moiety is a linear or branched alkyl group having 1 to 6 carbon atoms such as (2 or 5-)1,3,4-oxadiazolylmethyl, 2-[(2 or 5-)1,3,4-oxadiazolyl]ethyl, 1-[(2 or 5-)1,3,4-oxadiazolyl]ethyl, 3-[(2 or 5-)1,3,4-oxadiazolyl]propyl, 4-[(2 or 5-)1,3,4-oxadiazolyl]butyl, 5-[(2 or 5-)1,3,4-oxadiazolyl]pentyl, 6-[(2 or 5-)1,3,4-oxadiazolyl]hexyl, 1,1- dimethyl-2-[(2 or 5-)1,3,4-oxadiazolyl]ethyl, 2-methyl-3-[(2 or 5-)1,3,4-oxadiazolyl]propyl, 2-oxo-[(3 or 5-)1,3,4-oxadiazolyl]methyl, 5-oxo-[(2 or 3-)1,3,4-oxadiazolyl]methyl, 2-[2-oxo-(3 or 5-)(1,3,4-oxadiazolyl)]ethyl, 1-[5-oxo-(2 or 3-)1,3,4-oxadiazolyl]ethyl, 3-[(2 or 5-)1,3,4-oxadiazolyl]propyl, 4-[2-oxo(3 or 5-)1,3,4-oxadiazolyl]butyl, 5-[5-oxo(2 or 3-)1,3,4-oxadiazolyl]pentyl, 6-[2-oxo(3 or 5-)1,3,4-oxadiazolyl]hexyl, 1,1-dimethyl-2-[5-oxo(2 or 3-)1,3,4-oxadiazolyl]ethyl, and 2-methyl-3-[2-oxo(3 or 5-)1,3,4-oxadiazolyl]propyl groups.

Examples of the thienyl lower alkyl group include thienylalkyl groups whose alkyl moiety is a linear or branched alkyl group having 1 to 6 carbon atoms such as (2 or 3-)thienylmethyl, 2-[(2 or 3-)thienyl]ethyl, 1-[(2 or 3-)thienyl]ethyl, 3-[(2 or 3-)thienyl]propyl, 4-[(2 or 3-)thienyl]butyl, 5-[(2 or 3-)thienyl]pentyl, 6-[(2 or 3-)thienyl]hexyl, 1,1-dimethyl-2-[(2 or 3-)thienyl]ethyl, and 2-methyl-3-[(2 or 3-)thienyl]propyl groups.

Examples of the pyrimidinylcarbonyl group which may have an oxo group as a substituent on the pyrimidine ring include pyrimidinylcarbonyl groups which may have 1 to 3 oxo groups as substituents on the pyrimidine ring such as (2, 3, 4 or 6-)pyrimidinylcarbonyl, 2,6-dioxo-(1, 3, 4 or 5-)pyrimidinylcarbonyl, 2-oxo-(1, 3, 4, 5 or 6-)pyrimidinylcarbonyl, 6-oxo-(1, 2, 3, 4 or 5-)pyrimidinylcarbonyl, 4-oxo-(1, 2, 3, 5 or 6-)pyrimidinylcarbonyl, 2,4-dioxo-(1, 3, 4 or 6-)pyrimidinylcarbonyl, and 2,4,6-trioxo-(1, 3 or 5-)pyrimidinylcarbonyl groups.

Examples of the lower alkoxy lower alkoxy group include linear or branched alkoxy groups having 1 to 6 carbon atoms which may have a linear or branched alkoxy group having 1 to 6 carbon atoms as a substituent such as methoxymethoxy, 1-ethoxyethoxy, 2-methoxyethoxy, 2-propoxyethoxy, 3-isopropoxypropoxy, 4-butoxybutoxy, 5-pentyloxypentyloxy, 6-hexyloxyhexyloxy, 1,1-dimethyl-2-methoxyethoxy, 2-methyl-3-ethoxypropoxy, and 3-methoxypropoxy groups.

Examples of the lower alkoxycarbonyl lower alkoxy group include alkoxycarbonylalkoxy groups whose two alkoxy moieties are linear or branched alkoxy groups having 1 to 6 carbon atoms such as methoxycarbonylmethoxy, ethoxycarbonylmethoxy, 2-methoxycarbonylethoxy, 2-ethoxycarbonylethoxy, 1-ethoxycarbonylethoxy, 3-methoxycarbonylpropoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, and hexyloxycarbonylmethoxy groups.

Examples of the carboxy lower alkoxy group include carboxyalkoxy groups whose alkoxy moiety is a linear or branched alkoxy group having 1 to 6 carbon atoms such as carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, and 2-methyl-3-carboxypropoxy groups.

Examples of the phenoxy lower alkanoyl group include phenoxyalkanoyl groups whose alkanoyl moiety is a linear or branched alkanoyl group having 2 to 6 carbon atoms such as 2-phenoxyacetyl, 3-phenoxypropionyl, 2-phenoxypropionyl, 4-phenoxybutyryl, 5-phenoxypentanoyl, 6-phenoxyhexanoyl, 2,2-dimethyl-2-phenoxypropionyl, and 2-methyl-3-phenoxypropionyl groups.

Examples of the 1,2,3,4-tetrahydroquinolylcarbonyl group which may have an oxo group as a substituent on the tetrahydroquinoline ring include 1,2,3,4-tetrahydroquinolylcarbonyl groups which may have 1 or 2 oxo groups as substituents on the tetrahydroquinoline ring such as [(1, 3, 4, 5, 6, 7 or 8-)1,2,3,4-tetrahydroquinolyl]carbonyl, [2-oxo-(1, 3, 4, 5, 6, 7 or 8-)1,2,3,4-tetrahydroquinolyl]carbonyl, [4-oxo-(1, 2, 3, 5, 6, 7 or 8-)1,2,3,4-tetrahydroquinolyl]carbonyl, and [2,4-dioxo-(1, 3, 5, 6, 7 or 8-)1,2,3,4-tetrahydroquinolyl]carbonyl groups.

Examples of the 1,2,3,4-tetrahydroquinolyl group which may have an oxo group as a substituent on the tetrahydroquinoline ring include 1,2,3,4-tetrahydroquinolyl groups which may have 1 or 2 oxo groups as substituents on the tetrahydroquinoline ring such as (1, 2, 3, 4, 5, 6, 7 or 8-)1,2,3,4-tetrahydroquinolyl, 2-oxo-(1, 3, 4, 5, 6, 7 or 8-)1,2,3,4-tetrahydroquinolyl, 4-oxo-(1, 2, 3, 5, 6, 7 or 8-)1,2,3,4-tetrahydroquinolyl, and 2,4-dioxo-(1, 3, 5, 6, 7 or 8-)1,2,3,4-tetrahydroquinolyl groups.

Examples of the amino group which may have a lower alkoxycarbonyl group as a substituent include amino groups which may have an alkoxycarbonyl group whose akloxy moiety is a linear or branched alkoxy group having 1 to 6 carbon atoms such as amino, methoxycarbonylamino, ethoxycarbonylamino, propoxycarbonylamino, isopropoxycarbonylamino, butoxycarbonylamino, tert-butoxycarbonylamino, pentyloxycarbonylamino, and hexyloxycarbonylamino groups.

Examples of the benzoyl group which may have 1 to 3 lower alkoxy groups as substituents on the phenyl ring include benzoyl groups which may have 1 to 3 linear or branched alkoxy groups having 1 to 6 carbon atoms as substituents on the phenyl ring such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isopropoxybenzoyl, 3-butoxybenzoyl, 4-pentyloxybenzoyl, 4-hexyloxybenzoyl, 3,4-dimethoxybenzoyl, 3,4-diethoxybenzoyl, 2,4-dimethoxybenzoyl, 2,5-dimethoxybenzoyl, 2,6-dimethoxybenzoyl, and 3,4,5-trimethoxybenzoyl groups.

Examples of the lower alkyl group which have 1 or 2 phenyls which may have, on the phenyl ring, 1 to 3 substituents selected from the group consisting of a lower alkoxycarbonyl group, a cyano group, a nitro group, a phenyl group, a halogen atom, a lower alkyl group which may have a halogen atom as a substituent, a lower alkoxy group which may have a halogen atom as a substituent, and a lower alkylthio group include, in addition to the above described phenyl lower alkyl groups, linear or branched alkyl groups which have 1 to 6 carbon atoms and 1 to 2 phenyls which may have, on the phenyl ring, 1 to 3 substituents selected from the group consisting of an alkoxycarbonyl group whose akloxy moiety is a linear or branched alkoxy group having 1 to 6 carbon atoms, a cyano group, a nitro group, a phenyl group, a halogen atom, a linear or branched alkyl group having 1 to 6 carbon atoms which may have 1 to 3 halogen atoms as substituents, a linear or branched alkoxy group having 1 to 6 carbon atoms which may have 1 to 3 halogen atoms as substituents, and a linear or branched alkylthio group having 1 to 6 carbon atoms such as 1,1-diphenylmethyl, 1,1-di(4-fluorophenyl)methyl, 1-phenyl-1-(4-methoxyphenyl)methyl, 3,3-diphenylpropyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, 3,4-dimethoxybenzyl, 3,5-dimethoxybenzyl, 2-chlorobenzyl, 3-chlorobenzyl, 4-chlorobenzyl, 2-methylbenzyl, 3-methylbenzyl, 4-methylbenzyl, 3,4-dimethylbenzyl, 2,3-dimethylbenzyl, 2-methoxybenzyl, 3-methoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-methoxycarbonylbenzyl, 3-methoxycarbonylbenzyl, 4-tert-butylbenzyl, 4-ethylbenzyl, 4-isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 4-phenylbenzyl, 3,3-diphenylpropyl, 3-methyl-4-nitrobenzyl, 4-(4-methoxyphenyl)butyl, 2-(4-methylphenyl)ethyl, 4-tert-butoxycarbonylbenzyl, 3-chloro-6-methoxybenzyl, 4-nitro-3-methylbenzyl, 4-tert-butyrylbenzyl, 2-(2-ethoxycarbonylphenyl)ethyl, 1-(3-propoxycarbonylphenyl)ethyl, 3-(4-pentyloxycarbonylphenyl)propyl, 4-(3-hexyloxycarbonylphenyl)butyl, 5-(3,4-dimethoxycarbonylphenyl)pentyl, 6-(3,4,5-diethoxycarbonylphenyl)hexyl, 1,1-dimethyl-2-(4-butoxycarbonylphenyl)ethyl, 2-methyl-3-(4-methoxycarbonylphenyl)propyl, 2-(2-cyanophenyl)ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl)ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl) hexyl, 1,1-dimethyl-2-(2,4-dinitrophenyl)ethyl, 2-methyl-3-(2,4,6-trinitrophenyl)propyl, 2-(2-phenylphenyl)ethyl, 1-(3-phenylphenyl)ethyl, 3-(4-phenylphenyl)propyl, 4-(2-phenylphenyl)butyl, 5-(3-phenylphenyl)pentyl, 6-(4-phenylphenyl)hexyl, 1,1-dimethyl-2-(2,4-diphenylphenyl)ethyl, 2-methyl-3-(2,4,6-triphenylphenyl)propyl, 2-(2-fluorophenyl)ethyl, 1-(3-bromophenyl)ethyl, 3-(4-iodophenyl)propyl, 4-(2-bromophenyl)butyl, 5-(3-chlorophenyl)pentyl, 6-(4-bromophenyl)hexyl, 1,1-dimethyl-2-(2,4-dichlorophenyl)ethyl, 2-methyl-3-(2,4,6-trifluorophenyl)propyl, 2-(2-ethylphenyl)ethyl, 1-(3-propylphenyl)ethyl, 3-(4-butylphenyl)propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl)phenyl]propyl, 2-(2-ethoxyphenyl)ethyl, 1-(3-propoxyphenyl)ethyl, 3-(4-butoxyphenyl)propyl, 4-(2-pentyloxyphenyl)butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri(trifluoromethoxy)phenyl]propyl, 2-methylthiobenzyl, 3-methylthiobenzyl, 4-methylthiobenzyl, 2,4-dimethylthiobenzyl, 2,3-dimethylthiobenzyl, 2-(2-ethylthiophenyl) ethyl, 2-(4-methylthiophenyl)ethyl, 1-(3-propylthiophenyl) ethyl, 3-(4-butylthiophenyl)propyl, 4-(2-pentylthiophenyl) butyl, 5-(3-hexylthiophenyl)pentyl, 6-(4-methylthiophenyl) hexyl, 1,1-dimethyl-2-(2,4-dimethylthiophenyl)ethyl, 2-methyl-3-[2,4, 6-trimethylthiophenyl]propyl, 2-methyl-4-cyanobenzyl, 3-ethoxy-4-ethoxycarbonylbenzyl, 4-phenyl-3-nitrobenzyl, 3-fluoro-4-methoxybenzyl, 4-trifluoromethyl-3-cyanobenzyl, and 3-trifluoromethoxy-3-fluorobenzyl groups.

Examples of the phenyl group which may have, on the phenyl ring, 1 to 3 groups selected from the group consisting of a lower alkoxy group which may have a halogen atom as a substituent and a lower alkyl group which may have a halogen atom as a substituent include phenyl groups which may have, on the phenyl ring, 1 to 3 groups selected from the group consisting of a linear or branched alkoxy group having 1 to 6 carbon atoms which may have 1 to 3 halogen atoms as substituents and a linear or branched alkyl group having 1 to 6 carbon atoms and which may have 1 to 3 halogen atoms as substituents such as phenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, and 3-ethyl-4-trichloromethylphenyl groups.

Examples of the pyrrolidinyl lower alkyl group which may have, on the pyrrolidine ring, 1 to 3 lower alkyl groups which may have a hydroxyl group as a substituent include pyrrolidinylalkyl groups which may have, on the pyrrolidine ring, 1 to 3 linear or branched alkyl groups having 1 to 6 carbon atoms which may have 1 to 3 hydroxyl groups as substituents and whose alkyl moiety is a linear or branched alkyl group having 1 to 6 carbon atoms such as [(1, 2 or 3-)pyrrolidinyl]methyl, 2-[(1, 2 or 3-)pyrrolidinyl]ethyl, 1-[(1, 2 or 3-)pyrrolidinyl] ethyl, 3-[(1, 2 or 3-)pyrrolidinyl]propyl, 4-[(1, 2 or 3-)pyrrolidinyl]butyl, 5-[(1, 2 or 3-)pyrrolidinyl]pentyl, 6-[(1, 2 or 3-)pyrrolidinyl]hexyl, 1,1-dimethyl-2-[(1, 2 or 3-)pyrrolidinyl]ethyl, 2-methyl-3-[(1, 2 or 3-)pyrrolidinyl]propyl, [1-methyl-(2 or 3-)pyrrolidinyl]methyl, 2-[2-ethyl-(1, 3, 4 or 5-)pyrrolidinyl]ethyl, 1-[3-propyl-(1, 2, 4 or 5-)pyrrolidinyl]ethyl, 3-[1-butyl-(2 or 3-)pyrrolidinyl]propyl, 4-[2-pentyl-(1, 3, 4 or 5-)pyrrolidinyl]butyl, 5-[3-hexyl-(1, 2, 4 or 5-)pyrrolidinyl]pentyl, 6-[1,2-dimethyl-(3, 4 or 5-)pyrrolidinyl] hexyl, 1,1-dimethyl-2-[1,2,3-trimethyl-(4 or 5-)pyrrolidinyl] ethyl, 2-methyl-3-[1-ethyl-2-methyl-(3, 4 or 5-)pyrrolidinyl] propyl, [1-(2-hydroxyethyl)-(2 or 3-)pyrrolidinyl]methyl, [2-hydroxymethyl-(1, 3, 4 or 5-)pyrrolidinyl]methyl, 2-[2-hydroxymethyl-(1, 3, 4 or 5-)pyrrolidinyl]ethyl, 1-[3-(3-hydroxypropyl)-(1, 2, 4 or 5-)pyrrolidinyl]ethyl, 3-[1-(4-hydroxybutyl)-(2 or 3-)pyrrolidinyl]propyl, 4-[2-(5-hydroxypentyl)-(1, 3, 4 or 5-)pyrrolidinyl]butyl, 5-[3-(6-hydroxyhexyl)-(1, 2, 4 or 5-)pyrrolidinyl]pentyl, 6-[1,2-dihydroxymethyl-(3, 4 or 5-)pyrrolidinyl]hexyl, 1,1-dimethyl-2-[1,2,3-trihydroxymethyl-(4 or 5-)pyrrolidinyl] ethyl, 2-methyl-3-[2-(1,2-hydroxyethyl)-(1, 3, 4 or 5-)pyrrolidinyl]propyl, and [2-(2,3,4-trihydroxybutyl)-(1, 3, 4 or 5-)pyrrolidinyl]methyl groups.

Examples of the amino substituted lower alkyl group which may have a substituent selected from the group consisting of a phenyl group and a lower alkyl group include linear or branched alkyl groups having 1 to 6 carbon atoms substituted with an amino group which may have 1 or 2 substituents selected from the group consisting of a phenyl group and a linear or branched alkyl group having 1 to 6 carbon atoms such as aminomethyl, 2-aminomethyl, 1-aminoethyl, 3-aminopropyl, 4-aminobutyl, 5-aminopentyl, 6-aminohexyl, 1,1-dimethyl-2-aminoethyl, N,N-diethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N-methyl-N-hexylamino)ethyl, phenylaminomethyl, 1-phenylaminoethyl, 2-phenylaminoethyl, 3-phenylaminopropyl, 4-phenylaminobutyl, 5-phenylaminopentyl, 6-phenylaminohexyl, N-methyl-N-phenylaminomethyl, 2-(N-ethyl-N-phenylamino)ethyl, (N-ethyl-N-phenylamino)methyl, and 2-(N-methyl-N-phenylamino)ethyl groups.

Examples of the tetrahydrofuryl lower alkyl group which may have a hydroxyl group as a substituent on the lower alkyl group include tetrahydrofurylalkyl groups which may have a hydroxyl group as a substituent on the lower alkyl group and whose alkyl moiety is a linear or branched alkyl group having 1 to 6 carbon atoms such as [(2 or 3-)tetrahydrofuryl]methyl, 2-[(2 or 3-)tetrahydrofuryl]ethyl, 1-[(2 or 3-)tetrahydrofuryl]ethyl, 3-[(2 or 3-)tetrahydrofuryl]propyl, 4-[(2 or 3-)tetrahydrofuryl]butyl, 5-[(2 or 3-)tetrahydrofuryl]pentyl, 6-[(2 or 3-)tetrahydrofuryl]hexyl, 1,1-dimethyl-2-[(2 or 3-)tetrahydrofuryl]ethyl, 2-methyl-3-[(2 or 3-)tetrahydrofuryl]propyl, 1-hydroxy-1-[(2 or 3-)tetrahydrofuryl]methyl, 2-hydroxy-2-[(2 or 3-)tetrahydrofuryl]ethyl, 2-hydroxy-1-[(2 or 3-)tetrahydrofuryl]ethyl, 3-hydroxy-3-[(2 or 3-)tetrahydrofuryl]propyl, 4-hydroxy-4-[(2 or 3-)tetrahydrofuryl]butyl, 5-hydroxy-5-[(2 or 3-)tetrahydrofuryl]pentyl, 6-hydroxy-6-[(2 or 3-)tetrahydrofuryl]hexyl, 2-hydroxy-1,1-dimethyl-2-[(2 or 3-)tetrahydrofuryl]ethyl, and 3-hydroxy-2-methyl-3-[(2 or 3-)tetrahydrofuryl]propyl groups.

Examples of the phenoxy lower alkyl group which may have, on the phenyl ring, 1 to 3 substituents selected from the group consisting of a lower alkyl group and a nitro group include, in addition to the above described phenoxy lower alkyl groups, phenoxyalkyl groups which may have, on the phenyl ring, 1 to 3 substituents selected from the group consisting of a linear or branched alkyl group having 1 to 6 carbon atoms and a nitro group and whose alkyl moiety is a linear or branched alkyl group having 1 to 6 carbon atoms such as 2-methylphenoxymethyl, 3-methylphenoxymethyl, 4-methylphenoxymethyl, 3,4-dimethylphenoxymethyl, 2,3-dimethylphenoxymethyl, 3,4,5-trimethylphenoxymethyl, 2-(2-ethylphenoxy)ethyl, 2-(3-methylphenoxy)ethyl, 2-(4-methylphenoxy)ethyl, 1-(3-propylphenoxy)ethyl, 3-(4-butylphenoxy)propyl, 4-(2-pentylphenoxy)butyl, 5-(3-hexylphenoxy)pentyl, 6-(4-methylphenoxy)hexyl, 1,1-dimethyl-2-(2,4-dimethylphenoxy)ethyl, 2-methyl-3-(2,4,6-trimethylphenoxy)propyl, 2-(4-nitro-3-methylphenoxy)ethyl, 4-nitrophenoxymethyl, 3-nitrophenoxymethyl, 2-nitrophenoxymethyl, 2-(2-nitrophenoxy)ethyl, 2-(4-nitrophenoxy)ethyl, 1-(3-nitrophenoxy)ethyl, 3-(4-nitrophenoxy)propyl, 4-(2-nitrophenoxy)butyl, 5-(3-nitrophenoxy)pentyl, 6-(4-nitrophenoxy)hexyl, 1,1-dimethyl-2-(2,4-dinitrophenoxy)ethyl, and 2-methyl-3-(2,4,6-trinitrophenoxy)propyl groups.

Examples of the phenyl lower alkanoyl group include phenylalkanoyl groups whose alkanoyl moiety is a linear or branched alkanoyl group having 2 to 6 carbon atoms such as 2-phenylacetyl, 3-phenylpropionyl, 2-phenylpropionyl, 4-phenylbutyryl, 5-phenylpentanoyl, 6-phenylhexanoyl, 2,2-dimethyl-3-phenylpropionyl, and 2-methyl-3-phenylpropionyl groups.

Examples of the phenyl group which may have, on the phenyl ring, 1 to 3 substituents selected from the group consisting of a halogen atom and a lower alkyl group which may have a halogen atom include phenyl groups which may have, on the phenyl ring, 1 to 3 substituents selected from the group consisting of a halogen atom and a linear or branched alkyl group having 1 to 6 carbon atoms which may have 1 to 3 halogen atoms such as phenyl, 3,4-difluorophenyl, 2-fluorophenyl, 3-bromophenyl, 4-iodophenyl, 4-methylphenyl, 2-methylphenyl, 3-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl, 2-chloro-4-trifluoromethylphenyl, 3-ethyl-4-fluorophenyl, 3-fluoro-4-trichloromethylphenyl, 2-methyl-3-trifluoromethyl-4-trifluoromethylphenyl, 3-fluorophenyl, 4-fluorophenyl, 2-bromophenyl, 4-bromophenyl, 2-iodophenyl, 3-iodophenyl, 2,3-dibromophenyl, 2,4-diiodophenyl, 2,5-difluorophenyl, 2,6-dichlorophenyl, 2,4,6-trichlorophenyl, 2,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trifluorophenyl, and 2,4-difluorophenyl groups.

Examples of the 5-to 7-membered saturated heterocyclic group formed by mutually binding $R^{20}$ and $R^{21}$, $R^{22}$ and $R^{23}$, $R^{26}$ and $R^{27}$, $R^{29}$ and $R^{30}$ or $R^{32}$ and $R^{33}$ together with the nitrogen atoms bound to them, through or not through a nitrogen atom, an oxygen atom or a sulfur atom, include pyrrolidinyl, piperidinyl, piperazinyl, morpholino, thiomorpholino, and homopiperazinyl groups.

Examples of the phenoxy lower alkyl group which may have, on the phenyl ring, a lower alkyl group as a substituent include, in addition to the above described phenoxy lower alkyl groups, phenoxyalkyl groups which may have, on the phenyl ring, 1 to 3 linear or branched alkyl groups having 1 to 6 carbon atoms as substituents and whose alkyl moiety is a linear or branched alkyl group having 1 to 6 carbon atoms such as 2-methylphenoxymethyl, 3-methylphenoxymethyl, 4-methylphenoxymethyl, 3,4-dimethylphenoxymethyl, 2,3-dimethylphenoxymethyl, 3,4,5-trimethylphenoxymethyl, 2-(2-ethylphenoxy)ethyl, 2-(4-methylphenoxy)ethyl, 1-(3-propylphenoxy)ethyl, 3-(4-butylphenoxy)propyl, 4-(2-pentylphenoxy)butyl, 5-(3-hexylphenoxy)pentyl, 6-(4-methylphenoxy)hexyl, 1,1-dimethyl-2-(2,4-dimethylphenoxy)ethyl, and 2-methyl-3-(2,4,6-trimethylphenoxy)propyl groups.

A compound represented by the general formula (1) or a salt thereof is more preferred, wherein
$X_1$ represents a nitrogen atom or a group —CH═,
$R^1$ represents a group —Z—$R^6$, Z represents a group —N(R$^8$)—B—, a group —B—N(R$^8$)—, a group —B$_0$—O— or a group —N(R$^{9a}$)—CO—N(R$^{9b}$)—, R$^8$ represents a hydrogen atom, a lower alkyl group that may have a lower alkoxy group as a substituent, a lower alkanoyl group, a lower alkylsulfonyl group or a phenyl lower alkyl group, B represents a group —CO— or a lower alkylene group, B$_0$ represents a lower alkylene group, R$^{9a}$ represents a hydrogen atom or a lower alkyl group, R$^{9b}$ represents a hydrogen atom or a lower alkyl group, R$^6$ represents a group

[Formula 58]

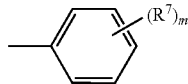

R$^7$ represents a halogen atom or a lower alkyl group that may have a halogen atom as a substituent, m represents an integer of 1 or 2 (when m represents 2, two R$^7$s may be identical or different) and R$^2$ represents a hydrogen atom, a halogen atom, or a lower alkyl group, Y represents a group —O—, or a group —N(R$^5$)—, R$^5$ represents a hydrogen atom, or a lower alkyl group, A represents a group

[Formula 59]

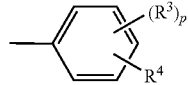

p represents 1 or 2,

R$^3$ represents a hydrogen atom, a lower alkoxy group, a halogen atom, or a lower alkyl group that may have a halogen atom as a substituent, R$^4$ represents a group -(T)$_l$-N(R$^{14}$)R$^{15}$, T represents a group —N(R$^{17}$)—B$_3$—CO—, a group —B$_4$—CO—, or a group —CO—, R$^{17}$ represents a hydrogen atom, or a lower alkyl group, B$_3$ represents a lower alkylene group, B$_4$ represents a lower alkenylene group or a lower alkylene group that may have a hydroxyl group as a substituent, l represents 0 or 1, R$^{14}$ represents a hydrogen atom or an alkyl group that may have a hydroxyl group as a substituent, R$^{15}$ represents (36a) a piperazinyl-substituted oxalyl group that may have 1 to 3 groups selected from the group consisting of a phenyl lower alkyl group (that may have 1 to 3 groups selected from the group consisting of a lower alkylenedioxy group and a lower alkoxy group as a substituent(s) on the phenyl ring) and a pyridyl lower alkyl group as a substituent(s) on the piperazine ring, R$^{14}$ and R$^{15}$, together with the nitrogen atom to which they bind, form a heterocyclic group which is piperidinyl or piperazinyl group, wherein the heterocyclic ring may be substituted by a group selected from the group consisting of (28) a phenyl-substituted lower alkyl group that may be substituted by a group, on the phenyl ring, selected from the group consisting of a lower alkanoyl group, an amino group that may have a lower alkanoyl group as a substituent, a lower alkoxycarbonyl group, a cyano group, a nitro group, a phenyl group, a halogen atom, a lower alkyl group that may have a halogen atom as a substituent, a lower alkoxy group that may have a halogen atom as a substituent, a phenyl lower alkoxy group, a hydroxyl group, and a lower alkylenedioxy group (49) a group) —(B$_{12}$CO)t-N(R$^{20}$)R$^{21}$, or (84) a group —(O—B$_{15}$)s-CO—N(R$^{26}$)R$^{27}$, B$_{12}$ represents a lower alkylene group, t represents 0 or 1, R$^{20}$ and R$^{21}$, together with the nitrogen atom to which they bind, form a saturated heterocyclic group which is piperidinyl or piperazinyl group that, on the heterocyclic ring, may be substituted by a phenyl lower alkyl group that may have a lower alkylenedioxy group as a substituent on the phenyl ring, B$_{15}$ represents a lower alkylene group, s represents 0 or 1, R$^{26}$ and R$^{27}$ may be identical or different and each represent a hydrogen atom, a lower alkyl group, a phenyl lower alkyl group, or an imidazolyl lower alkyl group, and R$^{26}$ and R$^{27}$, together with the nitrogen atom to which they bind, may bind to each other, directly or via a nitrogen atom, oxygen atom, or sulfur atom to form a 5- to 7-membered saturated heterocyclic ring, (wherein the heterocyclic ring may be substituted by 1 to 3 phenyl lower alkyl groups that may have a lower alkylenedioxy group on the phenyl ring).

For example, a compound represented by the general formula (1) or a salt thereof is further more preferred, wherein X$_1$ represents a nitrogen atom, R$^1$ represents a group —Z—R$^6$, Z represents a group —N(R$^8$)—B—, R$^8$ represents a hydrogen atom, or a lower alkyl group that may have a lower alkoxy group as a substituent, B represents a group —CO—, R$^6$ represents a group

[Formula 60]

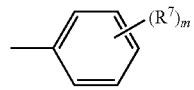

R$^7$ represents a halogen atom or a lower alkyl group that may have a halogen atom as a substituent, m represents an integer of 1 or 2 (when m represents 2, two R's may be identical or different) and R$^2$ represents a hydrogen atom, Y represents a group —O—, or a group —N(R$^5$)—, R$^5$ represents a hydrogen atom, or a lower alkyl group, A represents a group

[Formula 61]

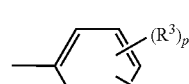

p represents 1 or 2,

R$^3$ represents a hydrogen atom, a lower alkoxy group, a halogen atom, or a lower alkyl group that may have a halogen atom as a substituent, R$^4$ represents a group -(T)$_l$-N(R$^{14}$)R$^{15}$, T represents a group —N($R^{17}$)—$B_3$—CO—, a group —$B_4$—CO—, or a group —CO—,
$R^{17}$ represents a hydrogen atom, or a lower alkyl group,
$B_3$ represents a lower alkylene group,
$B_4$ represents a lower alkylene group that may have a hydroxyl group as a substituent,
l represents 0 or 1,
$R^{14}$ and $R^{15}$, together with the nitrogen atom to which they bind, form a heterocyclic group which is piperidinyl or piperazinyl group that, on the heterocyclic ring, may be substituted by (28) a phenyl-substituted lower alkyl group that may be substituted by a lower alkylenedioxy group on the phenyl ring.

Another more preferred example is a compound represented by the general formula (1) or a salt thereof, wherein
$X_1$ represents a nitrogen atom,
$R^1$ represents a group —Z—$R^6$,
Z represents a group —N($R^8$)—B—,
$R^8$ represents a hydrogen atom, or a lower alkyl group that may have a lower alkoxy group as a substituent,
B represents a group —CO—,
$R^6$ represents a group

[Formula 62]

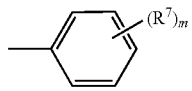

$R^7$ represents a halogen atom or a lower alkyl group that may have a halogen atom as a substituent,
m represents an integer of 1 or 2 (when m represents 2, two $R^7$s may be identical or different) and
$R^2$ represents a hydrogen atom,
Y represents a group —O—, or a group —N($R^5$)—,
$R^5$ represents a hydrogen atom, or a lower alkyl group,
A represents a group

[Formula 63]

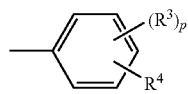

p represents 1 or 2,
$R^3$ represents a hydrogen atom, a lower alkoxy group, a halogen atom, or a lower alkyl group that may have a halogen atom as a substituent,
$R^4$ represents a group -(T)$_1$-N($R^{14}$)$R^{15}$,
$R^{17}$ represents a hydrogen atom, or a lower alkyl group,
$B_3$ represents a lower alkylene group,
$B_4$ represents a lower alkylene group that may have a hydroxyl group as a substituent,
l represents 0,
$R^{14}$ and $R^{15}$, together with the nitrogen atom to which they bind, form a heterocyclic group which is piperidinyl or piperazinyl group
wherein, on the heterocyclic ring, one substituent may be present which is selected from the group consisting of (49) a group) —($B_{12}$CO)t-N($R^{20}$)$R^{21}$, and (84) a group —(O—$B_{15}$)s-CO—N($R^{26}$)$R^{27}$,
$B_{12}$ represents a lower alkylene group,
t represents 0 or 1, $R^{20}$ and $R^{21}$, together with the nitrogen atom to which they bind, form a saturated heterocyclic group which is piperazine or piperidine
wherein, on the heterocyclic ring, one substituent may be present which is a phenyl lower alkyl group that may have a lower alkylenedioxy group as a substituent on the phenyl ring,
$B_{15}$ represents a lower alkylene group,
s represents 0 or 1,
$R^{26}$ and $R^{27}$, together with the nitrogen atom to which they bind, bind to each other, directly or via an oxygen atom or nitrogen atom to form a 6-membered saturated heterocyclic ring (wherein the heterocyclic ring may be substituted by 1 to 3 phenyl lower alkyl groups that may have a lower alkylenedioxy group as a substituent on the phenyl ring).

The aromatic compound (1) or a salt thereof contained in the STAT3/5 activation inhibitor of the present invention includes a stereoisomer, optical isomer and solvate (hydrate, ethanolate, etc.).

Of the aromatic compounds (1), a compound having a basic group may be easily reacted with a conventional pharmacologically acceptable acid to form a salt. Examples of such acid include mineral acids such as hydrochloric acid, hydrobromic acid, nitric acid, sulfuric acid, and phosphoric acid, and organic acids such as methanesulfonic acid, p-toluenesulfonic acid, acetic acid, citric acid, tartaric acid, maleic acid, fumaric acid, malonic acid, and lactic acid.

Of the aromatic compounds (1), a compound having an acidic group may be easily reacted with a conventional pharmacologically acceptable basic compound to form a salt. Examples of such a salt include a sodium salt, a potassium salt, and a calcium salt.

The aromatic compound (1) or a salt thereof can be prepared in the same manner as in WO2006/014012.

Next, a medical formulation containing the aromatic compound (1) or a salt thereof as an active ingredient will be described.

The medical formulation is obtained by formulating the aromatic compound (1) or a salt thereof in the form of pharmaceutical preparation, and more specifically, prepared using a diluent or an excipient such as a filler, expander, binder, moistener, disintegrator, surfactant, or lubricant.

The form of such a medicinal formulation may be chosen from various forms depending upon the therapeutic purpose, and typical forms include tablets, pills, powders, liquids, suspensions, emulsions, granules, capsules, suppositories, and injections (liquids, suspensions).

The carrier to be used in forming tablets may be chosen widely from conventionally known ones. Examples of the carrier include excipients such as lactose, saccharose, sodium chloride, glucose, urea, starch, calcium carbonate, kaolin, and crystalline cellulose, binders such as water, ethanol, propanol, simple syrup, a glucose solution, a starch solution, a gelatin solution, carboxymethylcellulose, shellac, methylcellulose, potassium phosphate, and polyvinylpyrrolidone, disintegrators such as dried starch, sodium arginate, agar powder, laminaran powder, sodium bicarbonate, calcium carbonate, polyoxyethylene sorbitan fatty acid ester, sodium lauryl sulfate, stearic acid monoglyceride, starch, and lactose, anti-disintegrators such as saccharose, stearine, cacao butter, and hydrogenated oil, absorbefacients such as quarternary ammonium base and sodium lauryl sulfate, wetting agents such as glycerol and starch, adsorbents such as starch, lactose, kaolin, bentonite, and colloidal silicate, and lubricants such as purified talc, stearate, boric acid powder, and polyethylene glycol.

Further, tablets may be coated in a conventional manner as needed. Examples of coated tablets include sugar-coated tablets, gelatin-coated tablets, enteric-coated tablets, film-coated tablets, or double or multi-layered tablets.

The carriers to be used in forming pills may be chosen widely from the conventionally known ones. Examples of the carrier include excipients such as glucose, lactose, starch, cacao butter, hydrogenated vegetable oil, kaolin, and talc, binders such as gum arabic powder, tragacanth powder, gelatin, and ethanol, and disintegrators such as laminaran and agar.

The carriers to be used in forming suppositories may be chosen widely from the conventionally known ones. Examples of the carrier include polyethylene glycol, cacao butter, higher alcohols, esters of higher alcohols, gelatin, and semi-synthetic glycerides.

When liquid, emulsion and suspension are prepared as injection preparations, they are preferably sterilized and controlled to be isotonic with the blood. Diluents to be used in forming these liquid, emulsion and suspension preparations may be chosen widely from the conventionally known ones. Examples of the diluents include water, ethanol, propylene glycol, ethoxylated isostearyl alcohol, polyoxylated isostearyl alcohol, and polyoxyethylene sorbitan fatty acid ester. In this case, the medical formulations may contain sodium chloride, glucose or glycerol in a sufficient amount to prepare isotonic solutions. Also, conventional solubilizers, buffers, analgesics, and the like, and, as necessary, coloring agents, preservatives, spices, flavors, sweets and the like, or other pharmaceuticals may be contained.

Although the amount of the aromatic compound (1) or a salt thereof contained in a medical formulation is not particularly limited and may be appropriately selected from a wide range of compounds. It is preferable that the aromatic compound (1) or a salt thereof is contained in an amount of 1 to 70 wt % in a medical formulation.

The method for administrating a medical formulation according to the present invention is not particularly limited. The medical formulation can be administered by a method determined depending upon the form of medical formulation, patient's age, sex, severity of the disease and other conditions. For example, tablets, pills, liquids, suspensions, emulsions, granules and capsules are administered orally. The injection formulations are administered singly or by mixing with a conventional fluid replacement such as a glucose solution or amino acid solution, intravenously or, as necessary, singly administered intramuscularly, intradermally, subcutaneously or intraperitoneally. Suppositories are administered into the rectum.

The dosage for the above mentioned medical formulation may be chosen appropriately depending upon the usage, patient's age, sex and severity of the disease and other conditions. Typically, 0.001 to 100 mg per kg (body weight) per day, preferably 0.001 to 50 mg per kg (body weight) per day, is administered once or in several times a day.

Since the above described dosage varies depending upon various conditions, the dosage may be smaller than the lower limit of the range described above or larger than the upper limit of the range described above.

The aromatic compound (1) or a salt thereof in the present invention has a STAT3/5 activation inhibitory action and useful as a STAT3/5 activation inhibitor.

The aromatic compound (1) or a salt thereof has a STAT3 activation inhibitory action and therefore useful as a medicinal drug for preventing or treating autoimmune disease, diabetes, infection, central disease, cancer-associated disease or psoriasis.

Examples of the autoimmune disease include autoimmune blood dyscrasia (for example, hemolytic anemia, aplastic anemia and idiopathy thrombocytopenia), rheumatism, systemic lupus erythematosus, polychondritis, scleroderma, Wegener's granulomatosis, dermatomyositis, chronic active hepatitis, severe myasthenic, Stevens-Johnson syndrome, idiopathic sprue, inflammatory bowel disease (for example, ulcerative colitis and Crohn disease), endocrine ophthalmopathy, Graves' disease, sarcoidosis, multiple sclerosis, primary biliary cirrhosis, juvenile-onset diabetes (Type I diabetes), uveitis (front and rear uveitis), keratoconjunctivitis sicca, vernal keratoconjunctivitis, psoriatic arthritis, glomerulonephritis (with and without a nephrosis symptom, such as idiopathic nephrotic syndrome or minimal-change nephropathy).

As the central disease, Alzheimer's disease may be mentioned.

As the cancer-associated disease, cachexia may be mentioned.

As the infection, infection with hepatitis C virus (HCV) and infection with Kaposi's sarcoma-associated herpes virus (KSHV) may be mentioned.

Further, the compound of the present invention has a STAT5 activation inhibitory action and is useful as STAT5 activation inhibitor, specifically as preventive or treating agent for autoimmune diseases, allergies, inflammations, hyperprolactinemia and the like as mentioned above.

In the present invention, the aromatic compound (1) or a salt thereof may be used in combination with another STAT3 activation inhibitor, STAT3 activity inhibitor, immunosuppressive agent, antiphlogistic, therapeutic agent for diabetes, therapeutic agent for infectious disease, therapeutic agent for central disease, therapeutic agent for cancer-associated, therapeutic agent for psoriasis, antitumor agent, and fibrosis suppressive agent.

The patents, patent applications and literatures cited in the present invention are incorporated herein by reference.

EXAMPLE 1

Effect of test compound on the amount of STAT3 activated in nucleus of Hep G2 cells after stimulation with IL-6

1) Culture

After Hep G2 cells are washed with PBS (−) twice, they are washed once with trypsin/EDTA solution and detached using trypsin/EDTA solution. The cells are centrifuged and suspended in a medium supplemented with antibiotics (MEM medium (10% FBS +antibiotic (100 U/mL penicillin+100 µg/mL streptomycin)). After the number of cells is counted, the cells are seeded on 12-well plates at a density of $1.2 \times 10^5$ cells/1 mL per well.

Two days after seeding, the culture medium is replaced with 1 mL of antibiotic-free culture medium (MEM medium (10% FBS)).

2) Addition of Test Compound

Two days after medium replacement, a test compound is added so as to obtain concentrations of 0, 1, 10 and 100 nM.

Three hours after addition of the test compound, IL-6 (Code No. KTS102S manufactured by Kamakura Techno Science Inc.) is added at a final concentration 0 or 500 ng/mL.

Five minutes after addition of IL-6, extraction is performed by use of a Nuclear Extraction Kit (Code No. 40410 manufactured by Active Motif Inc.)

3) Extraction of Nuclear Fraction

The supernatant of the cells is removed by suction. The cells are washed with 1 mL of ice-cold phosphatase inhibitor-containing PBS (hereinafter, PBS/phosphatase inhibitor) and the supernatant of the cells is again removed by suction.

The cells are collected with a cell scraper in 0.6 mL of ice-cold PBS/phosphatase inhibitors and divided into ice-cold 1.5 mL microtubes.

After the microtube is centrifuged at 4° C. and a rate of 400×g for 5 minutes, the supernatant is removed.

The cells are resuspended in 0.2 mL of hypotonic buffer by pipetting up and down several times and kept on ice for 15 minutes.

To this suspension, 10 μL of a detergent is added and vortexed for 10 seconds. After centrifugation is performed at 4° C. and a rate of 20,400×g for 30 seconds, the supernatant is removed.

To the resultant cells, 50 μL of Complete Lysis Buffer is added. The suspension is pipetted, vortexed for 10 seconds and shaken on ice for 30 minutes.

After vortexed for 30 seconds, the suspension is centrifuged at 4° C. and a rate of 20,400×g for 10 minutes.

The supernatant is divided into ice-cold 1.5 mL microtubes and stored at −80° C.

4) DNA Binding is Measured by use of TransAM STAT3 Kit (Code No. 45196 Manufactured by Active Motif Inc.)

To each of the wells of an ELISA plate, 30 μL of Complete Binding Buffer and 20 μL of a sample (extracted from a nucleus) are added.

A positive control: 10 μl of Hep G2 nuclear extract (2.5 mg/mL) is diluted with 40 μL of Complete Lysis Buffer (10 μg/20 μL). Dilutions were prepared at 5, 2.5, 1.25, 0.625 and 0.313 μg/20 μL by sequential half-fold dilution, and 20 μL of dilutions is added to each well.

Blank well: 20 μL of Complete Lysis Buffer is added.

After the plate is sealed, the plate is gently shaken at room temperature for one hour, followed by washing with 200 μL of washing buffer three times.

100 μL of a STAT3 antibody is added and the plate is sealed. Thereafter, the plate is gently shaken at room temperature. One hour later, the plate is washed with 200 μL of washing buffer three times. After washing, 100 μL of an HRP-conjugated antibody is added. The plate is sealed, gently shaken at room temperature for one hour, followed by washing with 200 μL of washing buffer four times.

After that, 100 μL of developing solution returned to room temperature is added, and the plate is incubated for 2 to 10 minutes protected from light. After color development is confirmed, 100 μL of stop solution is added and absorbance at 450 nm and 630 nm is determined within 5 minutes.

5) The Results of Test Compounds Listed in Table 1 Below are Shown in Table 2.

TABLE 1

*Test compounds

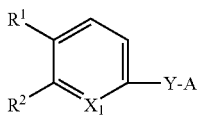

| Test compound No. ( )* | $R^1$ | $R^2$ | $X_1$ | —Y-A |
|---|---|---|---|---|
| 1 (Ex. 582) | (4-CF$_3$-benzoyl)(methyl)amino | H— | N | 4-(methylamino)phenyl-CH$_2$CH$_2$C(O)-piperazine-CH$_2$-benzo[1,3]dioxole |
| 2 (Ex. 1039) | (4-CF$_3$-benzoyl)(methyl)amino | H— | N | 4-methoxyphenyl-CH$_2$CH$_2$C(O)-piperazine-CH$_2$-benzo[1,3]dioxole |
| 3 (Ex. 322) | (4-CF$_3$-benzoyl)(methyl)amino | H— | N | 4-(methylamino)phenyl-piperazine-CH$_2$C(O)-piperazine-CH$_2$-benzo[1,3]dioxole |
| 4 (Ex. 1503) | (4-CF$_3$-benzoyl)(methyl)amino | H— | N | 3-methyl-4-methoxyphenyl-N(CH$_3$)-CH$_2$C(O)-piperazine-CH$_2$-benzo[1,3]dioxole |

TABLE 1-continued

*Test compounds

| Test compound No. ( )* | R¹ | R² | X₁ | —Y-A |
|---|---|---|---|---|
| 5 (Ex. 1049) | F₃C-C₆H₄-C(O)-N(H)-CH₂- | H— | CH | (4-methoxyphenyl)-N(CH₃)-CH₂-C(O)-piperazinyl-CH₂-(benzo[1,3]dioxol-5-yl) |
| 6 (Ex. 940) | F₃C-C₆H₄-C(O)-N(H)-C(O)- | H— | N | (4-methoxy-2-CF₃-phenyl)-N(CH₃)-CH₂-C(O)-piperazinyl-CH₂-(benzo[1,3]dioxol-5-yl) |
| 7 (Ex. 2228) | F₃C-C₆H₄-CH₂-N(CH₃)- | H— | N | (4-methoxy-3-CH₃-phenyl)-NH-C(O)-C(O)-piperazinyl-CH₂-(benzo[1,3]dioxol-5-yl) |
| 8 (Ex. 1202) | F₃C-C₆H₄-C(O)-N(H)-CH₂- | H— | N | (4-methoxy-3-CH₃-phenyl)-piperidinyl-CH₂-C(O)-piperazinyl-CH₂-(benzo[1,3]dioxol-5-yl) |

*: ( ) Numerical value within the parentheses is the number of Example in WO 2006/014012

TABLE 2

Results

| Test compound No. | IC₅₀ (nM) |
|---|---|
| 1 | <150 |
| 2 | <150 |
| 3 | <150 |
| 4 | <150 |
| 5 | <150 |
| 6 | <150 |
| 7 | <150 |
| 8 | <150 |

EXAMPLE 2

Effect of Test Compound on Suppressing Phosphorylation of STAT3
(1) Cells
Seeding of Cells After Hep G2 cells are washed with PBS (−) twice, they are washed and removed by trypsin/EDTA and further removed by trypsin/EDTA. The cells are centrifuged and suspended in a medium supplemented with antibiotics (MEM medium (10% FBS +antibiotic (100 U/mL penicillin+100 μg/mL streptomycin))). After the number of cells is counted, the cells are seeded in a 6-well plate in a rate of 2.4×10⁵/2 mL per well.

Two days later, the medium supplemented with antibiotics is replaced with a medium supplemented with no antibiotics (MEM medium (10% FBS)).
Treatment of Cells with Medicinal Drug Two days after medium replacement, a test compound is added so as to obtain concentrations of 0, 1, 10 and 100 nM.

Three hours after addition of the test compound, IL-6 (Code No. KTS102S manufactured by Kamakura Techno Science Inc.) is added so as to obtain a concentration 100 ng/mL.
Recovery of Cells Five minutes after addition of IL-6, the cells are washed with cooled PBS (−) twice, and peeled off from the plate by a scraper. The cells are collected in a 1.5 mL microtube by use of PBS (−). The cells collected in the 1.5 mL microtube are centrifuged and the supernatant is removed. The cells collected in the 1.5 mL microtube are cryopreserved in a cryogenic refrigerator until use.
Lysis Treatment To the frozen cells, RIPA buffer is added. The frozen cells are suspended by use of 1 mL syringe with a 26G×½ injection needle and the suspension solution is allowed to stand still in ice water for 30 to 60 minutes. The cell suspension solution is centrifuged and the supernatant (cell lysate) is transferred to a new tube. The cell lysate collected in the tube is cryopreserved in a cryogenic refrigerator until use.

Measurement of Protein Concentration

The amount of protein of each cell lysate is measured in accordance with the protocol attached to a BCA protein assay reagent set.

(2) Western Blotting Analysis

PAGE (Electrophoresis)

After the protein amount of each cell lysate is set at the same value, denature treatment is performed under reduced conditions. After the samples and a molecular marker are applied to polyacrylamide gel, electrophoresis is performed.

Blotting

After completion of electrophoresis, the gel is equilibrated with the solution to be used in transferring.

The proteins developed on the polyacrylamide gel are transferred onto a PVDF (polyvinylidene difluoride) film by a semidry type transferring apparatus.

Blocking/Washing

After the PVDF film is washed, it is soaked in blocking buffer (5% BSA) to perform blocking.

Primary Antibody (Phospho-STAT3 (Ser 727) Antibody or Phospho-STAT3 (Tyr 705) Antibody)

Blocked PVDF film is reacted with the primary antibody.

Secondary Antibody (Anti-Rabbit-IgG HRP-Linked Antibody)/Washing

After washed, the PVDF film is reacted with the HRP labeled antibody.

Detection of Color Emission by ECL

After the PVDF film is washed, color is allowed to emit by use of ECL Western Blotting Detection Reagents and fluorescence is detected by LAS-3000.

According to the Aforementioned Method, the Effect of the Test Compound on Surppressing Phosphorylation of STAT3 is Measured.

EXAMPLE 3

Effect of test compound on prolactin-induced STAT5 activation in 22Rv1 cells

1) Culture

After 22Rv1 cells cryopreserved are subcultured at least twice, they are subjected to a test. After culture until subconfluency, the cells are washed with D-PBS (−). Thereafter, they are detached using trypsin/EDTA solution and suspended in a medium (RPMI-1640 medium (10% FBS+antibiotics (100 U/mL penicillin+100 µg/mL streptomycin)). The cell suspension solution is centrifuged at 150×g, for 5 minutes at 20 to 25° C. The supernatant is removed and the pellet is resuspended in the medium. An aliquot of the cell suspension solution is taken and dead cells are stained with trypan blue. The number of viable cells is counted by a hemocytometer. A cell suspension solution is prepared so as to contain $2 \times 10^5$ cells/mL, and cells are seeded in a 12 well-plate in a rate of $2 \times 10^5$ cells/mL per well. Cells are cultured in a $CO_2$ incubator (5% $CO_2$, 37° C.)

2) Addition of Test Compound

Two days after seeding, a test compound is added so as to obtain concentrations of 0 and 1000 nM.

Three hours after addition of the test compound, recombinant human prolactin (rhPRL, R&D systems Inc.) is added so as to obtain a concentration of 0 or 250 ng/mL.

3) Extraction of Cytoplasmic Fraction

Fifteen minutes after addition of prolactin, extraction is performed by a Nuclear Extract Kit (Code No. 40410 manufactured by Active Motif Inc.). At 15 minutes after the addition of prolactin, the supernatant is removed and prolactin-stimlation is immediately stopped by adding 1 ml of ice-cold PBS/phosphatase inhibitor. After aspirating 1 mL of ice-cold PBS/phosphatase inhibitor, 0.6 mL of ice-cold PBS/phosphatase inhibitor is added and centrifuged at 200×g, for 5 minutes at 4° C.

After the supernatant is removed, 0.2 mL of hypotonic buffer is added and suspended. After the suspension is kept on ice for 15 minutes, 10 µL of a detergent is added. After the solution is further stirred, it is centrifuged at 14,000×g, for one minute at 4° C. The resultant supernatant (cytoplasmic fraction) is divided to three ice-cold 96-well plates, and stored in a freezer of −80° C.

4) Measurement of Activated STATS

Measurement is performed by use of reagents attached to TransAM™STAT family kit. To describe more specifically, to each of the wells of an ELISA plate of the TransAM™STAT family kit, 30 µL of Complete Binding Buffer is added, and thereafter, 20 µL of the cytoplasmic fraction is added. As a sample for calibration curve, 12 µL of a cell nuclear fraction reference sample (Nb2 nuclear fraction (prolactin stimulated, 2.5 µg/µL)) attached to the TransAM™STAT family kit is diluted with 48 µL of Complete Lysis Buffer (to 10 µg/20 µL), and further serially diluted in half to prepare diluted solutions of 5, 2.5, 1.25, 0.625, 0.313, and 0.156 µg/20 µL. 20 µl of each of the dilution solution is added to well. As a blank, 20 µL of Complete Lysis Buffer is added. After addition of a sample, the plate is sealed and gently shaken at room temperature for one hour. After that, the plate is washed with 200 µL of wash buffer three times. Next, 100 µL of STAT5B antibody is added, sealed and incubated at room temperature without agitation. One hour later, the plate is washed with 200 µL of wash buffer three times. 100 µL of a Horseradish Peroxidase (HRP)-conjugated antibody is added, sealed and incubated at room temperature without agitation. One hour later, the plate is washed with 200 µL of wash buffer four times and 100 µL of a developing solution is added. The plate is incubated for 2 to 10 minutes protected from light. After color development is confirmed, 100 µL of a stop solution is added. Immediately after, absorbance at 450 nm (measurement wavelength) and 630 nm (reference wavelength) is determined using a plate reader.

The amount of phosphorylated STAT5B dimer is estimated based on a calibration curve. Further, a ratio (T/C %) of the amount of phosphorylated STAT5B dimer in the presence of each medicinal drug relative to that in the absence of a medicinal drug is calculated. The results of test compounds listed in Table 1 are shown in Table 3.

TABLE 3

| Test compound No. | | T/C % |
|---|---|---|
| Object (DMSO) | 0 | 100 |
| 1 | 1000 nM | <30 |
| 2 | 1000 nM | <30 |
| 3 | 1000 nM | <30 |
| 4 | 1000 nM | <30 |
| 5 | 1000 nM | <30 |
| 6 | 1000 nM | <30 |
| 7 | 1000 nM | <30 |
| 8 | 1000 nM | <30 |

EXAMPLE 4

Effect of test compound on dextran sulfate sodium (DSS) induced colitis model

1. Induction of Colitis by DSS

After female mice C57BL/6J Jms Slc are preliminarily raised for a week, the mice are grouped based on the body weight (BW) of the mice at the grouping day and in accordance with stratified random sampling.

DSS (Lot No, 4556J, MP Biomedicals) is dissolved in Otsuka distilled water to prepare a 4% DSS solution. Mice are allowed to drink the 4% DSS solution freely for 7 days from the following day (Day 2) after initiation of administration to induce colitis.

2. Administration of Test Compound and Solvent

Based on the body weight before administration of the DSS solution (Day 1) and the most recent body weight after administration of the DSS solution, each administration solution is orally administered in a dose of 10 mL/kg once a day.

The dose of the test compound is 300 mg/kg.

An administration solution is prepared by suspending a test compound in a 5% gum arabic solution so as to contain the test compound in a concentration of 30 mg/mL.

3. Autopsy

Autopsy is performed at Day 8.

4. Collection of Blood

After blood is collected from the abdominal posterior vena cava under anaesthesia with diethyl ether, it is immediately transferred to a BD Microtainer® (Nippon Becton, Dickinson and Company), mixed by overturning the Micro-Tina and allowed to stand still in ice. The Micro-Tina is centrifuged by use of a refrigerated centrifuge (HITACHI CF9RX, T3S51 rotor) at 4° C. and 2,150×g for 20 minutes to obtain heparin plasma. The plasma dispensed is cryopreserved in a freezer (−80° C.) until use in measurement.

5. Collection of Organ

After the abdominal posterior vena cava is cut under anaesthesia with diethyl ether to kill a mouse by blood letting, the spleen is excised out. The weight of the spleen is measured by an electronic force balance. And, the large intestine was immediately removed for measurement of intestinal length and evaluation of intestinal shortening.

6. Measurement Items

Body Weight

Body weight is measured at Day 1 (day of grouping), 3, 5, 7 and 8 (day of autopsy) by an electronic force balance.

Based on the body weight of Day 1 (day of grouping) and Day 8 (day of autopsy), a body weight change is calculated.

Spleen Weight

The wet weight of the spleen is measured by an electronic force balance.

In addition, from the measurement results of spleen weight, a ratio (T/C %) of the spleen weight relative to an average spleen weight of a control group and a spleen weight gain inhibition ratio (IR %) are calculated.

Intestinal Length

The length of the large intestine is measured by a scale.

In addition, from the measurement results of intestinal length, a ratio (T/C%) of the intestinal length relative to an average intestinal length of a control group and an intestinal shortening inhibition ratio (IR%) are calculated.

The results of test compounds are shown in Table 4.

TABLE 4

| Test compound No. | Spleen weight gain inhibition ratio IR (%) |
|---|---|
| 9 (Example 305 of WO2006/014012) | >40 |
| 10 (Example 1105 of WO2006/014012) | >40 |
| 11 (Example 1503 of WO2006/014012) | >40 |

The invention claimed is:

1. A method for inhibiting STAT3 activation in a patient having a symptom or disease selected from autoimmune disease, diabetes, infection, Alzheimer's disease, psoriasis, but not fibrosis, comprising administering, to said patient, an effective amount of a compound selected from the group consisting of:
  (1) N-[6-(4-{[2-(4-piperonylpiperazin-1-yl)-2-oxoethyl]ethylaminol}-2-methoxyphenoxy)pyridin-3-yl]-3,4-dichlorobenzamide,
  (2) N-{2[4-(1,3-benzodioxol-5-ylmethyl)piperazin-1-yl]-2-oxoethyl}-N-{4-[(5-{methyl[4-(trifluoromethyl)benzyl]amino}pyridin-2-yl)oxy]phenyl}acetamide
  (3) N-(6-{4-[3-(4-piperonylpiperazin-1-yl)-3-oxopropyl]phenoxy}pyridin-3-yl)-4-trifluoromethylbenzamide,
  (4) N-[4-(4-{[2-(4-piperonylpiperazin-1-yl)-2-oxoethyl]methylamino}phenoxy)phenyl]-4-trifluoromethylbenzamide,
  (5) N-[6-(4-{[2-(4-piperonylpiperazin-1-yl)-2-oxoethyl]ethylamino}-2-methoxyphenoxy)pyridin-3-yl]-4-trifluoromethylbenzamide,
  (6) N-[6-(4-{[2-(4-piperonylpiperazin-1-yl)-2-oxoethyl]methylamino}-2-methylphenoxy)pyridin-3-yl]-4-trifluoromethylbenzamide, and
  (7) N-[6-(4-{[(4-pivaloylbenzyl)piperazin-1-yl]oxomethyl}phenoxy)pyridin-3-yl]-3,4-dichlorobenzamide,
  or a salt thereof.

2. A method for inhibiting STAT3 activation in a patient having a symptom or diseas e selected from autoimmune disease, diabetes, infection, Alzheimer's disease, psoriasis, but not fibrosis, comprising administering, to said patient, an effective amount of a compound selected from the group consisting of:
  N-(6-{[4-(4-{2-[4-(1,3-benzodioxol-5-ylmethyl)piperazin-1-yl]-2-oxoethyl}piperazin-1-yl)phenyl](methyl)amino}pyrid in-3-yl)-4-(trifluoromethyl)benzamide,
  N-{6-[(4-(3-[4-(1,3-benzodioxol-5-ylmethyl)piperazin-1-yl]-3-oxopropyl}phenyl)(methy)amino]pyridin-3-yl}-4-(trifluoromethyl)benzamide,
  6-{4-[{2-[4-(1,3-benzodioxol-5-ylmethyl)piperazin-1-yl]-2-oxoethyl}(methy)amino]-3-(trifluoromethyl)phenoxyl}-N[4-(trifluoromethyl)phenyl]pyridine-3-carboxamide,
  N-[6-(4-{3-[4-(1,3-benzodioxol-5-ylmethyl)piperazin-1-yl]-3-oxopropyl}phenoxy)pyridin-3-yl]-4-(trifluoromethyl)benzamide,
  N-(4-{4-[{2-[4-(1,3-benzodioxol-5-ylmethyl)piperazin-1-yl]-2-oxoethyl}(methy)amino]phenoxy}phenyl)-4-(trifluoromethyl)benzamide,
  N-{6-[4-(4-{2-[4-1,3-benzodioxol-5-ylmethyl)piperazin-1-yl]-2-oxoethyl}piperidin-1-yl)-2-methylphenoxy]pyridin-3-yl}-4-(trifluoromethy)benzamide, N-(6-{4-[{2-[4-(1,3-benzodioxol-5-ylmethyl)piperazin-1-yl]-2-oxoethyl}(methy)amino]-2-methylphenoxy}pyridin-3-yl)-4-(trifluoromethyl)benzamide, or a salt thereof.

3. The method according to claim 1, wherein the autoimmune disease is selected from polychondritis, Stevens-Johnson syndrome, idiopathic sprue, endocrine ophthalmopathy, Graves' disease, multiple sclerosis, uveitis, keratoconjunctivitis sicca, or vernal keratoconjuctivitis.

4. The method according to claim 2, wherein the autoimmune disease is selected from polychondritis, Stevens-Johnson syndrome, idiopathic sprue, endocrine ophthalmopathy, Graves' disease, multiple sclerosis, uveitis, keratoconjunctivitis sicca, or vernal keratoconjuctivitis.

5. The method according to claim 1, wherein the symptom or disease is diabetes.

6. The method according to claim 2, wherein the symptom or disease is diabetes.

* * * * *

UNITED STATES PATENT AND TRADEMARK OFFICE
CERTIFICATE OF CORRECTION

PATENT NO. : 8,263,599 B2
APPLICATION NO. : 12/311500
DATED : September 11, 2012
INVENTOR(S) : Kazuo Sekiguchi et al.

It is certified that error appears in the above-identified patent and that said Letters Patent is hereby corrected as shown below:

In the Claims:

* In claim 2, column 96, line 44, "diseas e" should read --disease--.

* In claim 2, column 96, line 51, "amino}pyrid in-3-yl)-4-(trifluoromethyl)benzamide," should read -- amino} yridine-3-yl)-4-(trifluoromethyl)benzamide,--.

* In claim 2, column 96, line 56-57, "6-{4-[{2-[4-(1,3-benzodioxol-5-ylmethyl)piperazin-1-yl]-2-oxoethyl}(methy)amino]-3-(trifluoromethyl)phenoxyl}-N[4-(trifluoromethyl)phenyl]pyridine-3-carboxamide,"

should read

--6-{4-[{2-[4-(1,3-benzodioxol-5-ylmethyl)piperazin-1-yl]-2-oxoethyl}(methyl)amino]-3-(trifluoromethyl)phenoxy}-N[4-(trifluoromethyl)phenyl]pyridine-3-carboxamide,--.

* In claim 2, column 96, line 67, "pyridine-3-yl}-4-(trifluoromethy)benzamide," should read -- pyridine-3-yl}-4-(trifluoromethyl)benzamide,--.

In claim 3, column 97, line 10, "keratoconjuctivitis" should read --keratoconjunctivitis--.

In claim 4, column 98, line 5, "keratoconjuctivitis" should read --keratoconjunctivitis--.

Signed and Sealed this
Twenty-third Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,263,599 B2
APPLICATION NO.    : 12/311500
DATED              : September 11, 2012
INVENTOR(S)        : Kazuo Sekiguchi et al.

It is certified that error appears in the above-identified patent and that said Letters Patent is hereby corrected as shown below:

In the Claims:

* In claim 2, column 96, line 44, "diseas e" should read --disease--.

* In claim 2, column 96, line 51, "amino}pyrid in-3-yl)-4-(trifluoromethyl)benzamide," should read -- amino} yridine-3-yl)-4-(trifluoromethyl)benzamide,--.

* In claim 2, column 96, line 56-57, "6-{4-[{2-[4-(1,3-benzodioxol-5-ylmethyl)piperazin-1-yl]-2-oxoethyl}(methy)amino]-3-(trifluoromethyl)phenoxyl}-N[4-(trifluoromethyl)phenyl]pyridine-3-carboxamide,"

should read

--6-{4-[{2-[4-(1,3-benzodioxol-5-ylmethyl)piperazin-1-yl]-2-oxoethyl}(methyl)amino]-3-(trifluoromethyl)phenoxy}-N[4-(trifluoromethyl)phenyl]pyridine-3-carboxamide,--.

* In claim 2, column 96, line 67, "pyridine-3-yl}-4-(trifluoromethy)benzamide," should read -- pyridine-3-yl}-4-(trifluoromethyl)benzamide,--.

In claim 3, column 97, line 10, "keratoconjuctivitis" should read --keratoconjunctivitis--.

In claim 4, column 98, line 5, "keratoconjuctivitis" should read --keratoconjunctivitis--.

This certificate supersedes the Certificate of Correction issued July 23, 2013.

Signed and Sealed this
Twenty-fourth Day of September, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,263,599 B2  Page 1 of 1
APPLICATION NO. : 12/311500
DATED : September 11, 2012
INVENTOR(S) : Kazuo Sekiguchi et al.

It is certified that error appears in the above-identified patent and that said Letters Patent is hereby corrected as shown below:

In the Claims:

* In claim 2, column 96, line 44, "diseas e" should read --disease--.

* In claim 2, column 96, line 51, "amino}pyrid in-3-yl)-4-(trifluoromethyl)benzamide," should read --amino}pyridin-3-yl)-4-(trifluoromethyl)benzamide--.

* In claim 2, column 96, line 56-57, "6-{4-[{2-[4-(1,3-benzodioxol-5-ylmethyl)piperazin-1-yl]-2-oxoethyl}(methy)amino]-3-(trifluoromethyl)phenoxyl}-N[4-(trifluoromethyl)phenyl]pyridine-3-carboxamide," should read --6-{4-[{2-[4-(1,3-benzodioxol-5-ylmethyl)piperazin-1-yl]-2-oxoethyl}(methyl)amino]-3-(trifluoromethyl)phenoxy}-N[4-(trifluoromethyl)phenyl]pyridine-3-carboxamide,--.

* In claim 2, column 96, line 67, "pyridine-3-yl}-4-(trifluoromethy)benzamide," should read --pyridine-3-yl}-4-(trifluoromethyl)benzamide,--.

* In claim 3, column 97, line 10, "keratoconjuctivitis" should read --keratoconjunctivitis--.

* In claim 4, column 98, line 5, "keratoconjuctivitis" should read --keratoconjunctivitis--.

This certificate supersedes the Certificates of Correction issued July 23, 2013 and September 24, 2013.

Signed and Sealed this
Twenty-fifth Day of March, 2014

Michelle K. Lee
*Deputy Director of the United States Patent and Trademark Office*